US008536133B2

(12) United States Patent
DeNardo et al.

(10) Patent No.: US 8,536,133 B2
(45) **Date of Patent: *Sep. 17, 2013**

(54) SELECTIVE HIGH-AFFINITY POLYDENTATE LIGANDS AND METHODS OF MAKING SUCH

(75) Inventors: Sally DeNardo, Livermore, CA (US); Gerald DeNardo, Livermore, CA (US); Rodney Balhorn, Livermore, CA (US)

(73) Assignees: Lawrence Livermore National Security, LLC., Livermore, CA (US); The Regents of the University of California, Oakland, CA (US)

( * ) Notice: Subject to any disclaimer, the term of this patent is extended or adjusted under 35 U.S.C. 154(b) by 563 days.

This patent is subject to a terminal disclaimer.

(21) Appl. No.: 12/642,684

(22) Filed: Dec. 18, 2009

(65) Prior Publication Data

US 2010/0184702 A1 Jul. 22, 2010

Related U.S. Application Data

(63) Continuation of application No. 11/055,181, filed on Feb. 9, 2005, now Pat. No. 7,662,785.

(60) Provisional application No. 60/543,444, filed on Feb. 9, 2004.

(51) Int. Cl.
*A61K 38/00* (2006.01)
*A61K 31/33* (2006.01)

(52) U.S. Cl.
USPC .......................................... 514/19.3; 514/183

(58) Field of Classification Search
None
See application file for complete search history.

(56) References Cited

U.S. PATENT DOCUMENTS 4,331,647 A 5/1982 Goldenberg
4,361,544 A 11/1982 Goldenberg
4,444,744 A 4/1984 Goldenberg
4,921,690 A 5/1990 Beatty et al.
5,034,223 A 7/1991 Abrams et al.
5,595,721 A 1/1997 Kaminski et al.
5,601,819 A 2/1997 Wong et al.
5,959,084 A 9/1999 Ring et al.
5,985,276 A 11/1999 Lindhofer et al.
6,010,902 A 1/2000 Ledbetter et al.
6,060,285 A 5/2000 Lenz et al.
6,106,833 A 8/2000 Ring et al.
6,210,668 B1 4/2001 Lindhofer et al.
6,217,871 B1 4/2001 Rose et al.
2001/0001310 A1 5/2001 Weiner et al.
2002/0155109 A1 10/2002 Lynch
2003/0077282 A1 4/2003 Bigler et al.
2003/0176662 A1 9/2003 Bolognesi et al.
2004/0242851 A1 12/2004 Zhu
2005/0079184 A1 4/2005 Hsing-Chang et al.
2005/0136050 A1 6/2005 Kufer et al.
2006/0018897 A1 1/2006 Lee et al.

FOREIGN PATENT DOCUMENTS

WO WO 99/53953 10/1999
WO WO 2005/077065 8/2005

OTHER PUBLICATIONS

Balhorn et al. (2009) "Hexa-arginine enhanced uptake and residualization of selective high affinity ligands by Raji lymphoma cells" *Molecular Cancer* 8:25.
Balhorn et al. (2007) "Selective High-Affinity Ligand Antibody Mimics for Cancer Diagnosis and Therapy: Initial Application to Lymphoma/Leukemia" *Clin. Cancer Res.* 13(18 Suppl):5621S-5628S.
Cirino et al. (1999) "Disruption of anthrax toxin binding with the use of human antibodies and competitive inhibitors" *Infection and Immunity* 67(6):2957-2963.
Cosman et al. (2002) "Identification of Novel Small Molecules that Bind to Two Different Sites on the Surface of Tetanus Toxin C Fragment" *Chem. Res. Toxicol.* 15:1218-1228.
DeNardo et al. (1998) "Comparison of 1,4,7,10-tetraazacyclododecaine-N,N',N",N'"-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts" *Clin. Cancer Res.* 4(10):2483-2490.
DeNardo et al. (1997) "Yttrium-90/Indium-111-DOTA-peptide-Chimeric L6: Pharmacokinetics, dosimetry and initial results in patients with incurable breast cancer" *Anticancer Research* 17:1735-1744.
DeNardo et al. (2007) "Characteristics of dimeric (bis) bidentate selective high affinity ligands as HLA-DR10 beta antibody mimics targeting non-Hodgkin's lymphoma" *International Journal of Oncology* 31:729-740.
DeNardo et al. (2009) "Molecular specific and cell selective cytotoxicity induced by a novel synthetic HLA-DR antibody mimic for lymphoma and leukemia" *International Journal of Oncology* 34:511-516.
DeNardo et al. (2008) "Nanomolecular HLA-DR10 Antibody Mimics: A Potent System for Molecular Targeted Therapy and Imaging" *Cancer Biotherapy & Radiopharmaceuticals* 23(5):783-796.
DeNARDO et al. (2007) "Pharmacokinetic Characterization in Xenografted Mice of a Series of First-Generation Mimics for HLA-DR Antibody, Lym-1, as Carrier Molecules to Image and Treat Lymphoma" *J. Nucl. Med.* 48:1338-1347.
Fan et al. (2000) "AB(5) Toxins: Structures and inhibitor design" *Current Opinion in Structural Biology* 10:680-686.
Henrichsen et al. (1999) "Bioaffinity NMR Spectroscopy: Identification of an E-Selectin Antagonist in a Substance Mixture by Transfer NOE" *Angew Chem. Int. Edit.* 38:98-102.
Hok et al. (2007) "Synthesis and radiolabeling of selective high-affinity ligands designed to target non-Hodgkin's lymphoma and leukemia" *Bioconjugate Chem.* 18:912-921.
Kostelny et al. (2001) "Humanization and characterization of the anti-HLA-DR antibody 1D10" *International Journal of Cancer* 93:556-65.

(Continued)

*Primary Examiner* — James D Anderson
(74) *Attorney, Agent, or Firm* — Foley & Lardner, LLP.

(57) ABSTRACT

This invention provides polydentate selective high affinity ligands (SHALs) that can be used in a variety of applications in a manner analogous to the use of antibodies. SHALs typically comprise a multiplicity of ligands that each binds different regions on the target molecule. The ligands are joined directly or through a linker thereby forming a polydentate moiety that typically binds the target molecule with high selectivity and avidity.

33 Claims, 22 Drawing Sheets

(56) References Cited

OTHER PUBLICATIONS

Kramer & Karpen (1998) "Spanning binding sites on allosteric proteins with polymer-linked ligand dimmers" *Nature* 395:710-713.

Lehnert et al. (2001) "Structure-based design of a bispecific receptor mimic that inhibits T cell responses to a superantigen" *Biochemistry* 40(14):4222-4228.

Mammen et al. (1998) "Polyvalent interactions in biological systems: Implications for design and use of multivalent ligands and inhibitors" *Angew Chem. Int. Edit.* 37:2755-2794.

Shoichet et al. (2002) "Lead Discovery Using Molecular Docking" *Current Opinion in Chemical Biology* 6:439-446.

Shuker et al. (1996) "Discovering High-Affinity Ligands for Proteins: SAR by NMR" *Science* 274:1531-1534.

West et al. (2006) "Direct Antilymphoma Activity of Novel, First-Generation "Antibody Mimics" that Bind HLA-DR10-Positive Non-Hodgkin's Lymphoma Cells" *Cancer Biotherapy & Radiopharmaceuticals* 21(6):645-654.

DeNardo, et al., "Systemic Radiotherapy Can Cure Lymphoma: A Paradigm for Other Malignancies?", Cancer Biotherapy & Radiopharmaceuticals, vol. 23, No. 4, pp. 383-397 (2008).

Normal MUC1

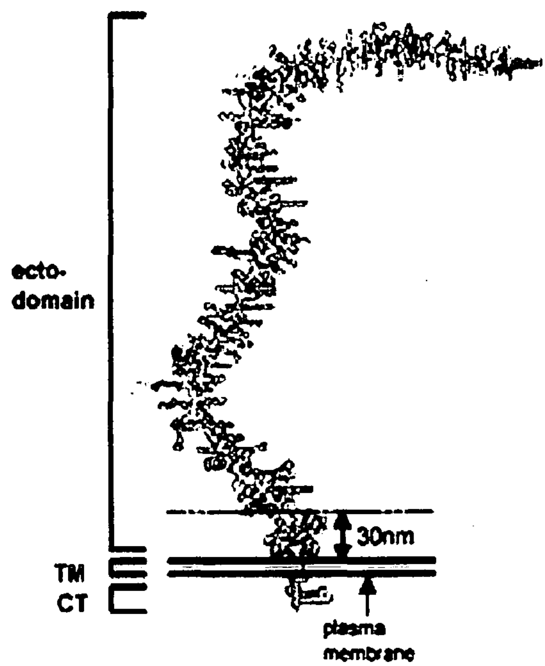

Epithelial tissues that normally express MUC1

- mammary gland
- female reproductive tract (except ovary)
- prostate
- testis
- salivary gland
- digestive tract (except large intestine and colon)
- pancreas
- liver (bile ducts)
- lung
- kidney (distal tubules and collecting ducts)
- bladder
- eye Non-epithelial cells that express MUC1:

- hematopoietic cells
- activated T cells

*Fig. 4A*

```
                                                   *  **    .  ****:***:***  *  *
hla_dr10 ------------------------------GDTRPRFLEEVKFECHFFNGTERVRLLERR   30
 laqd_B  ------------------------------GDTRPRFLWQLKFECHFFNGTERVRLLERC   30
 ld5m_B  ------------------------------GDTRPRFLEQVKHECHFFNGTERVRFLDRY   30
 lbx2_B  --------------------------------TRPRFLWQPKRECHFFNGTERVRFLDRY   28
 la6a_B  ----------------------------------PRFLEYSTSECHFFNGTERVRYLDRY   26
 li3r_B  RDSRGKKVITAFNEGLKGGGGSLVGGGSGGGGSRPWELEYCKSECHFYNGTQRVRLLVRY   60

         .::  **   *:*******:************  ****  ::**:  *. **.  *****  :  :.*
hla_dr10 VHNQEEYARYDSDVGEYRAVTELGRPDAEYWNSQKDLLERRRAAVDTYCRHNTGVGESFT   90
 laqd_B  IYNQEESVRFDSDVGEYRAVTELGRPDAEYWNSQKDLIEQRRAAVDTYCRHNYGVGESFT   90
 ld5m_B  FYHQEEYVRFDSDVGEYRAVTELGRPDAEYWNSQKDLLEQKRAAVDTYCRHNYGVGESFT   90
 lbx2_B  FYNQEESVRFDSDVGEFRAVTELGRPDAEYWNSQKDIIEQARAAVDTYCRHNYGVVESFT   88
 la6a_B  FHNQEENVRFDSDVGEFRAVTELGRPDAEYWNSQKDLIEQKRGRVDNYCRHNYGVVESFT   86
 li3r_B  TYNLEENLRFDSDVGEFRAVTELGRPDAENWNSQPEFIEQKRAEVDTVCRHNYEIFDNFL  120

         *  ***  *  *****:*****:*********..****.******  **:***:*:*****::*
hla_dr10 VQRRVQPKVTVYPSKTQPLQHHNLLVCSVNGFYPGSIEVRWFRNGQEEKYGVVSTGLIQN  150
 laqd_B  VQRRVEPKVTVYPSKTQPLQHHNLLVCSVSGFYPGSIEVRWFRNGQEERAGVVSTGLIQN  150
 ld5m_B  VQRRVYPRVTVYPAKTQPLQHHNLLVCSVNGFYPGSIEVRWFRNGQEEKTGVVSTGLIQN  150
 lbx2_B  VQRRVQPKVTVYPSKTQPLQHHNLLVCSVSGFYPGSIEVRWFLNGQEEKAGMVSTGLIQN  148
 la6a_B  VQRRVHPKVTVYPSKTQPLQHHNLLVCSVSGFYPGSIEVRWFRNGQEEKTGVVSTGLIHN  146
 li3r_B  VPRRVEPTVTVYPTKTQPLEHHNLLVCSVSDFYPGNIEVRWFRNGKEEKTGIVSTGLVRN  180

         ***************:**************:  .*:****:*:
hla_dr10 GDWTFQTLVMLETVPQSGEVYTCQVEHPSVMSPLTVEWRARSESAQSKMLSGVGGFVLGL  210
 laqd_B  GDWTFQTLVMLETVPRSGEVYTCQVEHPSVTSPLTVEWRARSESAQSK------------  198
 ld5m_B  GDWTFQTLVMLETVPRSGEVYTCQVEHPSVTSPLTVEWRARS------------------  192
 lbx2_B  GDWTFQTLVMLETVPRSGEVYTCQVEHPSVTSPLTVEWRARSE-----------------  191
 la6a_B  GDWTFQTLVMLETVPRSGEVYTCQVEHPSVTSPLTVEWRAR-------------------  187
 li3r_B  GDWTFQTLVMLETVPQSGEVYTCQVEHPSLTDPVTVEWKAQSTSAQNK------------  228

hla_dr10 LFLGAGLFIYFRNQKGHSGLPPTGFLS   237
 laqd_B  ---------------------------   198
 ld5m_B  ---------------------------   192
 lbx2_B  ---------------------------   191
 la6a_B  ---------------------------   187
 li3r_B  ---------------------------   228
```

*Fig. 8*

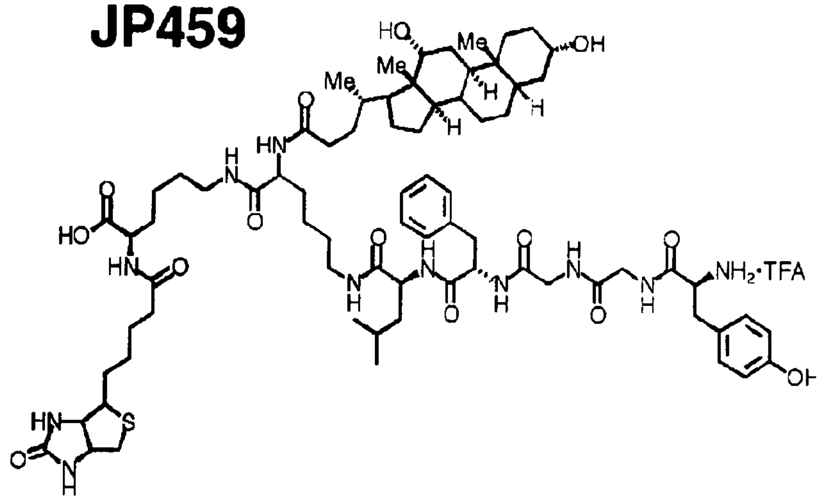
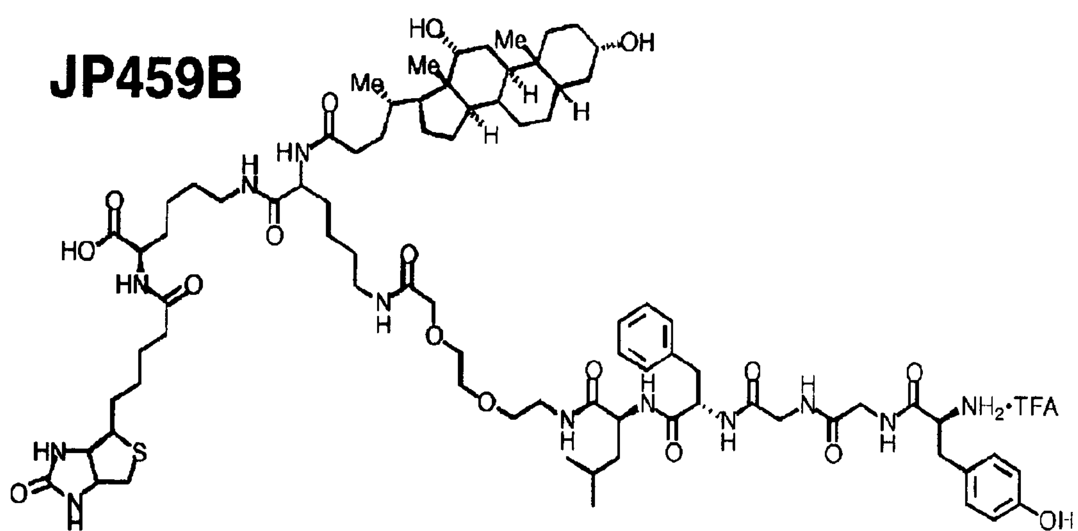
*Fig. 13B*

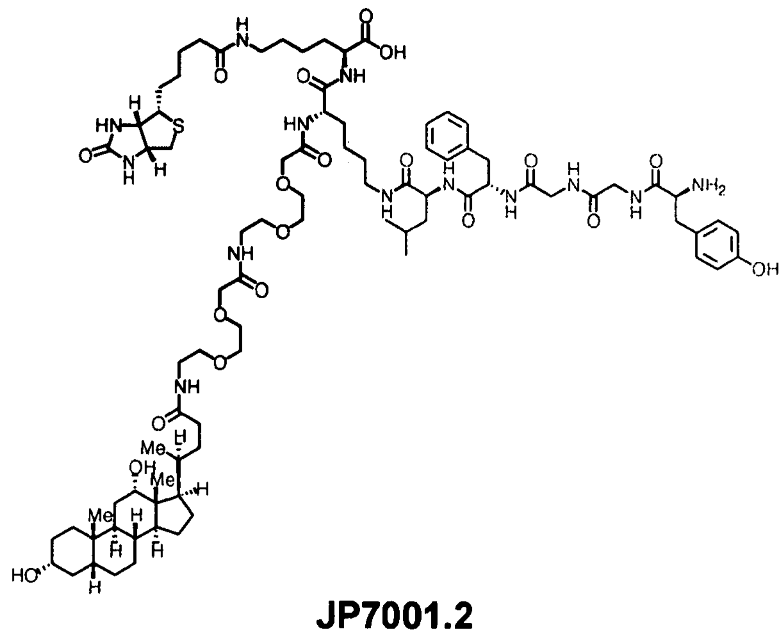
JP7001.2
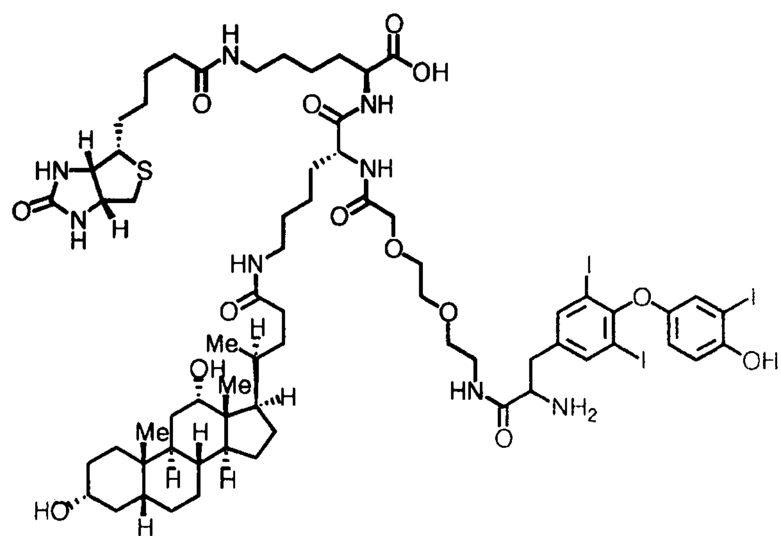
*Triiodothyronine-deoxycholate SHAL*
*Fig. 23*

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Tyr Lys Asp Asp Asp Asp Lys
1               5


<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Val Thr Ser Ala Pro Asp Thr Arg Pro Ala Pro Gly Ser Thr Ala
1               5                   10                  15

Pro Pro Ala His
            20
```

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser
1               5


<210> SEQ ID NO 4
<211> LENGTH: 5
<212> TYPE: PRT
<213> ORGANISM: Pseudomonas aeruginosa

<400> SEQUENCE: 4

Arg Glu Asp Leu Lys
1               5


<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Glu Asp Leu
1


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Asp Glu Leu
1


<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Asp Glu Leu
1


<210> SEQ ID NO 8
<211> LENGTH: 4
<212> TYPE: PRT
<213> ORGANISM: Unknown
<220> FEATURE:
<223> OTHER INFORMATION: Description of Unknown: Ligand peptide

<400> SEQUENCE: 8

Arg Gly Asp Thr
1
```

<210> SEQ ID NO 9
<211> LENGTH: 4
<212> TYPE: PRT
<213> ORGANISM: Unknown
<220> FEATURE:
<223> OTHER INFORMATION: Description of Unknown: Ligand peptide

<400> SEQUENCE: 9

Asp Arg Val Tyr
1

<210> SEQ ID NO 10
<211> LENGTH: 3
<212> TYPE: PRT
<213> ORGANISM: Unknown
<220> FEATURE:
<223> OTHER INFORMATION: Description of Unknown: Ligand peptide

<400> SEQUENCE: 10

Glu Thr Pro
1

<210> SEQ ID NO 11
<211> LENGTH: 5
<212> TYPE: PRT
<213> ORGANISM: Unknown
<220> FEATURE:
<223> OTHER INFORMATION: Description of Unknown: Ligand peptide
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: D-Met

<400> SEQUENCE: 11

Tyr Ala Gly Phe Met
1               5

<210> SEQ ID NO 12
<211> LENGTH: 4
<212> TYPE: PRT
<213> ORGANISM: Unknown
<220> FEATURE:
<223> OTHER INFORMATION: Description of Unknown: Ligand peptide

<400> SEQUENCE: 12

Arg Gly Asp Thr
1

<210> SEQ ID NO 13
<211> LENGTH: 3
<212> TYPE: PRT
<213> ORGANISM: Unknown
<220> FEATURE:
<223> OTHER INFORMATION: Description of Unknown: Ligand peptide

<400> SEQUENCE: 13

Glu His Pro
1

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 14

His His His His His His
1 5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
4xHis tag

<400> SEQUENCE: 15

His His His His
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
5xHis tag

<400> SEQUENCE: 16

His His His His His
1 5

<210> SEQ ID NO 17
<211> LENGTH: 4
<212> TYPE: PRT
<213> ORGANISM: Unknown
<220> FEATURE:
<223> OTHER INFORMATION: Description of Unknown: Ligand peptide

<400> SEQUENCE: 17

Val Ile His Asn
1

<210> SEQ ID NO 18
<211> LENGTH: 5
<212> TYPE: PRT
<213> ORGANISM: Unknown
<220> FEATURE:
<223> OTHER INFORMATION: Description of Unknown: Ligand peptide

<400> SEQUENCE: 18

Tyr Ala Gly Phe Met
1 5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Leu Phe Gly Gly Tyr
1 5

<210> SEQ ID NO 20
<211> LENGTH: 56
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 20

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
            20                  25                  30

Pro Ala His Gly Val Thr Ser Ala Pro Asp Thr Arg Pro Ala Pro Gly
        35                  40                  45

Ser Thr Ala Pro Pro Ala His Gly
    50                  55


<210> SEQ ID NO 21
<211> LENGTH: 237
<212> TYPE: PRT
<213> ORGANISM: Homo sapiens

<400> SEQUENCE: 21

Gly Asp Thr Arg Pro Arg Phe Leu Glu Glu Val Lys Phe Glu Cys His
1               5                   10                  15

Phe Phe Asn Gly Thr Glu Arg Val Arg Leu Leu Glu Arg Arg Val His
            20                  25                  30

Asn Gln Glu Glu Tyr Ala Arg Tyr Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Arg Arg Arg Ala Ala Val Asp Thr Tyr Cys Arg
65                  70                  75                  80

His Asn Tyr Gly Val Gly Glu Ser Phe Thr Val Gln Arg Arg Val Gln
                85                  90                  95

Pro Lys Val Thr Val Tyr Pro Ser Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Gly Gln Glu Glu Lys Thr Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Gln Ser Gly Glu Val Tyr Thr Cys Gln Val Glu
                165                 170                 175

His Pro Ser Val Met Ser Pro Leu Thr Val Glu Trp Arg Ala Arg Ser
            180                 185                 190

Glu Ser Ala Gln Ser Lys Met Leu Ser Gly Val Gly Gly Phe Val Leu
        195                 200                 205

Gly Leu Leu Phe Leu Gly Ala Gly Leu Phe Ile Tyr Phe Arg Asn Gln
    210                 215                 220

Lys Gly His Ser Gly Leu Pro Pro Thr Gly Phe Leu Ser
225                 230                 235


<210> SEQ ID NO 22
<211> LENGTH: 198
<212> TYPE: PRT
<213> ORGANISM: Homo sapiens

<400> SEQUENCE: 22

Gly Asp Thr Arg Pro Arg Phe Leu Trp Gln Leu Lys Phe Glu Cys His
```

```
1               5                   10                  15

Phe Phe Asn Gly Thr Glu Arg Val Arg Leu Leu Glu Arg Cys Ile Tyr
            20                  25                  30

Asn Gln Glu Glu Ser Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Arg Arg Ala Ala Val Asp Thr Tyr Cys Arg
65                  70                  75                  80

His Asn Tyr Gly Val Gly Glu Ser Phe Thr Val Gln Arg Arg Val Glu
                85                  90                  95

Pro Lys Val Thr Val Tyr Pro Ser Lys Thr Gln Pro Leu Gln His His
            100                 105                 110

Asn Leu Leu Val Cys Ser Val Ser Gly Phe Tyr Pro Gly Ser Ile Glu
        115                 120                 125

Val Arg Trp Phe Arg Asn Gly Gln Glu Glu Lys Ala Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Val Thr Ser Pro Leu Thr Val Glu Trp Arg Ala Arg Ser
            180                 185                 190

Glu Ser Ala Gln Ser Lys
        195


<210> SEQ ID NO 23
<211> LENGTH: 192
<212> TYPE: PRT
<213> ORGANISM: Homo sapiens

<400> SEQUENCE: 23

Gly Asp Thr Arg Pro Arg Phe Leu Glu Gln Val Lys His Glu Cys His
1               5                   10                  15

Phe Phe Asn Gly Thr Glu Arg Val Arg Phe Leu Asp Arg Tyr Phe Tyr
            20                  25                  30

His Gln Glu Glu Tyr Val Arg Phe Asp Ser Asp Val Gly Glu Tyr Arg
        35                  40                  45

Ala Val Thr Glu Leu Gly Arg Pro Asp Ala Glu Tyr Trp Asn Ser Gln
    50                  55                  60

Lys Asp Leu Leu Glu Gln Lys Arg Ala Ala Val Asp Thr Tyr Cys Arg
65                  70                  75                  80

His Asn Tyr Gly Val Gly Glu Ser Phe Thr Val Gln Arg Arg Val Tyr
                85                  90                  95

Pro Glu Val Thr Val Tyr Pro Ala Lys Thr Gln Pro Leu Gln His His
            100                 105                 110

Asn Leu Leu Val Cys Ser Val Asn Gly Phe Tyr Pro Gly Ser Ile Glu
        115                 120                 125

Val Arg Trp Phe Arg Asn Gly Gln Glu Glu Lys Thr Gly Val Val Ser
    130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Val Thr Ser Pro Leu Thr Val Glu Trp Arg Ala Arg Ser
```

```
            180                 185                 190


<210> SEQ ID NO 24
<211> LENGTH: 191
<212> TYPE: PRT
<213> ORGANISM: Homo sapiens

<400> SEQUENCE: 24

Thr Arg Pro Arg Phe Leu Trp Gln Pro Lys Arg Glu Cys His Phe Phe
1               5                   10                  15

Asn Gly Thr Glu Arg Val Arg Phe Leu Asp Arg Tyr Phe Tyr Asn Gln
            20                  25                  30

Glu Glu Ser Val Arg Phe Asp Ser Asp Val Gly Glu Phe Arg Ala Val
        35                  40                  45

Thr Glu Leu Gly Arg Pro Asp Ala Glu Tyr Trp Asn Ser Gln Lys Asp
    50                  55                  60

Ile Leu Glu Gln Ala Arg Ala Ala Val Asp Thr Tyr Cys Arg His Asn
65                  70                  75                  80

Tyr Gly Val Val Glu Ser Phe Thr Val Gln Arg Arg Val Gln Pro Lys
                85                  90                  95

Val Thr Val Tyr Pro Ser Lys Thr Gln Pro Leu Gln His His Asn Leu
            100                 105                 110

Leu Val Cys Ser Val Ser Gly Phe Tyr Pro Gly Ser Ile Glu Val Arg
        115                 120                 125

Trp Phe Leu Asn Gly Gln Glu Glu Lys Ala Gly Met Val Ser Thr Gly
    130                 135                 140

Leu Ile Gln Asn Gly Asp Trp Thr Phe Gln Thr Leu Val Met Leu Glu
145                 150                 155                 160

Thr Val Pro Arg Ser Gly Glu Val Tyr Thr Cys Gln Val Glu His Pro
                165                 170                 175

Ser Val Thr Ser Pro Leu Thr Val Glu Trp Arg Ala Arg Ser Glu
            180                 185                 190


<210> SEQ ID NO 25
<211> LENGTH: 187
<212> TYPE: PRT
<213> ORGANISM: Homo sapiens

<400> SEQUENCE: 25

Pro Arg Phe Leu Glu Tyr Ser Thr Ser Glu Cys His Phe Phe Asn Gly
1               5                   10                  15

Thr Glu Arg Val Arg Tyr Leu Asp Arg Tyr Phe His Asn Gln Glu Glu
            20                  25                  30

Asn Val Arg Phe Asp Ser Asp Val Gly Glu Phe Arg Ala Val Thr Glu
        35                  40                  45

Leu Gly Arg Pro Asp Ala Glu Tyr Trp Asn Ser Gln Lys Asp Leu Leu
    50                  55                  60

Glu Gln Lys Arg Gly Arg Val Asp Asn Tyr Cys Arg His Asn Tyr Gly
65                  70                  75                  80

Val Val Glu Ser Phe Thr Val Gln Arg Arg Val His Pro Lys Val Thr
                85                  90                  95

Val Tyr Pro Ser Lys Thr Gln Pro Leu Gln His His Asn Leu Leu Val
            100                 105                 110

Cys Ser Val Ser Gly Phe Tyr Pro Gly Ser Ile Glu Val Arg Trp Phe
        115                 120                 125

Arg Asn Gly Gln Glu Glu Lys Thr Gly Val Val Ser Thr Gly Leu Ile
    130                 135                 140
```

```
His Asn Gly Asp Trp Thr Phe Gln Thr Leu Val Met Leu Glu Thr Val
145                 150                 155                 160

Pro Arg Ser Gly Glu Val Tyr Thr Cys Gln Val Glu His Pro Ser Val
                165                 170                 175

Thr Ser Pro Leu Thr Val Glu Trp Arg Ala Arg
            180                 185


<210> SEQ ID NO 26
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Arg Asp Ser Arg Gly Lys Lys Val Ile Thr Ala Phe Asn Glu Gly Leu
1               5                   10                  15

Lys Gly Gly Gly Gly Ser Leu Val Gly Gly Gly Ser Gly Gly Gly Gly
            20                  25                  30

Ser Arg Pro Trp Phe Leu Glu Tyr Cys Lys Ser Glu Cys His Phe Tyr
        35                  40                  45

Asn Gly Thr Gln Arg Val Arg Leu Leu Val Arg Tyr Phe Tyr Asn Leu
    50                  55                  60

Glu Glu Asn Leu Arg Phe Asp Ser Asp Val Gly Glu Phe Arg Ala Val
65                  70                  75                  80

Thr Glu Leu Gly Arg Pro Asp Ala Glu Asn Trp Asn Ser Gln Pro Glu
                85                  90                  95

Phe Leu Glu Gln Lys Arg Ala Glu Val Asp Thr Val Cys Arg His Asn
            100                 105                 110

Tyr Glu Ile Phe Asp Asn Phe Leu Val Pro Arg Arg Val Glu Pro Thr
        115                 120                 125

Val Thr Val Tyr Pro Thr Lys Thr Gln Pro Leu Glu His His Asn Leu
    130                 135                 140

Leu Val Cys Ser Val Ser Asp Phe Tyr Pro Gly Asn Ile Glu Val Arg
145                 150                 155                 160

Trp Phe Arg Asn Gly Lys Glu Glu Lys Thr Gly Ile Val Ser Thr Gly
                165                 170                 175

Leu Val Arg Asn Gly Asp Trp Thr Phe Gln Thr Leu Val Met Leu Glu
            180                 185                 190

Thr Val Pro Gln Ser Gly Glu Val Tyr Thr Cys Gln Val Glu His Pro
        195                 200                 205

Ser Leu Thr Asp Pro Val Thr Val Glu Trp Lys Ala Gln Ser Thr Ser
    210                 215                 220

Ala Gln Asn Lys
225
```

SELECTIVE HIGH-AFFINITY POLYDENTATE LIGANDS AND METHODS OF MAKING SUCH

CROSS-REFERENCE TO RELATED APPLICATIONS

This application is a continuation of U.S. application Ser. No. 11/055,181, filed Feb. 9, 2005, now U.S. Pat. No. 7,662,785, which in turn claims benefit of and priority to U.S. Provisional Application Ser. No. 60/543,444, filed on Feb. 9, 2004, each of which is incorporated herein by reference in its entirety for all purposes.

STATEMENT AS TO RIGHTS TO INVENTIONS MADE UNDER FEDERALLY SPONSORED RESEARCH AND DEVELOPMENT

This work was supported in part by grants from the National Institutes of Health, National Cancer Institute Grant No: CA047829. In addition, pursuant to Contract No. W-7405-ENG-48 between the United States Department of Energy and the University of California for the operation of Lawrence Livermore National Laboratory, the Government of the United States of America has certain rights in this invention.

FIELD OF THE INVENTION

This invention pertains to the development of targeting molecules. More particularly this invention pertains to the development of polydentate selective high affinity ligands (SHALs) that can be used in a manner analogous to antibodies and/or peptide ligands for the diagnosis and treatment of various diseases (e.g., cancer).

BACKGROUND OF THE INVENTION

In general, it has been found that cancericidal drugs, such as chemotherapeutics, are also toxic to cells of normal tissues. Consequently, the side effects of such drugs can be almost as devastating to the patient as the malignant disease itself. The advent of monoclonal antibodies and peptide ligands provided a new means for improving drug specificity/selectivity. By conjugating, e.g., a cytotoxic agent to an antibody or peptide ligand directed against antigens present on malignant cells, but not present on normal cells, selective killing of malignant cells has been achieved. Many different immunoconjugates comprising an antibody attached to a cytotoxic agent have been created directed against a variety of cell-surface antigens.

Cytotoxic agents used in such immunoconjugates include radioisotopes, various plant and bacterial toxins (e.g. Pseudomonas exotoxin, diphtheria toxin, ricin, abrin, etc.), various growth factors, and more recently, agents such as caspases. Although there have been some successes, notably in lymphoma and leukemias, antibody-based therapy whether using antibodies alone or immunoconjugates, has generally not fulfilled the expected potential.

Although significant advances have been made in the treatment of malignant disease, curative regimens for most patients have not yet been developed or are associated with toxicities unattractive for the patient. Therefore, new strategies for the treatment of most malignant diseases are needed. These strategies should have as their goal, the maximization of therapeutic effect, coupled with the minimization of toxicity. One approach has involved the use of ligands specific for cell surface receptors or antibodies specific for malignant cell associated antigens as a means of targeting drugs or radioisotopes to the malignant cells. The approach is attractive for many malignant diseases because the malignant cells display a variety of tumor-restricted or upregulated antigens and/or receptors on their cell surfaces which would be available for targeting. Thus far, antibody/antigen systems have been found to be better than ligand receptor systems because they are more restricted than receptors and in greater abundance on the malignant cell.

Despite these advantages, antibodies have not fulfilled their potential for many reasons. Among the reasons, antibodies are macromolecules (large molecules) that often do not effectively access and penetrate the malignant tumor. In addition, antibodies are often large immunogenic molecules and can induce an immune response in the patient directed against the therapeutic agent. In addition, antibodies often do not show sufficient specificity for the target (e.g. cancer) tissue and thus are useful in only limited therapeutic regimen.

SUMMARY OF THE INVENTION

This invention provides novel polydentate selective high affinity ligands (SHALs) that can function to specifically bind particular target molecules in a manner analogous to antibody binding. Methods for the design and generation of SHALs for diagnosis and treatment of infectious and/or malignant diseases and their administration to patients with infectious and/or malignant diseases are described.

The SHALs typically comprise two or more ligands (binding moieties) that each bind different regions on the intended target attached to each other directly or through a linker. Where the SHAL is directed to a marker on a cancer cell, the SHAL associates in greater density (abundance) or accessibility on the target cell as compared to normal cells. The SHAL thus provides selectivity appropriate for diagnosis or treatment of the target cells. Different SHALs can be readily generated for different malignant cells and malignant diseases. The SHAL represents a core building block (e.g., a targeting moiety) that can be incorporated into larger e.g. chimeric molecules to affect specific delivery of an effector to the target.

Thus, in one embodiment, this invention provides a method of making a selective high-affinity polydentate ligand (SHAL) that specifically binds a target molecule. In certain embodiments, the method typically involves screening a first ligand library to identify a first ligand that binds to the target molecule; screening a second ligand library to identify a second ligand that binds to the target molecule where the second ligand is different than the first ligand; linking the first ligand to the second ligand to form a SHAL; and screening the SHAL for the ability to specifically bind to the target molecule. In certain embodiments the target molecule is a protein. In certain embodiments the target molecule is a cancer marker (e.g., Lym-1 epitope, Muc-1, C-myc, p53, Ki67, Her2, Her4, BRCA1, BRCA2, Lewis Y, CA 15-3, G250, HLA-DR cell surface antigen, CEA, CD20, CD22, integrin, cea, EGFr, AR, PSA, and other growth factor receptors, etc.). The method can optionally further involve screening the SHAL to identify a SHAL that binds to the target with an avidity and/or specificity higher than either ligand comprising the SHAL. The first ligand library and the second ligand library can be the same library or can be different libraries. In certain embodiments the first and/or second ligand library is a library of small organic molecules. In certain embodiments screening the first ligand library and/or screening the second ligand library comprises virtual in silico screening. The virtual in silico screening can comprise screening a compound database (e.g., MDL® Available Chemicals Directory) using one or more algorithms as utilized in the DOCK program. The virtual in silico screening can comprise screening a compound database using the DOCK program. The virtual in silico screening can involve screening for a first ligand and/or a second ligand that binds a pocket on a protein. In certain embodiments the pocket is identified using an algorithm utilized by the SPHGEN program. In certain embodiments the pocket is identified using the SPHGEN program. The virtual in silico screening can involve screening for a second ligand that binds different region of the target than the ligands identified when screening the first ligand library.

In certain embodiments screening a first ligand library and/or screening a second ligand library additionally comprises screening one or more ligands identified in the virtual in silico screening in a physical assay for the ability to bind to the target. Suitable physical assays include, but are not limited to a BIAcore assay, saturation transfer difference nuclear magnetic resonance spectroscopy, and transfer NOE (trNOE) nuclear magnetic resonance spectroscopy, ELISA, competitive assay, tissue binding assay, a live cell binding assay, a cellular extract assay, and the like.

Linking of the ligands can involve directly linking pairs of ligands or linking pairs of ligands with a linker (e.g., a PEG type linker, a peptide linker, an avidin/biotin linker, a straight chain carbon linker, a heterocyclic linker, a branched carbon linker, a dendrimer, a nucleic acid linker, a thiol linker, an ester linker, a linker comprising an amine, a linker comprising a carboxyl, etc.). The linking can optionally comprise linking pairs of ligands with linkers of different lengths to produce a library of SHALs having different length linkers; and, optionally, screening the library of SHALs having different length linkers to identify members of the library that have the highest avidity and/or specificity for the target.

This invention also provides a method of making a selective high-affinity polydentate ligand (SHAL) that specifically binds a target molecule (e.g., a nucleic acid, a protein, a receptor, a cancer marker, an intracellular target, etc.) by providing a target molecule; screening a library of potential ligands (e.g., proteins, nucleic acids, small organic molecules, metals, lectins, carbohydrates, sugars, etc.) to identify a plurality of ligands that bind to the target molecule thereby identifying a collection of binders; selecting a plurality of ligands from the collection of binders and screening them simultaneously against the target molecule whereby pairs of ligands that simultaneously bind to the target molecule are recognized as ligands that bind to different sites on the target molecule; selecting a pair of ligands that bind to different sites on the target molecule; and linking the pair of ligands with a linker to form a SHAL. In certain embodiments the pairs of ligands need not be screened simultaneously. In such instances the ligands are simply determined by any of a variety of methods to bind to different sites on the target such that both ligands are capable of simultaneously binding to the target. The method can optionally, further involve screening the SHAL for the ability to specifically bind the target molecule.

Linking of the ligands can involve directly linking pairs of ligands or linking pairs of ligands with a linker (e.g., a PEG type linker, a peptide linker, an avidin/biotin linker, a straight chain carbon linker, a heterocyclic linker, a branched carbon linker, a dendrimer, a nucleic acid linker, a thiol linker, an ester linker, a linker comprising an amine, a linker comprising a carboxyl, etc.). The linking can optionally comprise linking pairs of ligands with linkers of different lengths to produce a library of SHALs having different length linkers; and, optionally, screening the library of SHALs having different length linkers to identify members of the library that have the highest avidity and/or specificity for the target. In certain embodiments the method further involves comprising screening the SHAL(s) to identify a SHAL that binds to the target with an avidity and/or specificity higher than either ligand comprising the SHAL. The screening of individual ligands and/or bivalent or polyvalent SHAL(s) can be by any of a variety of methods including, but not limited to a BIAcore assay, saturation transfer difference nuclear magnetic resonance spectroscopy, and transfer NOE (trNOE) nuclear magnetic resonance spectroscopy, ELISA, competitive assay, tissue binding assay, live cell binding assay, a cellular extract assay, and the like. In certain embodiments the target molecule is a protein and/or a cancer marker (e.g., a Lym1 epitope, Muc-1, C-myc, p53, Ki67, Her2, Her4, BRCA1, BRCA2, Lewis Y, CA 15-3, G250, HLA-DR cell surface antigen, etc.).

Also provided is a method of synthesizing an inhibitor for an enzyme or other binding protein or receptor. In certain embodiments the method typically involves identifying a first pocket (or bump) and a second pocket (or bump) in the enzyme or other binding protein or receptor where the first and second pocket flank opposite sides of the active site or binding site of the enzyme or other binding protein or receptor; screening a first ligand library to identify a first ligand that binds to the first pocket (or bump); screening a second ligand library to identify a second ligand that binds to the second pocket (or bump); linking the first ligand to the second ligand to form a polydentate selective high affinity ligand (SHAL); and screening the SHAL for the ability to specifically bind to and inhibit the enzyme or other binding protein. In certain embodiments the two pockets or "bumps" need not be located on opposite sides of the active site or binding site of the enzyme or binding protein or receptor, but are simply located so that binding of the SHAL blocks binding of the native cognate ligand to that site. In certain embodiments the target molecule comprises a molecule selected from the group consisting of a protein, an enzyme, a nucleic acid, a nucleic acid binding protein, and a carbohydrate. In certain embodiments the method further involves screening the SHAL to identify a SHAL that binds to the target with an avidity and/or specificity higher than either ligand comprising the SHAL. The first ligand library and the second ligand library can be the same library or can be different libraries. In certain embodiments the first and/or second ligand library is a library of small organic molecules. In certain embodiments screening the first ligand library and/or screening the second ligand library comprises virtual in silico screening. The virtual in silico screening can comprise screening a compound database (e.g., MDL® Available Chemicals Directory) using one or more algorithms as utilized in the DOCK program. The virtual in silico screening can comprise screening a compound database using the DOCK program. The virtual in silico screening can involve screening for a first ligand and/or a second ligand that binds a pocket on a protein. In certain embodiments the pocket is identified using an algorithm utilized by the SPHGEN program. In certain embodiments the pocket is identified using the SPHGEN program. The virtual in silico screening can involve screening for a second ligand that binds different region of the target than the ligands identified when screening the first ligand library.

In certain embodiments screening a first ligand library and/or screening a second ligand library additionally comprises screening one or more ligands identified in the virtual in silico screening in a physical assay for the ability to bind to the target. Suitable physical assays include, but are not limited to a BIAcore assay, saturation transfer difference nuclear magnetic resonance spectroscopy, and transfer NOE (trNOE) nuclear magnetic resonance spectroscopy, ELISA, competitive assay, tissue binding assay, a live cell binding assay, a cellular extract assay, and the like.

Linking of the ligands can involve directly linking pairs of ligands or linking pairs of ligands with a linker (e.g., a PEG type linker, a peptide linker, an avidin/biotin linker, a straight chain carbon linker, a heterocyclic linker, a branched carbon linker, a dendrimer, a nucleic acid linker, a thiol linker, an ester linker, a linker comprising an amine, a linker comprising a carboxyl, etc.). The linking can optionally comprise linking pairs of ligands with linkers of different lengths to produce a library of SHALs having different length linkers; and, optionally, screening the library of SHALs having different length linkers to identify members of the library that have the highest avidity and/or specificity for the target.

This invention also provides a polydentate selective high affinity ligand (SHAL) that specifically binds to a desired target (e.g., a cancer cell). Where the target is a cancer cell, the SHAL typically comprises a first ligand that binds to a first site on a marker for the cancer cell linked (directly or through a linker) to a second ligand that binds to a second site on same marker or on a different marker for the cancer cell where the first site and the second site are different sites (e.g., both ligands are capable of simultaneously binding to the target(s)). In certain embodiments the first site and/or the second site is a pocket (or "bump") on the marker(s). Suitable markers include, but are not limited to a Lym-1 epitope, Muc-1, C-myc, p53, Ki67, Her2, Her4, BRCA1, BRCA2, Lewis Y, CA 15-3, G250, HLA-DR cell surface antigen, CEA, CD20, CD22, integrin, cea, EGFr, AR, PSA, other growth factor receptors, and the like.

In certain preferred embodiments, the marker is an HLA-DR cell surface antigen. In certain embodiments the first ligand and/or the second ligand bind sites within an epitope recognized by the Lym-1 antibody. In certain embodiments the first ligand and/or the second ligand is a small organic molecule. In certain embodiments the SHAL comprises a first ligand and/or a second ligand selected from Tables 2, 3, or 4. In certain embodiments the SHAL comprises a first ligand and/or a second ligand selected from Table 4. The first ligand can be joined directly to the second ligand or the first ligand can be attached to the second ligand by a linker (e.g., a PEG type linker, a peptide linker, an avidin/biotin linker, a straight chain carbon linker, a heterocyclic linker, a branched carbon linker, a dendrimer, a nucleic acid linker, a thiol linker, an ester linker, a linker comprising an amine, a linker comprising a carboxyl, etc.). In certain embodiments the SHAL has an avidity for the marker greater than about $10^{-8}$ M while the individual ligands comprising the SHAL each have a binding affinity for the marker less than about $10^{-6}$ M. In certain embodiments the SHAL has a formula as shown herein and in the Figures or is an analogue thereof.

This invention also provides chimeric molecules comprising a SHAL as described herein attached to an effector (e.g., an epitope tag, a second SHAL, an antibody, a label, a cytotoxin, a liposome, a radionuclide, a drug, a prodrug, a viral particle, a cytokine, and a chelate. In certain embodiments the effector is an epitope tag selected from the group consisting of an avidin, and a biotin. In certain embodiments the effector is a cytotoxin selected from the group consisting of a Diphtheria toxin, a *Pseudomonas* exotoxin, a ricin, an abrin, and a thymidine kinase. In certain embodiments the effector is a chelate comprising a metal isotope selected from the group consisting of $^{99}$Tc, $^{203}$Pb, $^{67}$Ga, $^{68}$Ga, $^{72}$As, $^{111}$In, $^{113m97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain embodiments effector is a chelate comprising an alpha emitter (e.g., bismuth 213). In certain embodiments the effector is a chelate comprising DOTA. In certain embodiments the effector is a lipid or a liposome (e.g. a liposome containing a drug).

In still another embodiment, this invention provides a pharmaceutical formulation the formulation comprising a polydentate selective high affinity ligand (SHAL) that specifically binds to a cancer cell as described herein and a pharmaceutically acceptable excipient. In certain embodiments the formulation can be provided as a unit dosage formulation. In certain embodiments the formulation can be provided as a time-release formulation.

This invention also provides a pharmaceutical formulation the formulation comprising a pharmaceutically acceptable excipient and a chimeric molecule comprising a SHAL as described herein. In certain embodiments the formulation can be provided as a unit dosage formulation. In certain embodiments the formulation can be provided as a time-release formulation.

Methods are provided for inhibiting the growth or proliferation of a cancer cell. The methods typically involves contacting the cancer cell (e.g., metastatic cell, tumor cell, etc.) with a polydentate selective high affinity ligand (SHAL) that specifically binds to a cancer cell and/or with a chimeric molecule comprising a polydentate selective high affinity ligand (SHAL) that specifically binds to a cancer cell attached to an effector (e.g., drug, liposome, cytotoxin, radionuclide, or chelator).

In certain embodiments, this invention provides SHALs that specifically bind to a desired target. The target can be any target for which it is desired to create a binding moiety. The SHAL typically comprises two or more ligands joined directly or through a linker where a first ligand that binds to a first site on the target and the second ligand binds to second site on the target on same target marker where the first site and the second site are different sites (e.g., both ligands are capable of simultaneously binding to the target(s)). In certain embodiments the first site and/or the second site is a pocket (or "bump") on the target(s). In certain embodiments the first site and the second site are on the same target molecule.

This invention also provides various detection methods. In certain embodiments this invention provides a method of detecting a cancer cell. The method typically involves contacting the cancer cell with a chimeric molecule comprising a SHAL that specifically binds to a cancer cell (e.g. to a cancer marker) attached to a detectable label (e.g., gamma-emitter, a positron-emitter, an x-ray emitter, an alpha emitter, a fluorescence-emitter, etc.) and detecting the presence or absence of the detectable label. In certain embodiments the method typically involves contacting a cancer cell with a chimeric molecule comprising chimeric molecule comprising SHAL that specifically binds to a cancer cell (e.g. to a cancer marker) attached to an epitope tag; contacting the chimeric molecule with a chelate comprising a detectable moiety whereby the chelate binds to the epitope tag thereby associating the detectable moiety with the chelate; and detecting the detectable moiety. In certain embodiments the detectable moiety is a radionuclide (e.g., a gamma-emitter, a positron-emitter, an alpha emitter, an x-ray emitter, etc.). In certain embodiments the detecting comprises external imaging and/or internal imaging. In certain embodiments the detectable moiety comprises a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64l}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. In certain embodiments the chelate comprises DOTA. In certain embodiments the epitope tag is an avidin or a biotin.

This invention also contemplates kits for creating and/or using SHALs of this invention and/or chimeric molecules comprising SHALs of this invention. In certain embodiments the kit comprises a container containing a SHAL as described herein and/or containers containing ligands for assembly into a SHAL as described herein. The like can optionally further include one or more linkers, one or more effectors (chelates, radionuclides, etc.), and the like. In certain embodiments the SHAL is in a pharmacologically acceptable excipient.

In certain embodiments, this invention expressly excludes SHALs where the binding moieties comprising the SHAL are antibodies, single chain antibodies, and the like. In certain embodiments the SHALs are not polyvalent antibodies or polyvalent single chain antibodies. In certain embodiments the ligands comprising the SHALs are not proteins. In certain embodiments, this invention expressly excludes SHALs where the binding moieties comprising the SHAL preferentially and/or specifically bind nucleic acids. In certain embodiments the ligands comprising the SHALs are small organic molecules.

Definitions

The terms "specific binding" or "preferential binding" refer to that binding which occurs between such paired species as enzyme/substrate, receptor/agonist, antibody/antigen, and lectin/carbohydrate which may be mediated by covalent and/or non-covalent interactions. When the interaction of the two species typically produces a non-covalently bound complex, the binding which occurs is typically electrostatic, and/or hydrogen-bonding, and/or the result of lipophilic interactions. Accordingly, "specific binding" occurs between pairs of species where there is interaction between the two that produces a bound complex. In particular, the specific binding is characterized by the preferential binding of one member of a pair to a particular species as compared to the binding of that member of the pair to other species within the family of compounds to which that species belongs. Thus, for example, a ligand may show an affinity for a particular pocket on a HLA-DR10 molecule that is at least two-fold preferably at least 10 fold, more preferably at least 100 fold, at least 1000 fold, or at least 10000 fold greater than its affinity for a different pocket on the same or related proteins.

The terms "ligand" or "binding moiety", as used herein, refers generally to a molecule that binds to a particular target molecule and forms a bound complex as described above. The binding can be highly specific binding, however, in certain embodiments, the binding of an individual ligand to the target molecule can be with relatively low affinity and/or specificity. The ligand and its corresponding target molecule form a specific binding pair. Examples include, but are not limited to small organic molecules, sugars, lectins, nucleic acids, proteins, antibodies, cytokines, receptor proteins, growth factors, nucleic acid binding proteins and the like which specifically bind desired target molecules, target collections of molecules, target receptors, target cells, and the like.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term "ligand library" refers to a collection (e.g. to a plurality) of ligands or potential ligands. The ligand library can be an actual physical library of ligands and/or a database (e.g. compound database comprising descriptions of a plurality of potential ligands, e.g. the MDL® Available Chemicals Directory, and the like.

The term "SHAL" refers to a molecule comprising a plurality of ligands that each bind to a different region of the target molecule to which the SHAL is directed. The ligands are joined together either directly or through a linker to form a polydentate moiety that typically shows high avidity for the target molecule. In certain embodiments, the SHAL comprises two or more ligands that bind their target with low affinity (e.g. $<10^{-6}$M and/or dissociates within seconds or less) that, when coupled together, form a SHAL that binds the target with high affinity (e.g., $>10^{-8}$ M and/or dissociates slowly, e.g. hours to days).

The term "polydentate' when used with respect to a SHAL indicates that the SHAL comprises two or more ligands. The ligands typically bind to different parts of the target to which the SHAL is directed.

The terms "bidentate", "tridentate", and so forth when used with respect to a SHAL refer to SHALs consisting of two ligands, SHALs consisting of three ligands, and so forth.

The term "polyvalent SHAL" refers to a molecule in which two or more SHALs (e.g. two or more bidentate SHALs) are joined together. Thus, for example a bivalent SHAL refers to a molecule in which two SHALs are joined together. A trivalent SHAL refers to a molecule in which three SHALs are joined together, and so forth. A bivalent version of the bidentate SHAL JP459B is illustrated in FIG. 14).

A "polyspecific SHAL" is 2 or more SHALs joined together where each SHAL is polydentate and either or both can be polyvalent synthesized (or otherwise generated) so that they have 2 or more targets for each SHAL (set of poly ligands). For example, a SHAL can be synthesized with two or more ligands for the cavities of HLA-DR and cavities on a CDXX, eg CD20 or CD22, or all 3, etc. Another example involves joining a MUC-1 SHAL and an antilymphoma SHAL because some lymphomas overexpress traditional HLA-DR and CD receptors and MUC-1(upregulated). SHAL synthesized with 2 or more ligands for the cavities of HLA-DR and cavities for a chelate, e.g DOTA, etc. where in the univalent or bivalent SHAL targets the malignant cell and the univalent or bivalent 2nd module catches a subsequently delivered agent, e.g. DOTA chelated radiometal or a prodrug intended to activate the drug transported to the malignant cell by the 1st SHAL.

The term "virtual in silico" when used, e.g. with respect to screening methods refers to methods that are performed without actual physical screening of the subject moieties. Typically virtual in silico screening is accomplished computationally, e.g. utilizing models of the particular molecules of interest. In certain embodiments, the virtual methods can be performed using physical models of the subject molecules and/or by simple visual inspection and manipulation.

The phrase "target for a SHAL" refers to the moiety that is to be specifically bound by the bidentate or polydentate SHAL.

The phrase "an algorithm found in . . . ", e.g. "an algorithm found in SPHGEN" refers to an algorithm that is implemented by (found in) the referenced software. The algorithm, however, can be manually, or by a program other than the referenced software and still represent a use of an algorithm found in the referenced software.

The term "pocket" when referring to a pocket in a protein refers to a cavity, indentation or depression in the surface of the protein molecule that is created as a result of the folding of the peptide chain into the 3-dimensional structure that makes the protein functional. A pocket can readily be recognized by inspection of the protein structure and/or by using commercially available modeling software (e.g. DOCK).

The term "cancer markers" refers to biomolecules such as proteins that are useful in the diagnosis and prognosis of cancer. As used herein, "cancer markers" include but are not limited to: PSA, human chorionic gonadotropin, alpha-fetoprotein, carcinoembryonic antigen, cancer antigen (CA) 125, CA 15-3, CD20, CDH13, CD31, CD34, CD105, CD146, D16S422HER-2, phosphatidylinositol 3-kinase (PI 3-kinase), trypsin, trypsin-1 complexed with alpha(1)-antitrypsin, estrogen receptor, progesterone receptor, c-erbB-2, bcl-2, S-phase fraction (SPF), p185erbB-2, low-affinity insulin like growth factor-binding protein, urinary tissue factor, vascular endothelial growth factor, epidermal growth factor, epidermal growth factor receptor, apoptosis proteins (p53, Ki67), factor VIII, adhesion proteins (CD-44, sialyl-TN, blood group A, bacterial lacZ, human placental alkaline phosphatase (ALP), alpha-difluoromethylornithine (DFMO), thymidine phosphorylase (dTHdPase), thrombomodulin, laminin receptor, fibronectin, anticyclins, anticyclin A, B, or E, proliferation associated nuclear antigen, lectin UEA-1, cea, 16, and von Willebrand's factor.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10):1925) and references therein; Letsinger (1970) *J. Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J. Am. Chem. Soc.* 110: 4470; and Pauwels et al. (1986) *Chemica Scripta* 26: 1419), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111 :2321, O-methylphophoroamidite linkages (see Eckstein, *Oligonucleotides and Analogues: A Practical Approach*, Oxford University Press), and peptide nucleic acid backbones and linkages (see Egholm (1992) *J. Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995), *Chem. Soc. Rev. pp* 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

The term "biotin" refers to biotin and modified biotins or biotin analogues that are capable of binding avidin or various avidin analogues. "Biotin", can be, inter alia, modified by the addition of one or more addends, usually through its free carboxyl residue. Useful biotin derivatives include, but are not limited to, active esters, amines, hydrazides and thiol groups that are coupled with a complimentary reactive group such as an amine, an acyl or alkyl group, a carbonyl group, an alkyl halide or a Michael-type acceptor on the appended compound or polymer.

Avidin, typically found in egg whites, has a very high binding affinity for biotin, which is a B-complex vitamin (Wilcheck et al. (1988) *Anal. Biochem,* 171: 1). Streptavidin, derived from *Streptomyces avidinii*, is similar to avidin, but has lower non-specific tissue binding, and therefore often is used in place of avidin. As used herein "avidin" includes all of its biological forms either in their natural states or in their modified forms. Modified forms of avidin which have been treated to remove the protein's carbohydrate residues ("deglycosylated avidin"), and/or its highly basic charge ("neutral avidin"), for example, also are useful in the invention.

The term "residue" as used herein refers to natural, synthetic, or modified amino acids.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$l by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA,* 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage or yeast (e.g., scFv, Fv, Fab and disulfide linked Fv (Reiter et al. (1995) *Protein Eng.* 8: 1323-1331).

The term "specifically binds", as used herein, when referring to a SHAL or to a biomolecule (e.g., protein, nucleic acid, antibody, etc.), refers to a binding reaction that is determinative of the presence of the SHAL or biomolecule in a heterogeneous population of molecules (e.g., proteins and other biologics). Thus, under designated conditions (e.g. binding assay conditions in the case of a SHAL or stringent hybridization conditions in the case of a nucleic acid), the specified ligand or SHAL preferentially binds to its particular "target" molecule and preferentially does not bind in a significant amount to other molecules present in the sample.

An "effector" refers to any molecule or combination of molecules whose activity it is desired to deliver/into and/or localize at a target (e.g. at a cell displaying a characteristic marker). Effectors include, but are not limited to labels, cytotoxins, enzymes, growth factors, transcription factors, drugs, lipids, liposomes, etc.

A "reporter" is an effector that provides a detectable signal (e.g. is a detectable label). In certain embodiments, the reporter need not provide the detectable signal itself, but can simply provide a moiety that subsequently can bind to a detectable label.

The term "conservative substitution" is used in reference to proteins or peptides to reflect amino acid substitutions that do not substantially alter the activity (specificity or binding affinity) of the molecule. Typically, conservative amino acid substitutions involve substitution of one amino acid for another amino acid with similar chemical properties (e.g. charge or hydrophobicity). The following six groups each contain amino acids that are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

The terms "epitope tag" or "affinity tag" are used interchangeably herein, and usually refers to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g. ligands bound by receptors), ligands bound by other ligands to form heterodimers or homodimers, $His_6$ (SEQ ID NO:14) bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK (SEQ ID NO:1) epitope, c-myc antibodies (available from Sigma, St. Louis), the HNK-1 carbohydrate epitope, the HA epitope, the HSV epitope, the $His_4$ (SEQ ID NO:15), $His_5$ (SEQ ID NO:16), and $His_6$ (SEQ ID NO:14) epitopes that are recognized by the His epitope specific antibodies (see, e.g., Qiagen), and the like. In addition, vectors for epitope tagging proteins are commercially available. Thus, for example, the pCMV-Tag1 vector is an epitope tagging vector designed for gene expression in mammalian cells. A target gene inserted into the pCMV-Tag1 vector can be tagged with the FLAG® epitope (N-terminal, C-terminal or internal tagging), the c-myc epitope (C-terminal) or both the FLAG (N-terminal) and c-myc (C-terminal) epitopes.

A PEG type linker refers to a linker comprising a polyethylene glycol (PEG).

BRIEF DESCRIPTION OF THE DRAWINGS

FIG. 4A illustrates the organization of normal MUC-1. Abnormal MUC1, also a good target, is less glycosylated, has an exposed VNTR, and a tandem repeat unit: 20 aa GVTSAPDTRPAPGSTAPPAH (SEQ ID NO:2).

FIG. 8 illustrates the amino acid sequence alignment of HLA-DR molecules with known crystal structures. PDB codes identify the HLA-DR1(1aqd) (SEQ ID NO:22), HLA-DR2(1bx2) (SEQ ID NO:24), HLA-DR3(1a6a) (SEQ ID NO:25) and HLA-DR4 molecules (1dm5) (SEQ ID NO:23) sequences ("HLA-DR10" is disclosed as SEQ ID NO:21). 1i3r (SEQ ID NO:26) is a homologous MHC fusion protein.

FIGS. 13A and 13B illustrate bidentate SHALs synthesized by combining the appropriate pairs of the individual ligands identified to bind to HLA-DR10. FIG. 13A illustrates the three molecules. FIG. 13B illustrates two SHALs, synthesized by linking together deoxycholate and 5-leu-enkephalin, that have been shown to bind to isolated HLA-DR10 with nM affinities. The red part is one ligand (deoxycholate), the green is the other ligand (e.g, 5-leu-enkephalin), the blue is a lysine used to make the shortest linker, and the black is a combination of things: the PEG molecules used to make the linker between the two ligands longer, and a biotin molecule attached to the SHALs for testing purposes.

FIG. 17A illustrates increased binding of SHAL JP459B and Lym-1 MAb on large cell lymphoma compared to small cell lymphoma (panels A-D) and selective binding of live Raji cells (crystal violet stained) but not other cell types on plates coated with streptavidin horse radish peroxidase (SHRP) and biotinylated SHAL (panels E-H). (panels A-D) The SHAL was preincubated with SAHRP and detected by DAB reagent. Lym-1 binding was detected with a biotinylated anti-mouse MAb, followed by SAHRP and DAB. Panel A) SHAL on large cell lymphoma Panel B) SHAL on small cell lymphoma Panel C) Lym-1 MAb on large cell lymphoma and Panel D) Lym-1 MAb on small cell lymphoma. (Panels E-H) Images show selective binding of SHAL JP459B to live Raji cells (Panel E), but not to non-lymphoma LnCAP (Panel F), 22RV (Panel G) or DU145 (Panel H) cell lines. FIG. 17B shows that SHAL JP459B binds only to live-cultured tumor cells containing HLA-DR10, the plates are coated with steptavidin over night, they are washed and then the SHAL is added and incubated for 2 hrs and then the plates are washed again to remove unbound SHAL. Then the cells are added. The cells were washed and stained by Cresyl Violet.

FIG. 23 shows formulas for JP7001.2 and triiodothyronine-deoxycholate SHALs.

DETAILED DESCRIPTION

Figure 1:
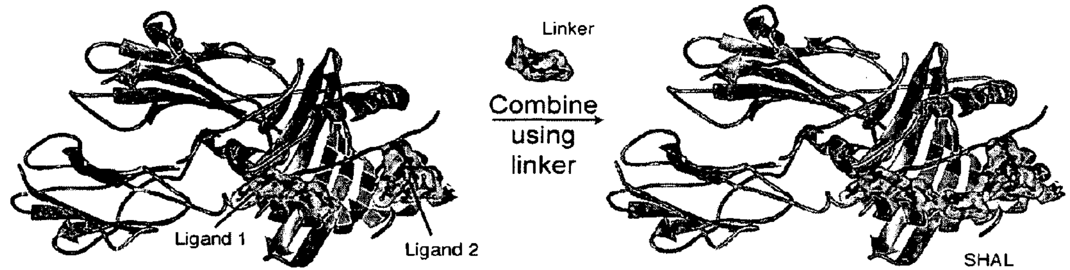
FIG. 1 illustrates a method of creating SHALs by identifying individual ligands (blue) that bind to two unique sites on the surface of a target (e.g., HLA-DR10 encompassing the Lym-1 epitope (red, green, yellow amino acids)) and linking them together synthetically to produce a molecule that binds to both sites.

This invention pertains to the development of a new class of binding molecules that can be used to specifically bind just about any target molecule(s). This class of binding molecules are referred to herein as Selective High Affinity Ligands or "SHALs". The SHALs can be used in a manner analogous to antibodies in a wide variety of contexts that include, but are not limited to capture reagents in affinity columns for purification of biological or other materials, binding agents in biosensors, agents for the assembly of nanoparticles or nanomachines, diagnostics, and therapeutics.

SHALs can also be used to detect molecular signatures that can distinguish between various pathogen types or strains. SHALs also have use in biodefense applications for the detection of unique protein signatures present in toxins and on the surfaces of pathogenic organisms and to distinguish these biothreat agents from naturally occurring non-hazardous materials. Because the SHALs can be relatively stable when exposed to the environment, they are particular well suited for use in biosensors for biodefense, diagnostic, and other applications.

In certain preferred embodiments, the SHALs are used in the diagnosis and/or treatment of cancers. In such embodiments, the SHALs are directed to unique and/or specific sites (e.g. cancer-specific markers) on the surfaces of cancers (e.g., various malignant cells).

In certain embodiments, the SHALs can have a therapeutic effect when administered per se (e.g., in a manner analogous to the antibody therapeutic Herceptin™). A SHAL, like an antibody, can have a direct effect on a malignant cell that leads to cell death because the SHAL serves as an agonist against a normal pathway, thereby initiating or blocking critical cell functions and leading to malignant cell death. A SHAL can also act as a vaccine because it provides malignant cell identification either because it represents an aberrant cell surface marker or enhances a usual malignant cell marker.

In addition, or alternatively, the SHAL(s) can be used as targets (when bound to the targeted cell), or as carriers (targeting moieties) for other effectors that include, but are not limited to agents such as cytotoxic agents, markers for identification by the immune system, detectable labels (for imaging), and the like.

Radioisotopes are attractive examples of cytotoxic effectors that can be attached to the carrier SHAL to selectively deliver radiotherapy to the malignant cell(s). This therapy can be administered as single agent therapy, or in combination with marrow reconstitution in order to achieve greater dose intensity, or other drugs that may enhance the radiation effects on the malignant disease. Although there are many different drugs, chemotherapeutic, biological and otherwise, that can be combined with the SHAL, taxanes are one attractive example.

Examples of cytotoxic agents include radioisotopes, immunotoxins, chemotherapeutics, biologicals, etc. Interesting examples include apoptotic signals and enzymes such as the caspases. Radioisotopes represent interesting cytotoxic agents that have been shown to be effective in conjunction with antibody antigen and ligand-receptor systems. For treatment purposes, according to the present invention, it is considered that, in some embodiments, labeling with a particle emitter such as beta−, beta+ (positron) are preferable. In some cases, labeling with an alpha emitter or Auger-electron emitter is appropriate. There are many examples of therapeutic radioisotopes including yttrium-90 or iodine-131 that are of considerable current interest.

For certain imaging purposes, according to the present invention, it is considered that technetium-99, indium-111, iodine-123, or iodine-131 are attractive for single photon imaging and that beta+ (positron) emitters such as copper-64, yttrium-86, gallium-68, etc. are particularly likely to be very attractive when attached to a SHAL for diagnostic purposes A SHAL consists of two or more ligands (also referred to as binding moieties) linked together directly or through a linker to generate a core "polydentate" molecule (SHAL) that has been designed to specifically bind to essentially any desired target (e.g., unique or specific sites (pockets) on an intended target malignant cell surface molecule). The ligands (binding moieties) comprising the SHAL can include essentially any moiety capable of binding a site on the target. Such binding moieties can include, but are not limited to various chemicals (e.g. small organic molecules), proteins, sugars, carbohydrates, lectins, lipids, metals, nucleic acids, peptide and nucleic acid analogues, and the like.

Although not required, the individual ligands comprising the SHAL often have relatively low affinity (e.g., less than about $10^{-6}$ M) for the target. In contrast, the polydentate SHAL (comprising a plurality of ligands) typically shows relatively high avidity (e.g., greater than about $10^{-8}$ M, preferably greater than about $10^{-9}$ or $10^{-10}$ M, still greater than about $10^{-11}$ M, and most preferably greater than about $10^{-12}$ M).

In certain embodiments, where the target to which the SHAL is to be directed is a protein, the ligands comprising the SHAL can be selected to bind certain non-functional sites on the protein. A protein often has a number (few to >50) of "pockets" or cavities distributed across its surface. These cavities are produced as the protein chain is folded into a three dimensional structure to make the protein functional. This observation makes it possible to consider designing SHALs that exhibit much greater binding specificity for a given protein than previously possible. By linking together two moieties that bind to unique pockets on the surface of a protein with only micromolar affinities, it is possible to design polydentate molecules (SHALs) that bind with nanomolar to picomolar affinities and are highly selective and do not cross react with other functionally related molecules. For proteins with a known or predicted structure, computational methods can be used to generate a three-dimensional map of the molecular surface and identify suitable sized pockets that are structurally unique for that protein as described herein.

Databases containing the structures of known small molecules can be screened for their ability to bind into pockets on the target protein using a "docking" program. The top candidates can then be tested using a variety of experimental techniques as described herein to identify the molecules that actually bind to the protein as well as those that bind to the correct site. Pairs of the ligands (one from each set) can then be attached to opposite ends of an appropriate length linker using solid or solution phase chemistry to generate bidentate SHALs (FIG. 1). The highest affinity and most selective SHALs can then be identified by conducting conventional binding studies.

While it might at first seem counter-intuitive that linking together two small ligands that bind weakly to target (e.g., a protein) and exhibit little or insufficient selectivity can result in the production of a molecule that binds to its intended target (e.g., target protein) three to six or more orders of magnitude more tightly and with high selectivity, this result has been demonstrated repeatedly.

Without being bound to a particular theory, it is believed that while the presence of two or more ligands in the SHAL would be expected to increase the odds that the molecule might bind to a wider variety of proteins, we have observed that this non-specific binding is weak (approximately the same as the free ligand) and those molecules attached to non-target proteins via only one of the ligands will not remain bound long. The enhanced affinity and selectivity observed when both ligands in a bidentate SHAL or all the ligands comprising a polydentate SHAL bind to their respective targets (e.g. pockets on a target protein) is derived from three factors that relate to the nature of the SHAL-target interaction: First, the presence of the linker prevents the individual ligands comprising the SHAL that dissociate from their target from diffusing away from the target surface, increasing significantly the rate at which the free ligand rebinds. Second, the reduced off rate of release of the bidentate or polydentate SHAL is dictated by the fact that the probability that both (or all) ligands comprising the SHAL will simultaneously release from their target is substantially lower than the probability that either one will release. The spacing between the ligands comprising the SHAL which is determined by the attachment chemistry (e.g. the linker), allows the ligands comprising the SHAL to bind simultaneously to their target only if the ligands are separated by the correct distance. If either ligand in the SHAL binds independently to another target, its low affinity (1-10 micromolar affinity is typical for the ligands we identify) would result in the ligand falling off rapidly (the off-rate would be high). Thus the only situation in which the bidentate or polydentate SHAL would bind tightly to the intended target (nanomolar affinity or higher) would be when both ligands comprising the SHAL bind simultaneously to the target molecule (e.g. target protein). Once both or all ligands are bound, the off-rate of the entire molecule (the SHAL) would be reduced dramatically. If the ligand binding sites are selected properly (e.g. by targeting regions that vary in amino acid sequence or structure in the case of a protein target), it becomes highly improbable that identical sites will be found on another target separated by the same distance. If this extremely unlikely event were to occur, an additional ligand binding site (e.g., a third binding site adjacent to Site 1 and Site 2) can be identified, and an additional ligand can be incorporated into the SHAL (e.g. to create a tridentate, quadridentate, etc. SHAL).

SHALs have certain advantages over antibodies, particularly in therapeutic and/or diagnostic applications. Typically SHALs are considerably smaller than antibodies. They are consequently able to achieve greater tumor penetration. In certain embodiments, they are also able to cross the blood brain barrier, e.g., for the treatment of brain tumors. It is believed that the SHALs are also often less immunogenic than antibodies, and are often cleared from the circulation more rapidly.

The SHALs of this invention are typically polydentate, i.e., the SHAL comprises two or more ligands, that are joined together directly or through one or more linkers. In certain embodiments the ligands bind to different parts of the target (e.g., different epitopes on a single protein) to which the SHAL is directed. In certain embodiments the ligands bind to different molecules, e.g. different cancer markers on a cancer cell, different proteins comprising a receptor, and the like. In certain embodiments polyspecific SHALs can be used for crosslinking the same or different antigens on the same cell thereby enhancing the signal transduction, or for pretargeting, e.g., where one SHAL is designed to target malignant cells and is attached to other SHALs designed to "catch" a subsequently administered carrier of a cytotoxic agent (e.g., chelated radiometal, etc), to recruit an immunologically active cell (e.g., macrophage, T-cell, etc.) to the site, to activate a prodrug on the targeted SHAL, and so forth.

In certain embodiments this "multiple specificity" is achieved by the use of polyvalent SHALs. Polyvalent SHALs are molecules in which two or more SHALs (e.g., two or more bidentate SHALs) are joined together. The different SHALs comprising the polyvalent SHAL can be directed to the same or different targets, e.g. as described above.

I. Construction of SHALs.

SHALs of this invention are created by identifying ligands (binding moieties) that bind, and in some embodiments, that specifically (or preferentially) bind, different regions of the target molecule or molecules. Ligands binding different regions of the target molecules are then joined directly or through a linker to produce a bidentate SHAL comprising two different binding moieties or a polydentate SHAL comprising two or more different biding moieties. The SHAL can then be screened for its ability to bind the intended target.

The initial identification of ligands that bind different regions of the target can be accomplished using virtual in silico methods (e.g. computational methods) and/or empirical methods, e.g. as described herein.

Once two or more suitable ligands (binding moieties) are identified they can, optionally be screened (validated) for the ability to bind the target at different sites. Suitable binding ligands can then be coupled together directly or through a linker to form a bidentate or polydentate SHAL that can then, optionally, be screened for the ability to bind the target.

A) Target Selection.

Figure 21:
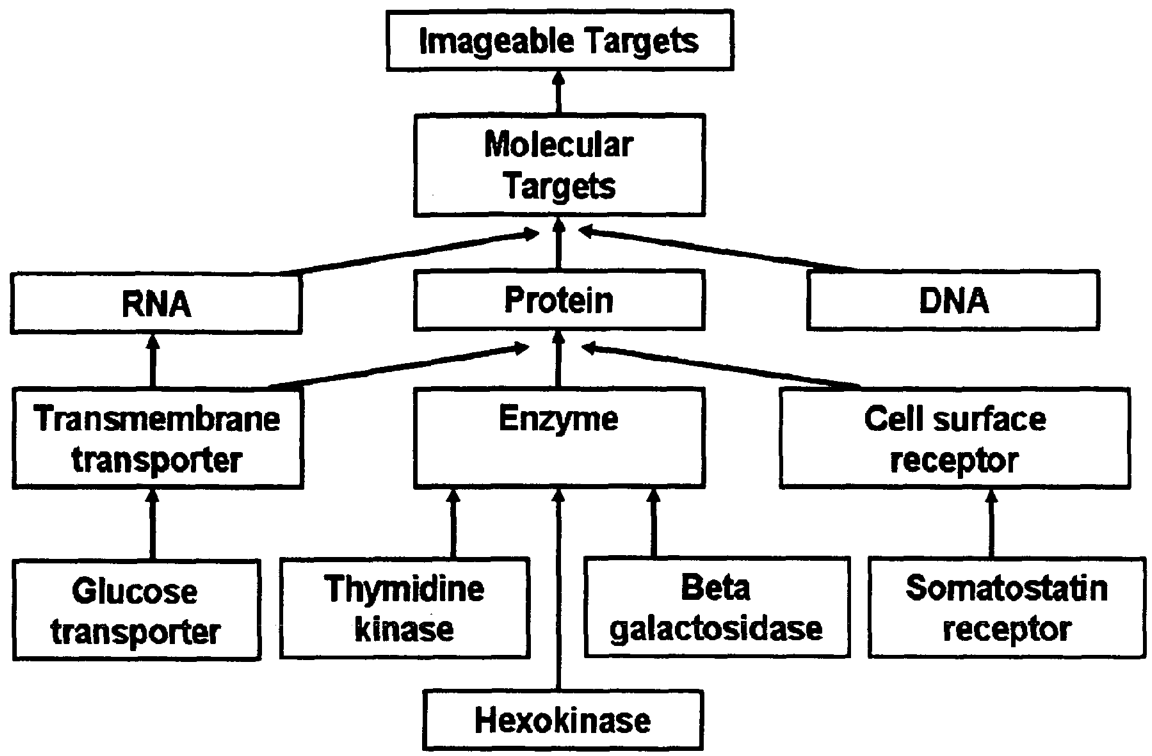
FIG. 21 illustrates various classes of SHAL targets.

Virtually any molecule, receptor, combination of molecules can serve as a target for a SHAL (see, e.g., FIG. 21). Target selection is determined by the application for which the SHAL is intended. Thus, for example, where the SHAL is to be incorporated into an affinity column (e.g. to purify a protein or nucleic acid) the target is the molecule (e.g. protein, nucleic acid, etc.) that is to be purified using the affinity column comprising the SHAL.

Where the SHAL is to be used in the treatment and/or diagnosis of a cancer, the target is typically a molecule, collection of molecules, receptor, enzyme, or other structure that is characteristic of the cancer (e.g. that permits the SHAL to preferentially bind to the cancer cell as compared to a normal healthy cell).

A number of cancer-specific markers are known to those of skill in the art. Such markers include, but are not limited to Lym-1 epitope, Muc-1, C-myc, p53, Ki67, erbB-2, Her2, Her4, BRCA1, BRCA2, Lewis Y, CA 15-3, G250, HLA-DR cell surface antigen, CEA, CD2, CD3, CD7, CD19, CD20, CD22, integrin, EGFr, AR, PSA, carcinoembryonic antigen (CEA), the L6 cell surface antigen (see, e.g., Tuscano et al. (2003) *Neoplasia,* 3641-3647; Howell et al. (1995) *Int J Biol Markers* 10:126-135; Marken et al. (1992) *Proc. Natl. Acad. Sci. U.S.A.* 89: 3503-3507, 1992), growth factor receptors, and/or various intracellular targets (e.g. receptors, nucleic acids, phosphokinases, etc.) and the like.

In certain embodiments, SHALs can be generated for cell surface membrane target proteins that influence intracellular functions, thereby promoting these functions (agonist) or inhibiting these functions (antagonist) by blocking other molecular binding or causing an inhibitory or enhanced intracellular signal, e.g, phosphokinase signaling. SHALs can be generated for cell surface membrane target proteins such as antigens and antibodies that can be internalized into the cell. In common with antibodies that target internalizing antigens and peptide ligands that target internalizing receptors, these SHALs will be internalized and in the cell where they can have agonist or antagonist effects on critical cell functions such as protooncogenes, phosphokinases, lysosomes and DNA/RNA/mRNA because of their agonist or antagonist functions or because they deliver a toxin or radioisotope payload. There are several advantages of SHALs over antibodies and peptide ligands. They include small size and the range of charge that can be used to permit free movement into and within the cell when an intracellular molecule is the primary target.

SHALs can be used to preferentially select specific cells by their membrane targets and, upon dissociation from the targeted cell surface membrane may freely move across the cell surface membrane to access the inside of the cell. The SHAL can be made multi-specific so that when it is internalized, or when it dissociates and penetrates the cell surface membrane, the second specificity can permit targeting of internal cell molecules such as phosphokinases, lysosomal enzymes, hormone receptors, gene and proto oncogene protein products, DNA/RNA/mRNA, and the like. In certain embodiments, uni-specific but multivalent SHALs can be generated that both target cell surface molecules and cross-link these molecules leading to enhanced biologic effects that have been described for cross-linked antibody—antigen systems.

In contrast to antibodies and peptide ligands that typically cannot directly and readily penetrate cell surface membranes, because of the small size of SHALs, and the ability to select the hydrophobic or hydrophilic character of the SHAL, SHALs can be produced that are capable of penetrating the cell membrane and various intracellular compartments. This makes it possible to generate SHALs specifically for the purpose of targeting intracellular molecules of importance to cell function, such as proto oncogenes, phosphokinases, lysosomal and other enzymes, DNA/RNA/mRNA, etc. This capability makes it possible to target entire classes of intracellular molecules of critical importance to cell function, a capability not previously achievable by specific targeting molecules. In addition to direct effects of these SHALs, they can be used as carriers of payloads, as described herein.

Proto oncogene products provide an example of a class of intracellular targets that can be targeted by SHALs and create a useful effect in cancer treatment. It is noted that Ras proteins, encoded by proto oncogenes, have been targeted in vitro by antibodies injected into the cells and this blockage has resulted in cells that no longer divide. Mutation have been related to impaired control activity of these products.

Many signaling pathways are susceptible to interference by the one (directly intra cellular) or two step (membrane targeting followed by internalization) SHAL targeting of intracellular molecules. These include, but are not limited to such key pathways as "g" protein signaling and tyrosine specific protein kinase activity e.g. EGFR, Neu, etc. Multiple hormone receptor interventions can also be targeted by SHALs to create a change in cell function and/or in cell growth. Hormone or enzyme targets can be bound and the function blocked. Hormone receptor blocks that can be useful include the use of SHALs to block the binding of estrogen like molecules to the ER(estrogen receptor) and similar effects to AR (androgen receptor). This would in turn interfere with DNA binding of the complex, with the resulting interference in hormone sensitive tumor cell growth and viability.

This invention also contemplates the use of SHALs to treat infectious diseases (e.g. AIDS, influenza, etc.) by either primary binding of the infectious agent and/or by blocking metabolic pathways critical to propagation of the infectious agent (e.g. by blocking CCR5 to prevent HIV infection of cells).

Where the target to which the SHAL is to be directed comprises a protein, in certain embodiments, at least one of the ligands (binding moieties) comprising the SHAL bind to a pocket in the protein. In certain embodiments, where at least two of the binding moieties comprising the SHAL bind to pockets of the protein and those two ligands bind to different pockets. In certain embodiments, all of the ligands comprising the SHAL bind to pockets in the target protein. This is not to suggest that all ligands comprising the SHAL must bind to protein pockets. Certain embodiments are contemplated wherein one ligand binds to a pocket and another ligand binds to a region that is not a pocket or where none of the ligands bind to a pocket.

When structural information is available for a particular target (e.g. a cancer marker or a domain or epitope within a cancer marker) then the target or domain within the target can be modeled to identify ligand binding sites for the design of a SHAL for this specific target. If the target has not been structurally characterized, then the crystal or NMR structure of related molecules may be used in this manner. In the event that information is not available, a less usual circumstance, then empirical approaches can be used to identify suitable ligands for the construction of a SHAL as described herein.

The empirical approaches described herein can also be used to accelerate the process of SHAL development. In this circumstance, modeling and other analytical steps can be performed after empirical development of a SHAL as desired to better understand the SHAL and/or to guide subsequent generations of SHAL development.

Although the examples illustrate one preferred embodiment where the SHAL is intended as a carrier for an imaging and therapeutic radioisotopes, such as indium-111 and yttrium-90, for diagnosis and treatment, and the intended target is the HLA-DR cell surface molecule found on malignant, and normal, B lymphocytes, and therefore useful in most lymphomas and leukemias, it should be emphasized that this is only one of many embodiments even in B cell lymphoma and leukemias. For example, antibodies are known to identify a number of other cell surface antigens known to be attractive for antibody targeting of B cell lymphoma and leukemias. These could also be used for the same purposes and in the same manner as those for HLA-DR. Of additional interest, the region targeted by SHALs designed for HLA-DR targeting, is in the area of the pit known for peptide presentation of importance to immune identification and rejection. Of even greater importance, antigens and epitopes have been characterized and shown to be important for antibody targeting of adenocarcinomas of all types, including, breast, prostate, and colon malignant diseases. The aberrant mucins of the adenocarcinomas and the CEA found abundantly on many adenocarcinomas also provide attractive targets that have been rather well characterized.

Figure 4B:
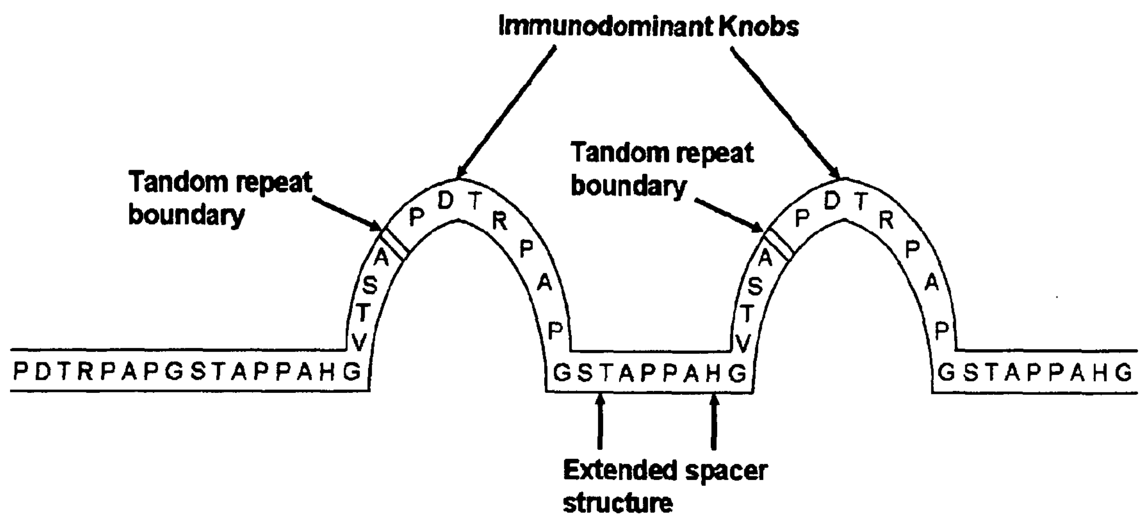
FIG. 4B illustrates the conserved structural features of the tandom repeat domain of MUC-1 (SEQ ID NO:20). These features include repeating and protruding knob-like structures consisting of sequential reverse turns that span tandem repeat interfaces (residues 17-27, 37-47), an extended region consisting of polyproline II and β-strand structure (residues 10-15, 30-35, 50-55). The N- and C-terminal 2-3 residues are unordered due to the absence of adjoining tandem repeats.
Figure 5:
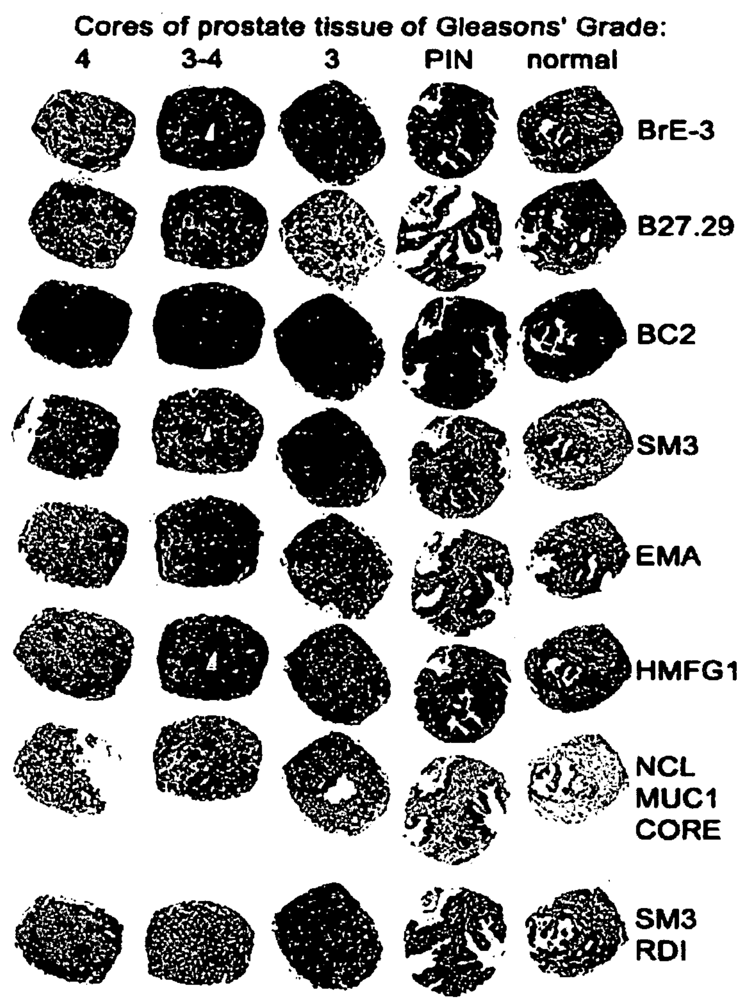
FIG. 5 illustrates a prostate cancer tissue array stained by anti-muc1 monoclonal antibodies.
Figure 6:
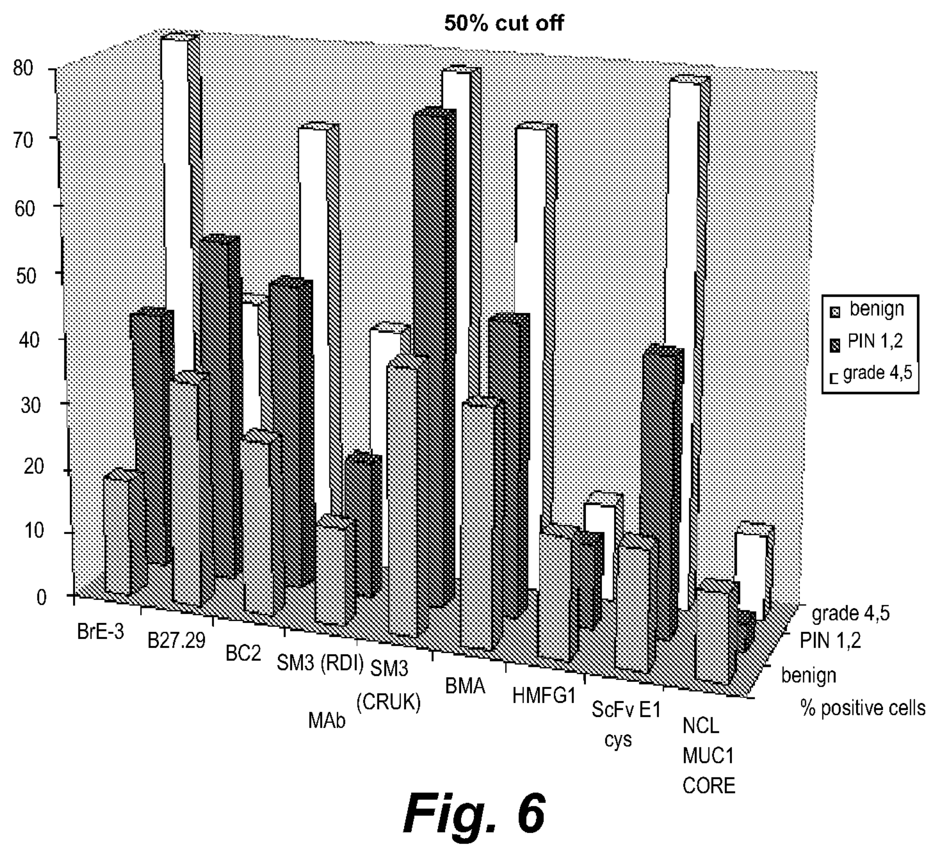
FIG. 6 shows that prostate cancer had increased MUC-1 peptide staining associated with grade and stage.
Figure 7:
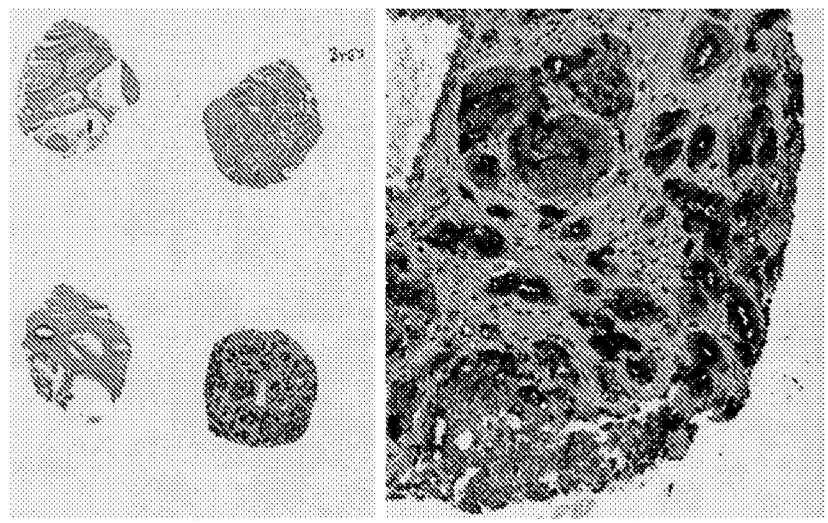
FIG. 7 shows anti MUC1 peptide core MoAb BrE-3 demonstrating target epitope in grade 4 prostate cancer. The knobs on MUC-1 differ in different grades of prostate cancer. Consequently, SHALs can be designed that bind to knobs and that can be used to grade malignant tissue.

In certain embodiments, it is believed the core tandem repeat protein of mucin (MUC1) (see, e.g., FIG. 4) provides a good target for cancer-directed SHALs. MUC-1 has been shown to be upregulated and readily available on epithelial cancers, such as prostate, breast, colon and ovarian cancers (see, e.g., FIGS. 5, 6, and 7).

Radioimmunotherapy (RIT), using Y-90 on a variety of monoclonal antibodies (mAbs), including those against MUC-1, has shown promise in preclinical studies and trials in patients. These studies have shown that epithelial cancers can be targeted effectively using radiolabeled mAbs, and that MUC-1 is one of the more attractive targets. Whole antibodies, however, are not readily concentrated in and typically do not penetrate through solid cancers. Consequently the therapeutic index for such moieties has proven to be relatively low.

However, MUC1-directed SHALs made, e.g. according to the methods described herein, directed against the protein core tandem repeat of MUC-1, an epitope shown in preclinical studies and RIT trials in patients to be a unique antigenic epitope upregulated on epithelial cancers are expected to be highly effective. SHALs (selective high affinity ligands) are quite small (~2000 Daltons) relative to whole antibodies (~150,000 D), or even single chain variable fragments (~25,000 D), so that SHALs readily penetrate and concentrate in malignant tumors, or are rapidly cleared or excreted by the kidneys.

In certain embodiments, additional ligand(s) beyond one or two chosen for docking sites in the epitopic region of interest are chosen for docking sites outside the region of interest on the target. This provides greater selectivity and "effective" affinity. In the case of a multimeric target, for example, HLA-DR, additional ligands can be directed to the same or to a different subunit of the target. Specifically, in the case of HLA-DR, one or two ligands can be directed to known docking sites in the epitopic region defined for Lym-1 monoclonal antibody reactivity and additional ligands can be chosen for docking sites in the same or a different multimer, for example, the beta subunit or the alpha subunit of HLA-DR.

Other examples are SHALs with ligands chosen to react with the tandem repeats of mucins, such MUC-1 as described above. In this instance, the core protein is repetitive at ten mer intervals so that SHALs of similar or identical nature can be joined to provide multivalent linkage to identical or similar but different repeats of known (or unknown) distance. Alternatively, the SHAL can have a third ligand that is identical to one of the initial ligands but linked at a distance to docking sites at a remote region of the core tandem repeat of MUC-1.

Also, docking sites can be protrusions in addition to cavities, although the latter are likely to confer greater (affinity) by virtue of the potential for more contact interactions.

B) Compounds (Putative Ligands/Binding Moieties) to be Screened.

Virtually any agent can be screened for its ability to bind a target and thereby for its suitability for incorporation into a SHAL according to the methods of this invention. Such agents include, but are not limited to nucleic acids, proteins/peptides, nucleic acid or peptide analogs, metals, sugars, polysaccharides, glycoproteins, lipids, lectins, large and small organic molecules, antibody CDRs, and the like.

In one preferred embodiment, high throughput screening methods involve providing a combinatorial chemical library containing a large number of potential ligands (binding moieties). Such "combinatorial chemical libraries" are then screened in one or more assays, as described herein to identify those library members (particular chemical species or subclasses) that display the desired binding activity. The compounds thus identified can serve as a component of a SHAL.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) *J. Med. Chem.,* 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175; Furka (1991) *Int. J. Pept. Prot. Res.,* 37: 487-493; Houghton et al. (1991) *Nature,* 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735), encoded peptides (PCT Publication WO 93/20242), random bio-oligomers (PCT Publication WO 92/00091), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909-6913), vinylogous polypeptides (Hagihara et al. (1992) *J. Amer. Chem. Soc.* 114: 6568), nonpeptidal peptidomimetics with a beta-D-glucose scaffolding (Hirschmann et al., (1992) *J. Amer. Chem. Soc.* 114: 9217-9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539,083) antibody libraries (see, e.g., Vaughn et al. (1996) *Nature Biotechnology,* 14(3): 309-314), and PCT/US96/10287), carbohydrate libraries (see, e.g., Liang et al. (1996) *Science,* 274: 1520-1522, and U.S. Pat. No. 5,593,853), and small organic molecule libraries (see, e.g., benzodiazepines, Baum (1993) C&EN, January 18, page 33, isoprenoids U.S. Pat. No. 5,569,588, thiazolidinones and metathiazanones U.S. Pat. No. 5,549,974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

In certain embodiments, the initial screen for ligands (binding moieties) with which to build the SHAL can be performed as a virtual in silico screening method and, in this case, it is not necessary to have the physical compounds in hand. In such instances chemical structure databases provide a wide range of moieties that can be screened for their suitability for inclusion in a SHAL as described herein.

Chemical structure databases are well known to those of skill in the art. For example, the MDL® Available Chemicals Directory (MDL ACD) is presently the largest structure-searchable database of commercially available chemicals in the world and is available from MDL Information Systems, Inc., San Leandro, Calif. This database is merely illustrative and not intended to be limiting. Other chemical structure databases are well known to those of skill in the art and include, but are not limited to various organic molecule, peptide, carbohydrate or nucleic acid structural databases.

C) Computational Identification of Ligands that Bind the Target.

Using a virtual in silico approach, computational methods can be used to characterize (e.g. model) the target (e.g. target protein) and to identify molecules (binding moieties) that are expected to specifically bind to certain regions of the target. The use of computational methods to identify molecules that specifically bind to a particular target is often referred to as "DOCKING".

Docking methods are well known to those of skill in the art. Two approaches to docking are "rigid molecule docking" in which the molecules involved are treated as rigid objects that cannot change their spatial shape during the docking process, and soft (flexible) docking where the molecules are (computationally) allowed to change shape as they dock.

There are several physical and chemical forces that interact between the two molecules. These forces are used to define various docking scores that measure quality of each solution. These scores take into account the strength of these forces and the plausibility of the docking solution. The most significant forces typically considered in docking algorithms include electrical forces, van der Waals forces, and hydrogen bonds.

The docking problem is often formally stated as follows: Let A,B be two rigid molecules (e.g. the target and the potential ligand that is to bind the target) with their geometric representation in R3. We would like to find a rigid transformation $T:R3 \rightarrow R3$ such that the contact surface between $T \cdot A$ and B is maximal. The contact surface is typically defined as the surface where the distance between the molecules is smaller than a given threshold. Typically docking algorithms try to achieve a contact surface which is "large enough" instead of "maximal" and that we try to maximize not the size of the contact surface but a score measuring the quality of the proposed docking solutions. These two parameters are correlated but are not equivalent.

1. Rigid Docking.

One approach to the rigid docking algorithm was described by Kuntz et al. (1982) *J. Mol. Biol.,* 161: 269-288. The Kuntz et al. algorithm is primarily used in solving ligand-protein docking while trying to focus on 'interesting' sites on the surface of the molecules. The basic stages of the algorithm involve first computing the molecular surface using Connolly's method (see, e.g., Connolly (1983) *J. Appl. Crystallography,* 16: 548-558; Connolly (1983) *Science,* 221: 709-713)). This produces a set of points on the "smoothed" molecular surface with their normals. Then a "sphere generator" (e.g. SPHGEN) is used to create a new representation of the molecular surface of the target (e.g. protein) and the ligand using "pseudo-atoms" and then uses this representation to find plausible docking sites on the molecular surface—these docking sites that SPHGEN is looking for are cavities in the surface of the receptor.

SPHGEN typically consists of the following five stages: First, for each pair on Connolly points $p_i$,$p_j$ a sphere passing through this pair is placed such that its center is on one of the points normal. The algorithm then defines $S_{norm}$(i) ={Spheres whose center is on the normal of $p_i$}. Assuming that there n Connolly points, then for each 1<=i<=n and $p_i$is on the surface of the target, we throw away all the spheres in $S_{norm}$(i) and leave only the one with the smallest radius. This throws all the spheres that penetrate the surface of the target. The algorithm then typically only leaves the spheres where Theta (e.g. the angle between the pi normal and the radius from $p_j$ to the center of the sphere) <90° . Otherwise the points that define the sphere, $p_i$and $p_i$, are too close to each other and therefore are not located in a cavity on the target's surface. Then the algorithm typically for each atom leaves only the sphere with the maximal radius. This step leaves only the spheres that 'touch' the surface of the atom. Finally, if the points that define the sphere, $p_i$ and $p_j$, belong to two different atoms, and the distance between these atoms on the molecular sequence is less than 4—the sphere is discarded. This is done because the length of a curve on an Alpha-helix is 3.6 and these sites are typically not to be treated as possible docking sites.

The remaining spheres are called pseudo-atoms. The next stage looks for clusters of intersecting pseudo-atoms. T he existence of this kind of cluster indicates the existence of a cavity in the molecular surface, which is considered to be a good docking site.

After all this is performed on the target the same is done on the ligand, but this time we take the points and the vectors opposite to their normals, in order to create the spheres inside the surface instead of outside the surface. The result of SPHGEN on the target is sometimes called the 'negative image' and on the ligand it's called the 'positive image'. In certain embodiments, the vectors with respect to the ligand and the target can be reversed (e.g. to find elements of the target that dock within cavities in the ligand).

"Matching" is then typically performed. In this operation, for each docking site, the algorithm tries to find a transformation T that gives a good correspondence between the centers of the pseudo-atoms of the target to those of the ligand (in some cases, the centers of the real atoms of the ligand are used, instead of the centers of its pseudo-atoms). In some versions of DOCK, clusters of pseudo-atoms are separated into sub-clusters in order to improve the complexity of this stage. One way of doing this is to discard the largest sphere in the cluster, which sometimes causes the cluster to be divided into two sub-clusters In the matching problem of rigid docking a search is performed to find a translation and rotation of one molecule, such that good matching between the interesting points in both molecules is formed. In certain embodiments, the distances between the point used instead of the points locations: For each molecule, the target (T) and the ligand (L), an appropriate distance matrix is defined—$d^T_{i,j}$ and $d^L_{i,j}$, respectively. A search is then performed to try to find two subsets in T and L such that their distances are the same, with some tolerance of error. These two subsets define two subgraphs with almost similar distances between their vertices. This can be done using a method similar to the interpretation tree by Grimson and Lozano-Perez.

Another way of solving the matching problem is to find a "large enough" clique in a matching graph. If there are n points in the target and m points in the ligand, the matching graph has n*m vertices where each vertex represents a point from the target and a point from the ligand. Let G=(V,E) be the matching graph and let u,v be vertices in V where u represents $u_L$ and $u_T$(points in the ligand and the target, respectively) and v represents $v_L$ and $v_T$. An edge e=(u,v) will be added to E only when ABS [$d^L(u_L,v_L)-d^T(u_T,v_T)$]<tolerance. Therefore, a clique in the matching graph defines subsets of points in the ligand and the receptor with similar distances.

In order to evaluate the quality of the match a score is calculated. The score preferably takes into account the size of the contact surface between the molecules and typically does not allow one molecule to penetrate the other. The DOCK algorithm uses a cubic grid that fills the binding site and every cell in this grid has a score according to its distance from the centers of the receptor's atoms: 1 if the distance is 2.8 Å–4.5 Å, −127 if the distance is less than 2.8 Å, and 0 if the distance is more than 4.5 Å. (In some cases the distance 2.8 Å is replaced by 2.4 Å). For each proposed transformation, the position of the ligand's points (i.e. the centers of its atoms or pseudo-atoms) in the grid are calculated and the score is calculated as the sum of scores of these points. Additional or alternative scores can be used various versions of the algorithm. For example, in one version a van der Waals energy score can be calculated for the transformations that have good matching scores.

Construction of a computer model of HLA-DR 10. Using the crystal structures that have been determined for four closely related human HLA-DR molecules (HLA-DR 1-4), the identification of unique "pockets" on surface of the protein, the identification of ligands that bind certain unique pockets and the construction of a SHAL using these ligands is illustrated herein in the examples.

The foregoing description is intended to be illustrative of one approach to rigid docking and is not intended to be limiting. Other approaches are known to those of skill in the art. It is noted that the SPHGEN and DOCK programs are commercially available (e.g. directly from the University of California and various commercial manufacturers of software).

2. Soft (Flexible) Docking.

Soft docking algorithms are also well known to those of skill in the art (see, e.g., Jiang and Kim (1991) *J. Mol. Biol.,* 219: 79-102; Katchalski-Katzir et al. (1992) *Proc. Natl. Acad. Sci. U.S.A.,* 89(6): 2195-2199, etc.).

In the method described by Jiang and Kim, supra, an enumeration on the 6-dimensional space of rigid transformation is performed and these transformations are given score according to their energetic value. Both molecules are placed on a grid and the matching is evaluated using the distances between grid cells, the number of penetrations and the directions of the points' normals. The algorithm works on the output of Connolly's algorithm and works on the entire molecular surface (i.e. no cavities are looked for—as opposed to the DOCK algorithm). In order to decrease the enumeration, the algorithm typically uses two resolutions—low and fine. The low resolution uses ~0.3 points per square angstrom, and the fine resolution uses ~1 point per square angstrom.

Each cell in the grid is marked as "surface" (if it contains at least one Connolly point) or "volume" (if it doesn't contain any Connolly point). Usually, each surface cell contains 2-3 Connolly points.

An enumeration on the rotations of one of the molecules (usually smaller one) is performed. For each rotation the following is performed: The surface and volume cell of the molecule is calculated. Assuming that there's at least one pair of surface cells (one from each molecule) that are matched by the transformation, an enumeration on all of these pairs is performed. For each pair the transformation is calculated and it is evaluated by checking the directions of the normals, the number of surface-to-surface matches and the number of penetrations. The good transformations are those who have a small number of penetrations and a lot of surface-to-surface matches. This is done first in low resolution and the best results are calculated again in fine resolution with the addition of an approximated energetic score. The approximated energetic score is calculated according to the number of "favorable" and "unfavorable" interactions. There are several categories for the atoms of each molecule and combinations of these categories are marked as "favorable" if they have a good contribution to the energetic plausibilty of the match, or "unfavorable" otherwise.

For example, it is unfavorable that an atom with positive charge is placed near another atom with positive charge, but it is favorable if two atoms are adjacent if one of them is an H-donor and the other is an H-acceptor.

The approach of Katchalski-Katzir et al., supra, is to enumerate on the possible translations, while using FFT to calculate the matching score efficiently. Similar to the previous algorithm, both molecules are placed on a 3-dimensional grid, but here 3 types of grid cells are defined—"volume", "surface" and "intermediate". If the molecules are A and B, the matrices $A_{l,m,n}$ and $B_{l,m,n}$ are defined as follows (l,m,n are the grid coordinates): $A_{l,m,n}$={1—if (l,m,n) is a "surface" cell, q—if (l,m,n) is an "intermediate" cell, 0—otherwise}, and $B_{l,m,n}$={1—if (l,m,n) is a "surface" cell, r—if (l,m,n) is an "intermediate" cell, 0—otherwise}.

In certain embodiments, parameters are chosen such that $q<0$ and $r>0$ while $|q|$ is large and $|r|$ is small. The scalar product of these matrices can be efficiently calculated using FFT thus improving the algorithm's performance considerably.

Again, it is noted that the foregoing description is intended to be illustrative of one approach to rigid docking and is not intended to be limiting. Other approaches are known to those of skill in the art. For example, additional approaches/programs include, but are not limited to: FlexX from Tripos which is commonly used for high-throughput screening. It uses an empirical scoring function. It allows for flexible docking by rotating around torsional bonds. It is sold as a module of the Sybyl program (distributed by Tripos, Inc., St. Louis). GOLD from CCDC which uses a genetic algorithm to generate conformers for a ligand. It also enables customization of the torsional energy within smaller fragments of the molecule and can accommodate local protein flexibility. AutoDock UCSD uses a Lamarckian genetic algorithm to generate conformers for a ligand. AutoDock is best used when there are only a few ligands and the binding energies need to be more accurate. Some good reviews on Docking include Lyne (2002) *Drug Discovery Today.* 7 (20): 1047, and Taylor et al. (2002) *J. Computer-Aided Mol. Design.,* 16: 151.

D) Empirical Approaches and Verification of Ligand Binding.

The use of computational methods to identify ligands for use in the construction of a SHAL requires at least some information regarding the structure of the target molecule(s). This invention also contemplates the use of methods that require no knowledge regarding the structure of the target to which the SHAL is to be directed.

In certain "empirical" embodiments, individual ligands or libraries of ligands are screened against the target molecule(s) and/or cells, bacteria, viruses, etc. displaying the target molecule(s) to identify ligands that bind the desired target (at least low affinity). Ligands are identified that bind to different regions of the target molecule(s). In certain embodiments, ligands are identified that bind to different regions of the target molecules and that do not exclude each other from such binding.

Ligands that can simultaneously bind to the target without excluding each other can then be joined together, directly or through a linker, to create a polydentate SHAL which can, optionally, be subsequently screened for the ability to bind to the target molecule(s), e.g. at high affinity.

In addition to use in empirical approaches for ligand identification, physical screening methods are also desirable for validating binding of ligands identified using the virtual in silico approaches discussed above. In addition, it can be desirable to additionally determine the binding orientation of two or more ligands, e.g. to confirm that the ligands bind to different sites on the target and/or to estimate spacing when the ligands are incorporated into a SHAL.

Assays for detecting the binding of one or more ligands to a target are well known to those of skill in the art. For example, in one simple embodiment, the ligands can be labeled with a detectable label and contacted with the target molecule(s) which are immobilized on a substrate. After a wash, detection of the labels in association with the immobilized target molecule(s) indicates that the ligands bind to the target. In certain embodiments, different ligands can be labeled with different labels (e.g. different color fluorescent labels), and the simultaneous binding of multiple ligands can be visualized.

Alternatively, competitive binding assays can be performed. In such assays the target molecule(s) are contacted with one ligand known to bind the target. The target is also contacted with the "test" ligand and the ability of the test ligand to bind to the target in the presence of the first ligand is evaluated.

Fluid phase assays can also be performed. For example, the ligand(s) and the targets can be labeled with different labels. The ligands can be contacted to the target molecule(s) and binding of the two can readily be evaluated, e.g. using a flow cytometer. Flow cytometry methods are well known to those of skill in the art (see, e.g., Omerod (1994) *Flow Cytometry: A Practical Approach*. IRL Press, Oxford.; Shapiro Practical Flow Cytometry. 3rd Edition. Alan R Liss, Inc.; Givan (1992) *Flow Cytometry. First Principles*. Wiley-Liss, New York; Robinson (1993) *Handbook of Flow Cytometry Methods*, Wiley-Liss, New York, and the like).

Determination of ligand binding and orientation can also be determined using a number of different methods. These include, but are not limited to Saturation Transfer Difference nuclear magnetic resonance (Mayer and Meyer (1999) *Angew Chem Int Edit,* 38:1784-1788) and Transfer NOE (trNOE) nuclear magnetic resonance (NMR) spectroscopy (Henrichsen et al. (1999) *Angew Chem Int Edit.,* 38:98-102; Cosman et al. (2002) *Chem Res Toxicol* 15: 1218-1228). These methods can be used to screen the ligands in mixtures of several to several hundred per experiment to determine which ligands bind to the target molecule(s) e.g., under biologically relevant conditions and to determine which ligands bind to the same (or different) sites. Diffusion experiments (Lin et al. (1997) *J. Organic Chem.,* 62: 8930-8931) can also be performed with those ligands that have been determined to bind in order to assess the relative binding affinity of each compound.

Other approaches to detecting binding of the ligands to the target molecule(s) include, but are not limited to surface plasmon resonance (BIAcore assay), saturation transfer difference nuclear magnetic resonance spectroscopy, other nuclear magnetic resonance spectroscopy measurements, mass spectrometry, capture microarrays, bead-based library assays, and other physical binding assays.

The foregoing assays are intended to be illustrative and not limiting. Using the teaching provided herein numerous other assays for detecting ligand binding to the target molecule(s) will be known to those of skill in the art.

Following the identification of a set of ligands that bind to the target molecule(s) (e.g., HLA-DR10), competition experiments can be performed, e.g., by NMR to determine if they bind to one of the pockets comprising the target molecule(s) (e.g., in the case of HLA-DR10, to one of the pockets encompassing the Lym-1 epitope.

As indicated above, this can readily be accomplished by preparing a complex between the target and a known binding ligand and determining if a second ligand can bind the complex. Thus, for example, the case of HLA-DR10 target, a Lym-1:HLA-DR10 complex can be prepared and the set of ligands that bind to HLA-DR10 can be re-tested to determine if they will still bind to the protein when the Lym-1 antibody is bound.

Those ligands that no longer bind to the Lym-1:HLA-DR10 complex can be identified (these ligands bind to the unique sites that distinguish HLA-DR10 from the other HLA-DR molecules) and used in a second set of competition experiments to identify those molecules that bind to different sites within the Lym-1 epitope. In experiments conducted with pairs of ligands, transfer nuclear Overhauser effects (trNOE) that occur between the bound ligands and the HLA-DR10 protein (Cosman et al. (2002) *Chem Res Toxicol* 15: 1218-1228), in the absence of the Lym-1 antibody, can be used to identify those ligands that bind to the same and different sites. Bound ligands exhibit negative NOE signals, while unbound ligands have positive signals (Id.). If both ligands in the pair are observed to be bound to the protein at the same time, the results will indicate that the two ligands must bind to different sites. The screening thus can readily identify sets of ligands that bind to different sites within the target molecule(s) (e.g., to different sites (Site 1 and Site 2) within the Lym-1 epitope of HLA-DR10).

After sets of ligands have been identified that to bind to different sites on the target, the orientation of the ligands in the binding sites can, optionally, be further evaluated using classical molecular dynamics simulations. The methods of molecular dynamics simulations are clearly described in the Examples. For example, for each ligand, one to three orientations within the binding pocket can be simulated for 500 psec. This will help determine which functional groups on the ligands are likely to be in contact with the target and which functional groups are accessible by solvent. This information can be used to identify analogs with modified or different functional groups that can be tested for their ability to bind to the target and confirm that a particular functional group can be used as the site for linker attachment without disrupting the binding of the ligand to the target.

The use of these approaches to identify ligands that bind to specific sites on various targets is described in the literature. For example, these methods have been used to identify ligands that bind to specific sites on the targeting domain of tetanus neurotoxin (Cosman et al. (2002) *Chem Res Toxicol* 15: 1218-1228; Lightstone et al. (2000) *Chem. Res. Toxicol.,* 13: 356-362) as well as eleven ligands we've already identified that bind to HLA-DR10.

Our previous studies using a similar approach to identify ligands that bind to two sites on the targeting domain of tetanus neurotoxin (Id.) have required screening less than 30 ligands experimentally. Over half of the ligands predicted to bind to the protein were observed to bind experimentally. Thus we believe that screening a set of 30 ligands per site should provide a sufficient number of compounds that bind to initiate SHAL synthesis. However, if in some embodiments, a suitable number of ligands (e.g., 3-5) are not identified to bind in the first round of NMR screens, additional sets of ligands can be selected and screened until suitable ligands are found that bind to two different sites in the target.

In certain embodiments, the selection of the ligand pairs (or other multi-ligand combinations) to be linked together is based on the following criteria (in descending order of importance): 1) binding site (the two ligands that comprise a pair preferably bind to different sites); 2) reliability of information obtained on available functional groups that can be used to attach the molecules to the linker without disrupting binding (analogs with known derivatives that are confirmed to bind, indicating the modification of particular functional group does not affect binding, are given priority); 3) the ligand's expected ease of attachment to the linker (the ligands preferably have functional groups that facilitate asymmetric attachment chemistry to put a different ligand on opposite ends of the linker); 4) relative binding affinity, e.g., as determined from the NMR diffusion experiments (ligands exhibiting the strongest binding to the protein are typically selected first); 5) known information on their toxicity in animals or humans (priority is typically given to use of ligands that are known to be non-toxic or have already been approved for use in other pharmaceuticals); and 6) ligand cost.

Because it is likely that a number of the individual ligands (binding moieties) may bind weakly to other proteins, it will not be necessary (or meaningful) to prescreen the individual ligands to determine if they bind to other proteins that might be encountered in the circulation before they are used to create SHALs. The binding of any single ligand (half of the pair used to create a bidentate SHAL) to other proteins is expected to be weak (micromolar at best). Consequently, the off-rate of the molecule will be high and the SHAL that only binds through one ligand to other proteins will be quickly removed from the tissue and circulation. High affinities (and low off-rates) typically will only be obtained when both ligands in the pair bind simultaneously to sites separated by the proper distance, which is dictated by the length of the linker connecting them. These two criteria will only be met when the SHAL comes in contact with the intended target. Once bound, the off-rate is expected to be reduced 1000 to 1,000,000 fold (based on previous studies) over that observed for either ligand alone. For this reason, cross-reactivity is not expected to be a significant complication.

E) Combined Computational/Empirical Approaches.

The binding of a SHAL to the region(s) of its target is based upon fit and charge and is dependent on the 3D structure and constituents of the binding moieties. In the computational approach described above, generating SHALs can involve definition/identification of attractive region(s) on the target molecule. Thus, for example, proteins of all types, including antigens, receptors and signaling proteins, can be modeled to find docking sites and ligands. The ligands can subsequently be tested using empirical methods. These methods typically require knowledge of the constituent molecules to be included in the modeling.

The empirical methods described above, rely on screening of libraries (e.g., combinatorial libraries) of potential ligands to find suitable binders. In this approach, no foreknowledge is required beyond availability of a target (e.g., protein, cell, etc.) of interest. Libraries are experimentally culled for binders. This can be followed by competition with a molecule, such as an antibody, peptide or chemical (ligand) known to react with the molecule in the region chosen to be targeted. This approach permits the elimination of binding chemicals or peptides that are not of interest and definition of those that bind to the region of interest.

A third approach is intermediate in nature and uses foreknowledge of attractive target molecules and regions of these molecules for initial competitive screening and counter-screening. Thus, for example, initial targets or ligand-library constituents can be computationally predicated. The optimized target or target collection and/or optimized library can then be screened and counter-screened as described herein to identify optimal binders.

F) Bead-Based Library Screening.

One approach for screening for ligands that bind the target molecues involves producing a combinatorial library comprising a large number of potential ligands each attached to a different bead/solid support. The combinatorial library can be a "random" library, or can be synthesized to provide numbers of variant having, e.g. particular (e.g. optimized) core chemistry.

Combinatorial synthetic methods are well known and are used to rapidly make large "libraries" of distinct compounds. In various embodiments the starting material (e.g. an amino acid) is covalently anchored to solid support. This is followed by the stepwise addition of monomers (typically protected monomers) such as amino acids, nucleotides, small organic molecules, and the like. Millions of distinct molecules by varying number of steps and number of reactants (e.g. in a split-mix synthesis approach), but typically each bead contains only one compound.

The compounds comprising the library can be screened while still bound to the beads. Colorimetric, fluorometric, radiographic methods or other methods can be used to visualize positive (binding) beads. These can be captured (e.g. with a pipette, with a metal bar if the beads are magnetic), and the compound can then be characterized.

Thus, for example, one can synthesize a library of peptide ligands that bind HLA-DR10 molecules. Peptide synthesis chemistry is well developed. However, to obtain peptide ligands that have a longer half-life in vivo, one might choose to produce a peptide ligand library where the peptides comprise D-amino acids. Such peptides are expected to be more resistant to proteolysis in vivo. Moreover, D-amino acids are generally considered non-toxic.

The Lym-1 epitope on HLA-DR10 is highly polar. Thus, in synthesizing the library of potential binders on can select polar D-amino acids for synthesis (e.g., Ser, Asp, etc.) Using Split/Mix synthesis (see, e.g., U.S. Pat. No. 5,574,656) a library of D-peptides bound to beads is created.

Then HRP-tagged HLA-DR10 is added to the bead mixture. The HRP color label is visualized and the positive beads are removed. The positive beads can then be tested against, e.g., HLA-DR10 positive cell lines. Beads that test positive in this assay can then be tested against, e.g., a tissue panel to ensure that binding is HLA-DR10 specific. The specific binders in this assay can then be characterized (e.g. sequenced using Edman degradation, mass spectrometry, etc.).

Alternatively, there are strategies for encoding the identity of each the compound during the synthesis of the library (see, e.g., U.S. Pat. Nos. 5,565,324; 5,723,598; 5,834,195; 6,060, 596; 6,503,759; 6,507,945; 6,721,665; 6,714,875; and the like). Using such "tagging" strategies the identity of the positive binders can then readily be determined.

G) Linking the Ligands (Binding Moieties) to Produce a Polydentate SHAL.

Once two more ligands (binding moieties) are identified that bind to different sites on the target, the ligands are linked either directly or through a linker to produce a polydentate SHAL. Where only two ligands are joined the SHAL is bidentate. Where three ligands are joined the SHAL is tridentate, and so forth.

A number of chemistries for linking molecules directly or through a linker are well known to those of skill in the art. The specific chemistry employed for attaching the ligands (binding moieties) to each other to form a SHAL will depend on the chemical nature of the ligand(s) and the "interligand" spacing desired. Ligands typically contain a variety of functional groups e.g. carboxylic acid (COOH), free amine (—NH2) groups, that are available for reaction with a suitable functional group on a linker or on the other ligand to bind the ligand thereto.

Alternatively, the ligand(s) can be derivatized to expose or attach additional reactive functional groups. The derivatization may involve attachment of any of a number of linker molecules such as those available from Pierce Chemical Company, Rockford Ill.

A "linker", as used herein, is a molecule that is used to join two or more ligands (binding moieties) to form a polydentate SHAL. The linker is typically chosen to be capable of forming covalent bonds to all of the ligands comprising the SHAL. Suitable linkers are well known to those of skill in the art and include, but are not limited to, straight or branched-chain carbon linkers, heterocyclic carbon linkers, amino acids, nucleic acids, dendrimers, synthetic polymers, peptide linkers, peptide and nucleic acid analogs, carbohydrates, polyethylene glycol and the like. Where one or more of the ligands comprising the SHAL are polypeptides, the linkers can be joined to the constituent amino acids through their side groups (e.g., through a disulfide linkage to cysteine) or through the alpha carbon amino or carboxyl groups of the terminal amino acids.

In certain embodiments, a bifunctional linker having one functional group reactive with a group on a the first ligand and another group reactive with a functional group on a second ligand can be used to form the desired SHAL. Alternatively, derivatization may involve chemical treatment of the ligand(s), e.g., glycol cleavage of the sugar moiety of glycoprotein, carbohydrate or nucleic acid with periodate to generate free aldehyde groups. The free aldehyde groups can be reacted with free amine or hydrazine groups on a linker to bind the linker to the ligand (see, e.g., U.S. Pat. No. 4,671, 958). Procedures for generation of free sulfhydryl groups on polypeptide, such as antibodies or antibody fragments, are also known (See U.S. Pat. No. 4,659,839).

Figure 13A:
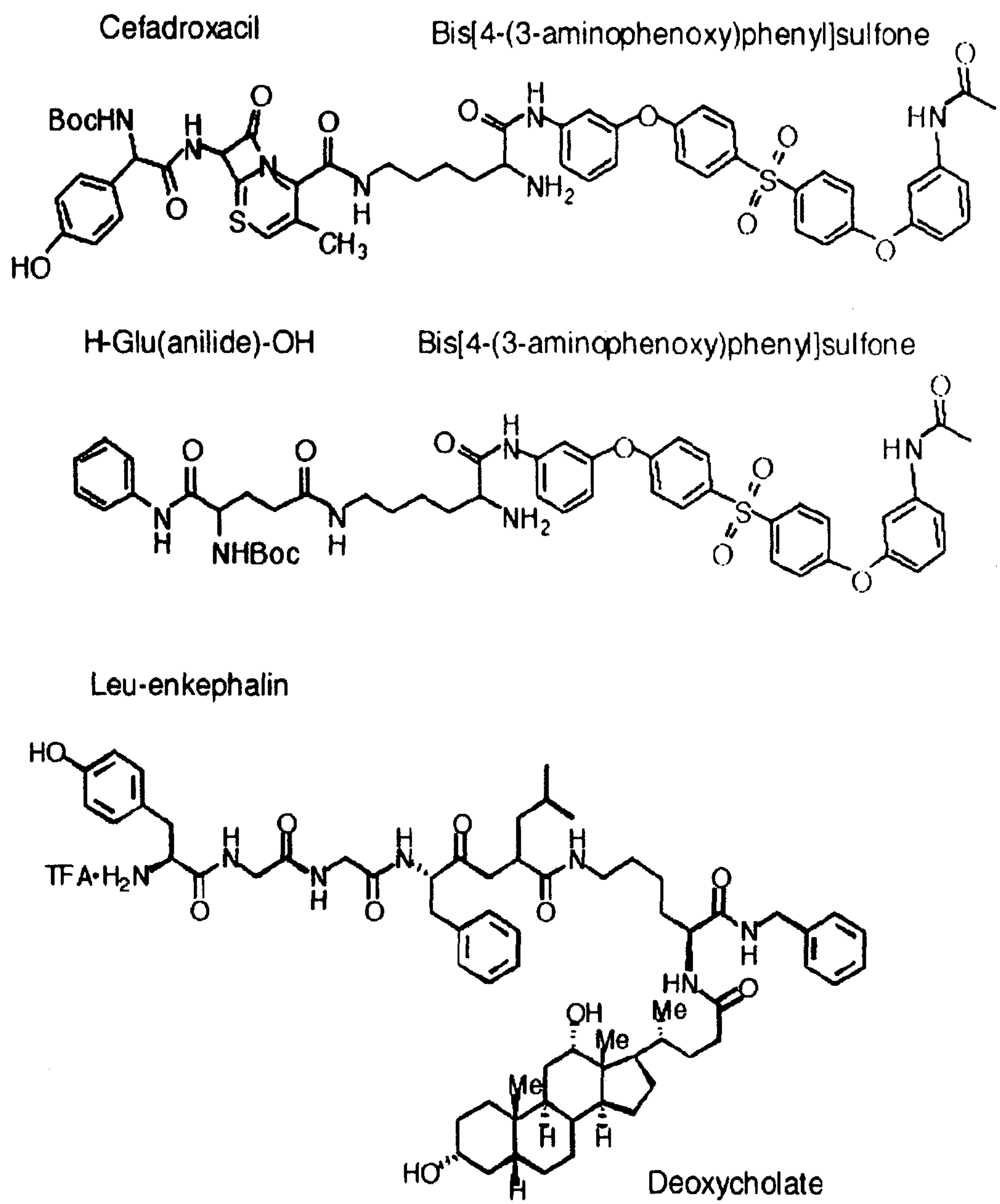

In certain embodiments, lysine, glutamic acid, and polyethylene glycol (PEG) based linkers of different length are used to couple the ligands. A number of SHALs have been synthesized using a combination of lysine and PEG to create the linkers (see, e.g., Examples and FIG. 13). Chemistry of the conjugation of molecules to PEG is well known to those of skill in the art (see, e.g., Veronese (2001) *Biomaterials,* 22: 405-417; Zalipsky and Menon-Rudolph (1997) Pp. 318-341

In: Poly(ethyleneglycol) Chemistry and Biological Applications. J.M. Harris and X. Zalipsky (eds)., Am. Chem. Soc. Washington, D.C.; Delgado et al. (1992) *Drug Carrier Syst.,* 9: 249-304; Pedley et al. (1994) *Br. J. Cancer,* 70: 1126-1130; Eyre and Farver (1991) Pp. 377-390 In: Textbook of Clinical Oncology, Holleb et al. (eds), Am. Cancer Soc., Atlanta GA; Lee et al. (1999) *Bioconjug. Chem.,* 10: 973-981; Nucci et al. (1991) *Adv. Drug Deliv.,* 6: 133-151; Francis et al. (1996) *J. Drug Targeting,* 3: 321-340).

One advantageous feature of the synthetic scheme used to create these SHALs is that the approach allows the attachment of almost any type of molecule to a third site on the linker. In the first round of SHAL synthesis, biotin has been attached at this site to facilitate the in vitro binding studies. The biotin tag makes it possible to quickly measure the binding to the isolated protein by surface plasmon resonance and examine the selectivity of the SHAL for binding to live cells and tissue sections.

Once the SHAL has been tested and confirmed to bind to the target (e.g. HLA-DR10), metal chelators such as DOTA (or other effectors) can be attached in the final round of synthesis to enable the delivery of radionuclides or other effectors to target bearing cells (e.g. tumor cells).

After retesting the effector-SHAL conjugates to reconfirm their ability to bind to the target, the conjugates exhibiting the best selectivity for their targets can, optionally be tested for their biodistribution in test organisms (e.g. mice). Other unique molecules can also be attached to this site in future studies so these same SHALs can also be used, for example, to test the utility of pre-targeting approaches for radioisotope delivery.

H) Stepwise Solid-Phase SHAL Synthesis.

In certain embodiments, SHAL synthesis proceeds by a stepwise-solid phase synthesis approach. In this approach each linker component or ligand is attached onto a growing molecule (SHAL) covalently attached to the surface of a resin. After each chemical reaction the resin can be extensively washed to remove the unreacted products.

In one approach, DOTA was attached to the linker at the beginning of the synthesis. After the excess DOTA was washed away, multiple additional chemical reactions that were carried out on the resin to add the various linkers and ligands, and after each reaction the unreacted products were again washed away. By the time the synthesis of the SHAL was completed, the amount of free DOTA present in the sample was undetectable when examined by HPLC and mass spectroscopy. The DOTA link is extremely stable, so it does not come off the SHAL once it's been attached.

I) Screening SHALs for Affinity and Selectivity.

In certain embodiments, a library of SHALs comprising different ligands (binding moieties) and/or comprising different length linkers is screened to identify those SHALs that have the best affinity and/or selectivity for the target. Such screening assays can be performed in a number of formats including, but not limited to screening for binding to isolated targets, screening for binding to cells in culture, screening for binding to cells in tissue arrays, and screening for in vivo binding to the desired target.

1. SHAL Binding to Isolated Targets (e.g. Proteins).

In certain embodiments, the binding affinities of the best SHALs can be estimated by mass spectrometry of the SHAL-target complexes, followed by a more accurate surface plasmon resonance (SPR) spectroscopy (Shuck (1997) *Annu Rev Biophys Biomol Struct.,* 26: 541-566; Van Regenmortal (2001) *Cell Mol Life Sci.,* 58: 794-800) measurement of the SHAL-target binding affinity using for example, the IASYS Plus or BiaCore instruments. In order to perform the SPR measurement, biotin can be added to the linker through a third functional group (as described above) and the SHAL can be bound to commercially available streptavidin coated chips. In certain preferred embodiments, only those SHALs exhibiting nM or higher binding affinities can be considered useful. The SHALs exhibiting the greatest affinity can then be tested for their selectivity. Experiments can be performed to test the selectivity of SHAL binding to targets in the presence of molecules related to the targets. Thus, for example, where the SHAL is directed to HLA-DR10, the SHAL can be evaluated for its ability to bind target molecules in the presence of Raji cell surface proteins extracted and separated by affinity chromatography. After treating the gel with the biotinylated SHAL and rinsing out excess unbound SHAL, the location of the bound SHAL can be detected by staining with Rhodamine tagged streptavidin. In certain embodiments, the SHALs that are considered to exhibit reasonable protein selectivity can be those molecules in which 95% or more of the fluorescence is associated with the HLA-DR10 monomer and multimer peaks.

2. SHAL Binding to Cells in Culture.

Where the SHAL target is a marker on a cell (e.g. a cancer cell marker) it may be desired to assess the specificity of binding of the SHAL to intact cells.

Cell binding studies can be conducted with the biotinylated (or otherwise labeled) SHALs, using for example the fluorescence of bound Rhodamine-tagged streptavidin to confirm the SHALs bind to target (e.g. Raji) cells. If the SHAL is observed to bind, SPR measurements can be conducted to determine the affinity of intact cells to the SHAL. In certain embodiments, those SHALs that exhibit at least a 2-fold, preferably at least a 5-fold, and more preferably at least a 10-fold difference in the staining intensity of target (e.g., tumor) cells over controls can be selected for further testing and development. Analogs of the most promising SHALs can be synthesized with a DOTA molecule attached to the linker, and binding experiments can be conducted using radionuclide-tagged SHALs to obtain more quantitative data and also attempt to determine if the SHAL is retained on the surface of the cell or is internalized using Nano SIMS. This information will prove useful in making decisions about the type of radioisotope that is to be loaded into the chelator. If the SHAL remains on the surface, the SHAL is typically utilized alone or with effectors that do not require internalization (e.g. alpha emitters such as $^{90}$Yttrium, various detectable labels, and the like). If evidence is obtained to suggest the SHAL is internalized upon binding to the target cells, it is possible to utilize the SHAL with effectors that are active when internalized.

3. Analysis of Cell Selectivity Using Tissue Arrays.

Figure 2:
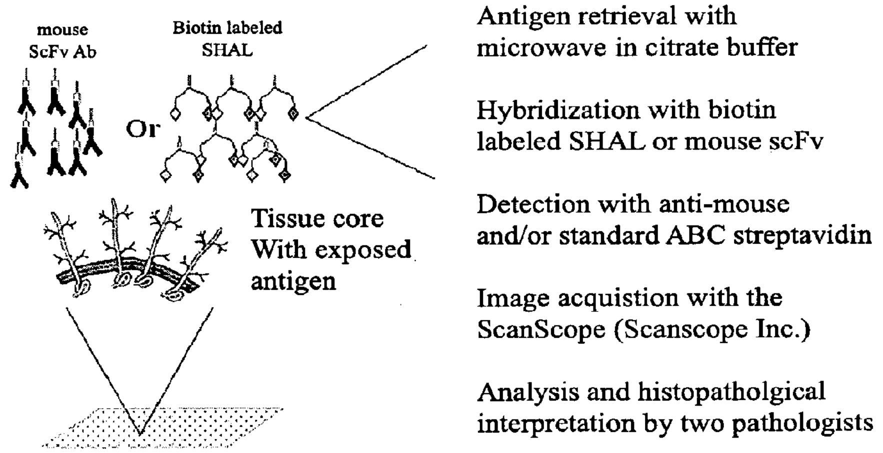
FIG. 2 illustrates the use of tissue microarrays that contain, for example, a large number of both normal tissues and lymphocytic neoplasms. These tissues can be treated with biotin-tagged SHALs, rinsed with rhodamine-tagged streptavidin, and the binding of the SHAL assessed by fluorescence microscopy.
Figure 3:
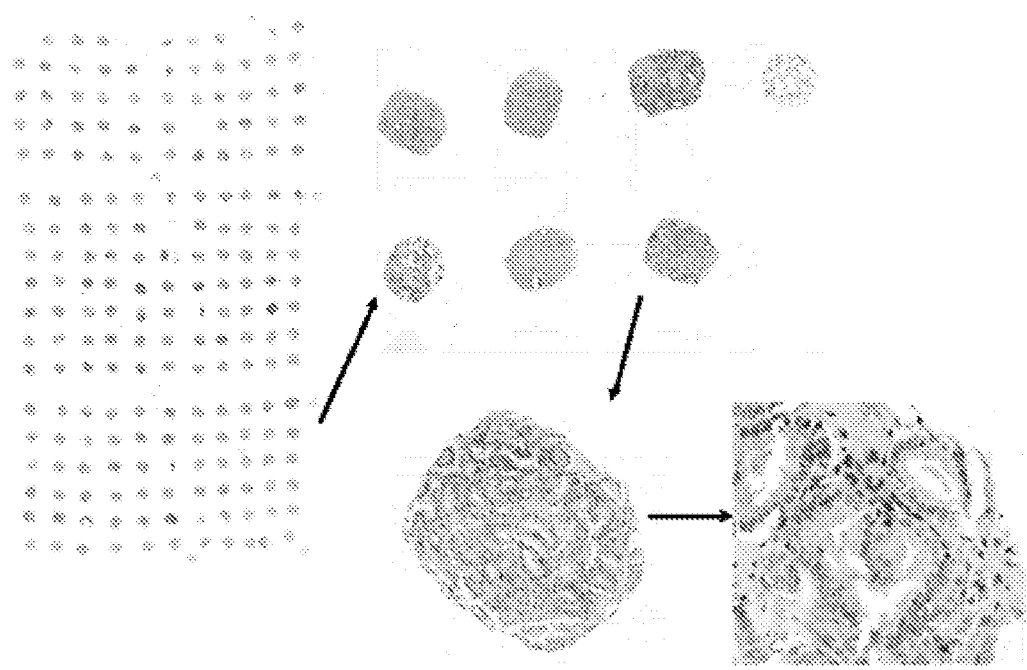
FIG. 3 illustrates a human tissue microarray comprising hematoxylin and eosin stained, formalin-fixed, paraffin embedded tissue cores. All four panels are derived from a single ScanScope digital image. This illustrates the high resolution of the archived image. Similar images can be captured for immunohistochemical or SHAL binding studies. In this way, investigators using the arrays have easy shared access for all studies applied to the arrays.

Tissue array technology can be used to screen SHALs to determine tissue specificity (e.g. malignant and normal tissue reactivity in the case of anti-tumor SHALs). Tissue arrays are well known to those of skill in the art (see, e.g., Kononen et al. (1998) *Nat Med.,* 4:844-847; Torhorst et al. (2001) *Am J Pathol.,* 159: 2249-2256; Nocito et al. (2001) *Int J Cancer,* 94: 1-5, and the like). In its basic form, a tissue microarrays is formed by taking small cores of each individual tumor case/block and assembling these cores into a single block (Id.). By sectioning this new block, standard immunohistochemistry and in-situ hybridization techniques can be used. Therefore, one can assay hundreds of tissue samples in one experiment rather than having to perform hundreds of different experiments. FIGS. 2 and 3 outline how the tissue arrays can be used and show a diagram of illustrative tissue array.

In one embodiment, for the normal tissue array we have identified 80 unique tissues, which include oropharynx, heart, lung, stomach, spleen, liver, kidney, intestine, bone marrow, pancreas, bladder, muscle, adrenal, breast, brain, normal prostate and skin for placement on the tissue microarray. For a lymphocyte specific tissue array, we have included neoplastic lymphocytic lines, xenografts, and patient material collected from the Human Biological Specimen Repository at UC Davis. Using these or similar tissue arrays, one can determine the non-specific binding of the SHALs to normal tissue and specific binding to lymphocytic and prostatic neoplasms. The hybridization of the SHALs to the tissue arrays is straightforward. Using biotinylated SHALs as described herein, labeled streptavidin (e.g. Rhodamine-tagged streptavidin) can readily be used to identify those cells that bind the SHALs. When required, the tissue microarray results can be verified by conventional histology and immunohistology.

In one illustrative approach, 2-4 tissue cylinders, with a diameter of 0.6-mm, can be punched from the selected areas of each "donor" tissue block and brought into a recipient paraffin block in order to assemble the tissue microarray, using a Tissue Microarrayer (e.g., Beecher Instruments, Silver Spring, Md.) and the techniques described by Kononen et al. (1998) *Nat Med.,* 4:844-847. Tissue microarray slides containing, for example, 200-400 cores can then be sectioned at a thickness of 4 μm. Routine Hematoxylin & Eosin staining can be performed in order to verify that each core represents its selected histopathology. For immunohistochemistry, microwave in a citrate buffer can be used for antigen retrieval. The images of the slides can be captured by confocal scanner (ScanScope, Mountain View, Calif.) and visualized with MrSid Viewer 2.0 (LizardTech, Inc.) as described below. The ability to view the tissue array images on a computer rather than a microscope dramatically increases the efficiency of analysis.

The major obstacle to digital pathology has been the representation of glass slides in a digital format. Unlike radiology, which begins with a digital representation of a patient rendered by CT, MRI, or now "digital plain film", pathology requires that all tissue samples be processed and made into stained tissue sections mounted on glass slides for interpretation. The new technology produces images of the entire glass slide, thereby producing a true digital representation of the entire histopathologic specimen (Whole Slide Imaging). Most of the current instruments use a microscope equipped with a digital camera and a robotic stage to capture thousands of individual images. Each image is focused by the content expert. Once acquired, these images are typically be stitched (or tiled) together to form the final representation of the slide. This process is both very time consuming and, due to the high number of images involved, the images are often misaligned.

ScanScope, (Aperio® Technology) is a new type of digital slide scanner that scans a microscope slide in 3 to 5 minutes, capturing 8 to 12 gigabyte images at 50,000 dpi. The images are then compressed, processed and stored for presentation (see below). MrSid® by Lizardtech® compresses the large, 8 to 12 gigabyte images using a proprietary multi-layer wavelet Jpeg format with compression ratios reaching 20:1 without significant image degradation. The images can then be either viewed locally or served from a web server. Unlike standard web-based still images, which are typically downloaded to be viewed within a browser, the MrSid processed images are viewed from the web, and the browser application never downloads the entire image. Because the images are acquired at their maximal resolution, "lower" magnification views of an image are constructed by the server. Using the combination of ScanScope and Zoomify browser, entire slides (12 gigabytes) can be captured and processed in less than 20 minutes.

4. In Vivo Analysis of Selectivity.

Of course in vivo selectivity of a SHAL can also readily be determined. This can be accomplished by administering the SHAL to a test animal (e.g. a laboratory rat) comprising a cell or tissue that displays the target to which the SHAL is directed. After sufficient time, the animal can be sacrificed and the target tissue(s) and normal tissues examined (e.g. histologically) to evaluate the specificity and amount of SHAL delivery. In certain embodiments, the SHAL can be coupled to an imaging reagent that permits non-invasive imaging and thereby permit the evaluation of realtime pharmacodynamics.

By way of illustration, pharmacokinetic and radiation dosimetric mouse studies can be performed, e.g. on the SHALs illustrated in the Examples, to generate data upon which to select one for clinical trials of pharmacokinetics and radiation dosimetry in patients, using established methods. Pharmacokinetics can be performed in female nude mice bearing Raji human lymphoma xenografts of defined size using established methods (DeNardo et al. (1998) *Clin. Cancer Res.,* 4: 2483-2490; Kukis et al. (1995) *Cancer Res.,* 55: 878-884). Mice can be injected with DOTA-tagged SHALs containing $^{111}$In or $^{90}$Y and mice can be sacrificed, e.g., at each of at least 5 time points to provide samples for analysis. Initial studies can be conducted at the extremes of early and late time points expected for these small molecules so that the intermediate time points can be determined. Data for peptides can be used to define the extreme time points. When using $^{111}$In or $^{90}$Y as a tracer, the longest time point would typically be about 5 days. Total body clearances can be determined using a sodium iodide detector system. Blood clearance can be monitored by taking periodic blood samples from the tail veins of the mice. At the time of sacrifice, the xenograft and normal tissues can be removed, weighed and counted in a gamma well counter to provide organ distribution data.

In order to assess SHAL dose (mass) effect, studies can be conducted at, e.g., 5 dose levels, once again beginning with small and large SHAL amounts to guide selection of the intermediate amounts to be studied. Because of the novelty of the SHALs, selection of study time points and dose levels will typically be guided by information available for antibody (e.g., Lym-1) studies in mice and for, e.g., somatostatin receptor peptide ligands.

In certain embodiments, the ideal pharmacokinetics and dosimetry to achieve with our SHALs are those that approach what has been accomplished using sodium iodide (NaI) in the treatment of thyroid tumors. The SHALs should be small enough to completely penetrate the malignancy and be readily excreted in the urine. Typically at least an order of magnitude better target recognition and binding affinity to lymphomas and leukemias than current antibodies will provide the desired tumor cell selectivity. While the rapid clearance of smaller molecules, such as the SHALs, from the circulation might be considered a disadvantage, the remarkable effectiveness of NaI in treating thyroid tumors has shown this "disadvantage" can be turned into an advantage if the reagent has the right combination of affinity and selectivity. If the SHALs are taken up well, target only a specific family of cells (e.g., B lymphocytes and their malignant relatives), bind tightly with low off-rates, and are cleared rapidly from the system, the dose received by normal tissue (relative to malignant) should be substantially lower than that obtained using existing targeting antibodies.

Using established methods (DeNardo et al. (2000) *J. Nucl. Med.,* 41: 952-958; DeNardo et al. (1999) *J. Nucl. Med.,* 40: 1317-1326; DeNardo et al. (1999) *J. Nucl. Med.,* 40: 302-310; Shen et al. (1994) *J. Nucl. Med.,* 35: 1381-1389; Siegel (1994)

*J. Nucl. Med.,* 35: 1213-1216) as guidelines, protocols can readily be developed for conducting pharmacokinetic and radiation dosimetry studies in patients with lymphomatous diseases of the B cell type or other cancers. Projected SHAL dose (mass) levels can be determined using the data generated in mice and adjusted for the relative BSA of mice and patients using known methods (see, e.g., Freireich et al. (1996) *Cancer Chemother. Rep.,* 50: 219-244). In certain embodiments, a protocol is selected that provides the optimal dose level using information on the therapeutic indices for tumor to marrow for a nonmyeloablative strategy and tumor to dose-limiting non-marrow organ for a myeloablative strategy.

J) Optimization of SHAL Affinity, Selectivity and Metabolism by Varying the Linker Length and Linker and Ligand Structure.

SHAL affinity, selectivity and metabolism can be optimized by varying the linker length, and/or the linker and ligand structure, using computer modeling and experimental studies. Linker lengths can be reduced or increased to improve the SHAL's affinity for its target. Changes in the individual ligands used to create the SHAL or alterations in individual ligand structure can also be made to improve binding, target selectivity and optimize the clearance of unbound SHAL from the organism. Modifications in the structure of the linker itself can also be considered to facilitate SHAL clearance, if necessary, from normal tissues and peripheral blood through the incorporation of cleavable bonds (e.g. a peptide or other cleavable linker) that attach the chelator to the SHAL.

If a particular SHAL is observed to exhibit non-specific binding (e.g. to many proteins in the cell extracts or to both Raji and control cells), additional SHALs can be synthesized using different pairs of ligands until a suitably specific SHAL is identified.

1. Maximization of SHAL Binding Affinity for Target Molecule(s).

Binding affinity of multidentate reagents to protein or cell surface targets can be increased by one to several orders of magnitude by changing and optimizing the length of the linker separating the ligands. Without being bound to a particular theory, it is believed that this increase is related to achieving the optimal separation between the ligands to allow them to bind to their individual sites as well as to providing sufficient rotational flexibility within the linker itself to enable the optimal interaction of each ligand within its binding site (e.g. binding pocket).

In certain embodiments, the initial linker length that is chosen for use in the initial SHALs is identified by estimating the distance between the two (or more) bound ligands that are to be linked together. Once it has been determined that a particular combination of linked ligands actually binds to the target, additional modeling can be conducted to further refine the length of the linker and optimize the SHALs binding affinity.

For example, where the target is HLA-DR10, the structure of the HLA-DR10 beta subunit can modeled with both ligands bound in their respective pockets and various length PEG linkers interconnecting the ligands (see, e.g., the Examples herein). From molecular dynamics studies the orientations of the bound ligands can be evaluated to improve the linker design. Further molecular dynamics simulations can be performed to include the linkers and the ligands, thus simulating the polydentate ligands interacting with the target, e.g. as described herein.

Once the results of these modeling experiments are obtained, an additional set of SHALs can be synthesized with linkers spanning the range of sizes predicted to be optimal, and their binding affinities can be experimentally tested.

2. Optimization of Target Selectivity and Metabolism of SHAL.

Computational methods can also be used to determine if changes in the structure of the individual ligands that are linked together to produce the SHAL improve target selectivity and optimize SHAL metabolism and its clearance from normal tissues and peripheral circulation. This can be accomplished, for example, by examining the types of functional groups present inside a targeted binding pocket and their location relative to the bound ligand.

Molecular dynamics studies can be conducted using different conformations of the ligand and selected ligand analogs to aid the identification of ligand derivatives that fit optimally into each binding site (e.g., pocket). Diffusion NMR experiments (Lin et al. (1997) *J. Organic Chem.,* 62: 8930-8931) can be conducted to compare and rank the affinities of a subset of the ligand analogs. The particular analogs chosen for analysis are typically selected based on the results provided by computer modeling and the analog's commercial availability or ease of synthesis. If higher affinity analogs are identified experimentally, a set of new SHALs can be synthesized and tested for their affinity, selectivity in binding to targets, and desirable metabolic properties (e.g., rapid clearance from peripheral circulation, liver and kidney).

In certain embodiments, the small size of the SHAL can result in its being cleared from the tissues too quickly to be effective in delivering a suitable amount of effector to the target cells. If this is observed, various approaches can be used to optimize the retention time of the SHAL in the target tissue. One involves using a biotin attachment site on the linker to add a third ligand that binds to another site on the target. This is expected to increase the affinity of the SHAL to subpicomolar levels and reduce the off-rate of the bound molecule dramatically. Alternatively, the effective size of the SHAL can be increased substantially by attaching it to larger, multi-arm PEG molecules and/or to other molecules.

II. Chimeric Moieties Comprising SHALs (e.g. Cancer Specific SHALs).

The SHALs of this invention are selected to specifically bind to particular targets. Where the targets are markers characteristic of a particular cell type (e.g. a tumor cell) the SHALs can be used to specifically deliver one ore more effectors to the target cell.

In certain embodiments, the SHALs specifically bind to cancer cells. In these embodiments, the SHALs can be used alone as therapeutics (e.g. to inhibit growth and/or proliferation of a cancer cell) and/or they can be coupled to an effector to provide efficient and specific delivery of the effector (e.g. an effector molecule such as a cytotoxin, a radiolabel, etc.) to various cancer cells (e.g., isolated cells, metastatic cells, solid tumor cells, etc.).

In certain preferred embodiments, the SHALs of this invention are utilized in a "pretargeting" strategy (resulting in formation of a chimeric moiety at the target site after administration of the effector moiety) or in a "targeting" strategy where the SHAL is coupled to an effector molecule prior to use to provide a chimeric molecule.

A chimeric molecule or chimeric composition or chimeric moiety refers to a molecule or composition wherein two or more molecules that exist separately in their native state are joined together to form a single molecule having the desired functionality of its constituent molecules. Typically, one of the constituent molecules of a chimeric molecule is a "targeting molecule" in this instance one or more SHALs. The targeting molecule acts to direct the chimeric molecule to its particular target, e.g., a cancer cell.

Another constituent of the chimeric molecule is an "effector". The effector molecule refers to a molecule or group of molecules that is to be specifically transported to the target cell (e.g., a cancer cell). It is noted that in this context, such specific transport need not be exclusively to or into a cancer cell, but merely need to provide preferential delivery of the effector to, or into, the cancer cell as compared to normal healthy cells.

The effector molecule typically has a characteristic activity that is to be delivered to the target cell. Effector molecules include, but are not limited to cytotoxins, labels, radionuclides, ligands, antibodies, drugs, liposomes, nanoparticles, viral particles, cytokines, and the like.

In certain embodiments, the effector is a detectable label, with preferred detectable labels including radionuclides. Among the radionuclides and labels useful in the radionuclide-chelator—(e.g. biotin) conjugates of the present invention, gamma-emitters, positron-emitters, x-ray emitters and fluorescence-emitters are suitable for localization, diagnosis and/or staging, and/or therapy, while beta and alpha-emitters and electron and neutron-capturing agents, such as boron and uranium, also can be used for therapy.

The detectable labels can be used in conjunction with an external detector and/or an internal detector and provide a means of effectively localizing and/or visualizing prostate cancer cells. Such detection/visualization can be useful in various contexts including, but not limited to pre-operative and intraoperative settings. Thus, in certain embodiment this invention relates to a method of intraoperatively detecting cancers in the body of a mammal. These methods typically involve administering to the mammal a composition comprising, in a quantity sufficient for detection by a detector (e.g. a gamma detecting probe), a cancer specific SHAL labeled with a detectable label (e.g. antibodies of this invention labeled with a radioisotope, e.g. $^{161}$Tb, $^{123}$I, $^{125}$I, and the like), and, after allowing the active substance to be taken up by the target tissue, and preferably after blood clearance of the label, subjecting the mammal to a radioimmunodetection technique in the relevant area of the body, e.g. by using a gamma detecting probe.

The label-bound SHAL can be used in the technique of radioguided surgery, wherein relevant tissues in the body of a subject can be detected and located intraoperatively by means of a detector, e.g. a gamma detecting probe. The surgeon can, intraoperatively, use this probe to find the tissues in which uptake of the compound labeled with a radioisotope, that is, e.g. a low-energy gamma photon emitter, has taken place.

In addition to detectable labels, preferred effectors include cytotoxins (e.g. *Pseudomonas* exotoxin, ricin, abrin, *Diphtheria* toxin, and the like), or cytotoxic drugs or prodrugs, in which case the chimeric molecule can act as a potent cell-killing agent specifically targeting the cytotoxin to cancer cells.

In still other embodiments, the effector can include a liposome encapsulating a drug (e.g. an anti-cancer drug such as doxorubicin, vinblastine, taxol, etc.), an antigen that stimulates recognition of the bound cell by components of the immune system, an antibody that specifically binds immune system components and directs them to the cancer, and the like.

A) Certain Preferred Effectors.

1) Imaging Compositions.

In certain embodiments, the chimeric molecules of this invention can be used to direct detectable labels to a tumor site. This can facilitate tumor detection and/or localization. In certain particularly preferred embodiments, the effector component of the chimeric molecule is a "radioopaque" label, e.g. a label that can be easily visualized using x-rays. Radioopaque materials are well known to those of skill in the art. The most common radiopaque materials include iodide, bromide or barium salts. Other radioopaque materials are also known and include, but are not limited to organic bismuth derivatives (see, e.g., U.S. Pat. 5,939,045), radioopaque polyurethanes (see U.S. Pat. 5,346,981, organobismuth composites (see, e.g., U.S. Pat. 5,256,334), radioopaque barium polymer complexes (see, e.g., U.S. Pat. 4,866,132), and the like.

The SHALs of this invention can be coupled directly to the radioopaque moiety or they can be attached to a "package" (e.g. a chelate, a liposome, a polymer microbead, etc.) carrying or containing the radioopaque material as described below.

In addition to radioopaque labels, other labels are also suitable for use in this invention. Detectable labels suitable for use as the effector molecule component of the chimeric molecules of this invention include any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, green fluorescent protein, and the like), radiolabels (e.g., $^{3}$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Various preferred radiolabels include, but are not limited to $^{99}$Tc, $^{203}$Pb, $^{67}$Ga, $^{68}$Ga, $^{72}$As, $^{111}$In, $^{113m}$In, $^{97}$Ru, $^{62}$Cu, 64lCu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

Means of detecting such labels are well known to those of skill in the art. Thus, for example, radiolabels may be detected using photographic film, scintillation detectors, and the like. Fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

2) Radiosensitizers.

In another embodiment, the effector can be a radiosensitizer that enhances the cytotoxic effect of ionizing radiation (e.g., such as might be produced by $^{60}$Co or an x-ray source) on a cell. Numerous radiosensitizing agents are known and include, but are not limited to benzoporphyrin derivative compounds (see, e.g., U.S. Pat. No. 5,945,439), 1,2,4-benzotriazine oxides (see, e.g., U.S. Pat. No. 5,849,738), compounds containing certain diamines (see, e.g., U.S. Pat. No. 5,700,825), BCNT (see, e.g., U.S. Pat. No. 5,872,107), radiosensitizing nitrobenzoic acid amide derivatives (see, e.g., U.S. Pat. No. 4,474,814), various heterocyclic derivatives (see, e.g., U.S. Pat. No. 5,064,849), platinum complexes (see, e.g., U.S. Pat. No. 4,921,963), and the like.

3) Radioisotopes.

In certain embodiments, the effector comprises one or more radioisotopes that when delivered to a target cell bring about radiation-induced cell death.

For medical purposes, the most important types of decay are gamma emission, beta decay, alpha decay, and electron capture. The gamma emitted by a radionuclide, such a $^{131}$I, exits the body, allowing the use of external scintigraphic imaging to determine the biodistribution of radiolabeled antibodies (the optimal energy range for immunoscintigraphy is 100-250 keV). In contrast, beta particles deposit most of their energy within a few millimeters of the point of decay. Beta emissions from radionuclides such as $^{131}$I or $^{90}$Y that have targeted antigen-positive tumor cells can kill nearby antigen-negative tumor cells through a "crossfire" effect.

Yttrium-90, a pure beta emitter, has several properties that make it an attractive choice for radioimmunotherapy: 1) a high beta energy ($E_{max}$=2.29 MeV; maximum range of particulate energy in tissue=11.9 mm) which enables it to kill adjacent tumor cells; 2) metal chemistry, which facilitates the synthesis of radioisotope-antibody conjugates and use of a pretargeting approach; and 3) a sufficiently long physical half-life (2.67 days) for use with intact SHALs, which may take 1-3 days to reach their peak concentration in tumors.

In certain embodiments, the effector can include an alpha emitter, i.e. a radioactive isotope that emits alpha particles and/or an auger-electron emitter. Alpha-emitters and auger-electron emitters have recently been shown to be effective in the treatment of cancer (see, e.g., Bodei et al. (2003) *Cancer Biotherapy and Radiopharmaceuticals,* 18:861). Suitable alpha emitters include, but are not limited $^{212}$Bi, $^{213}$Bi, $^{211}$ At, and the like.

Table 1 illustrates some radionuclides suitable for radioimmunotherapy. This list is intended to be illustrative and not limiting.

5) Chelates

Many of the pharmaceuticals and/or radiolabels described herein are preferably provided as a chelate, particularly where a pre-targeting strategy is utilized. The chelating molecule is typically coupled to a molecule (e.g. biotin, avidin, streptavidin, etc.) that specifically binds an epitope tag attached to a prostate cancer specific antibody of this invention.

Figure 22:
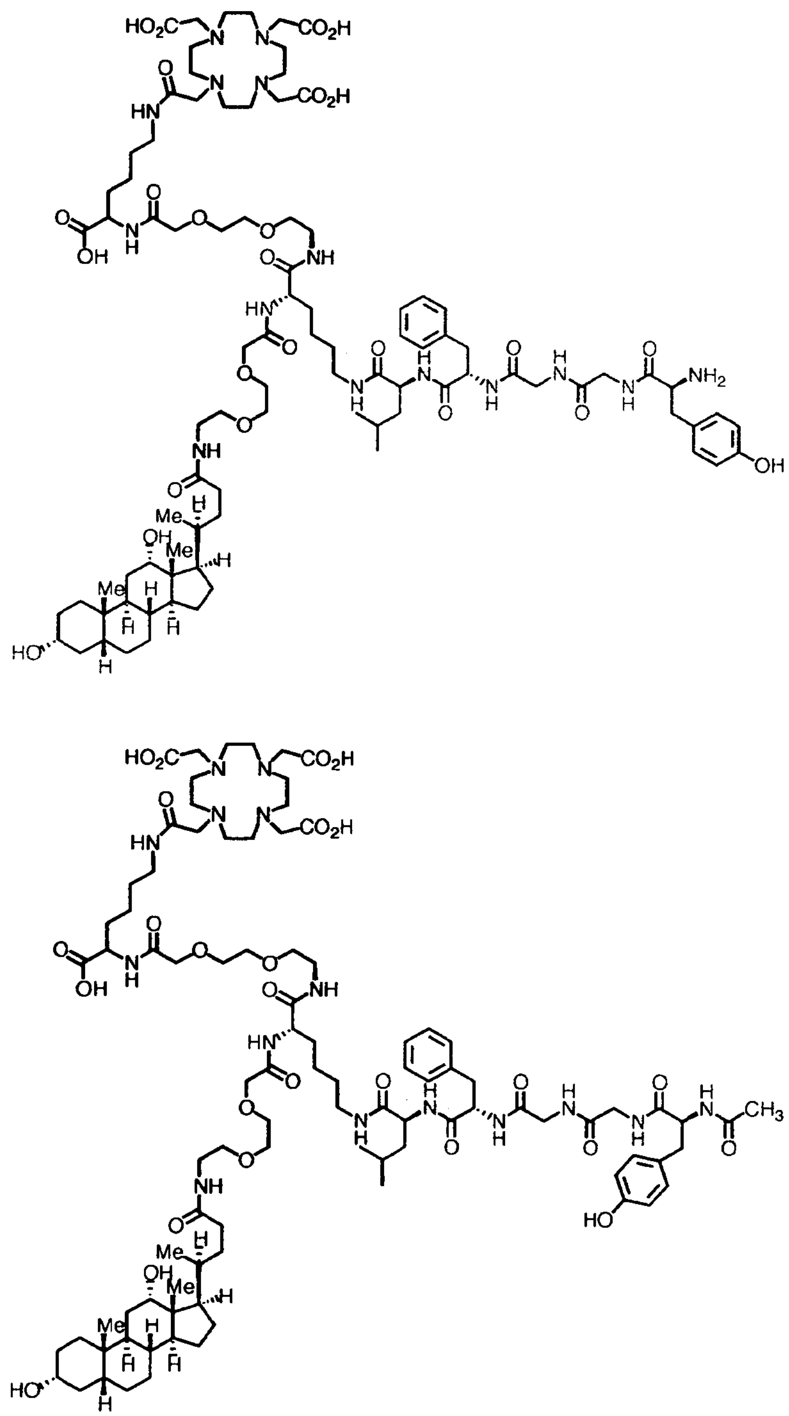
FIG. 22 illustrates SHALs attached to DOTA. The red part is one ligand (deoxycholate), the green is the other ligand (5-leu-enkephalin), the blue is a lysine used to make the shortest linker, and the black is a combination of things: the PEG molecules used to make the linker between the two ligands longer, a DOTA ring attached to the SHAL for binding the radioactive metal.

Chelating groups are well known to those of skill in the art. In certain embodiments, chelating groups are derived from ethylene diamine tetra-acetic acid (EDTA), diethylene triamine penta-acetic acid (DTPA), cyclohexyl 1,2-diamine tetra-acetic acid (CDTA), ethyleneglycol-O,O'-bis(2-aminoethyl)-N,N,N',N'-tetra-acetic acid (EGTA), N,N-bis(hydroxybenzyl)-ethylenediamine-N,N'-diacetic acid (HBED), triethylene tetramine hexa-acetic acid (TTHA), 1,4,7,10-tetraazacyclododecane-N,N'-,N",N'"-tetra-acetic acid (DOTA), hydroxyethyldiamine triacetic acid (HEDTA), 1,4,8,11-tetra-azacyclotetradecane-N,N',N",N'"-tetra-acetic acid (TETA), substituted DTPA, substituted EDTA, and the like (see, e.g., FIG. 22).

Examples of certain preferred chelators include unsubstituted or, substituted 2-iminothiolanes and 2-iminothiacyclohexanes, in particular 2-imino-4-mercaptomethylthiolane.

One chelating agent, 1,4,7,10-tetraazacyclododecane-N, N, N", N'"-tetraacetic acid (DOTA), is of particular interest because of its ability to chelate a number of diagnostically and therapeutically important metals, such as radionuclides and radiolabels.

TABLE 1

Illustrative radionuclides suitable for radioimmunotherapy.

| Radio-nuclide | Decay mode | Physical half life | Max. particulate energy (%) | Advantages | Disadvantages |
|---|---|---|---|---|---|
| I-131 | β, γ | 8 d | 807 keV (1)*<br>606 keV (86)*<br>336 keV (13)* | Iodine chemistry, inexpensive | Dehalogenation, radiation safety concerns |
| Cu-67 | β, γ | 62 h | 577 keV (20)*<br>484 keV (35)*<br>395 keV (45)* | Images, metal chemistry, long retention in tumor | Scarce |
| Lu-177 | β, γ | 6.7 d | 497 keV (90)*<br>384 keV (3)*<br>175 keV (7)* | Images | Scarce, bone seeker |
| Re-186 | β, γ, electron capture | 91 h | 1.07 MeV (77)*<br>934 keV (23)* | $^{99m}$Tc chemistry | Scarce |
| Y-90 | β | 64 h | 2.29 MeV (100)* | Metal chemistry | Doesn't image, bone seeker |
| Re-188 | β | 17 h | 2.13 MeV (100)* | | Scarce, short ½ life |
| Bi-212 | α, β | 1 h | 6.09 MeV (27)**<br>6.05 MeV (70)**<br>5.77 MeV (2)**<br>5.61 MeV (1)** | | Doesn't image, short ½ life, unstable daughter product |
| At-211 | α, electron capture | 7 h | 5.87 MeV (100)** | High RBE, hypoxia less important, short range | Doesn't image, short ½ life, unstable daughter product |
| I-125 | Electron capture | 60 d | 35 keV (100) | Short range | Doesn't image, long ½ life |

*beta irradiation

**alpha irradiation

RBE, relative biologic effectiveness

4) Ligands.

In various embodiments the effector molecule can also be a ligand, an epitope tag, or an antibody. Particularly preferred ligand and antibodies are those that bind to surface markers on immune cells. Chimeric molecules utilizing such antibodies as effector molecules act as bifunctional linkers establishing an association between the immune cells bearing binding partner for the ligand or antibody and the prostate cancer cell(s).

Conjugates of DOTA and proteins such as antibodies have been described. For example, U.S. Pat. No. 5,428,156 teaches a method for conjugating DOTA to antibodies and antibody fragments. To make these conjugates, one carboxylic acid group of DOTA is converted to an active ester which can react with an amine or sulfhydryl group on the antibody or antibody fragment. Lewis et al. (1994) *Bioconjugate Chem.* 5: 565-576, describes a similar method wherein one carboxyl group of DOTA is converted to an active ester, and the activated DOTA is mixed with an antibody, linking the antibody to DOTA via the epsilon-amino group of a lysine residue of the antibody, thereby converting one carboxyl group of DOTA to an amide moiety.

Alternatively, the chelating agent can be coupled, directly or through a linker, to an epitope tag or to a moiety that binds an epitope tag. Conjugates of DOTA and biotin have been described (see, e.g., Su (1995) *J. Nucl. Med.,* 36 (5 Suppl): 154P, which discloses the linkage of DOTA to biotin via available amino side chain biotin derivatives such as DOTA-LC-biotin or DOTA-benzyl-4-(6-amino-caproamide)-biotin). Yau et al., WO 95/15335, disclose a method of producing nitro-benzyl-DOTA compounds that can be conjugated to biotin. The method comprises a cyclization reaction via transient projection of a hydroxy group; tosylation of an amine; deprotection of the transiently protected hydroxy group; tosylation of the deprotected hydroxy group; and intramolecular tosylate cyclization. Wu et al. (1992) *Nucl. Med. Biol.,* 19(2): 239-244 discloses a synthesis of macrocylic chelating agents for radiolabeling proteins with $^{111}$In and $^{90}$Y. Wu et al. makes a labeled DOTA-biotin conjugate to study the stability and biodistribution of conjugates with avidin, a model protein for studies. This conjugate was made using a biotin hydrazide which contained a free amino group to react with an in situ generated activated DOTA derivative.

It is noted that the macrocyclic chelating agent 1,4,7,10-tetraazacyclododecane-N,N',N",N'"-tetraacetic acid (DOTA) binds $^{90}$Y and $^{111}$In with extraordinary stability. Kinetic studies in selected buffers to estimate radiolabeling reaction times under prospective radiopharmacy labeling can be performed to determine optimal radiolabeling conditions to provide high product yields consistent with FDA requirements for a radiopharmaceutical. It is also noted that protocols for producing Yttrium-90-DOTA chelates are described in detail by Kukis et al. (1998) *J. Nucl. Med.,* 39(12): 2105-2110.

6) Cytotoxins.

The SHALs of this invention can be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy a-emitters as described above.

Enzymatically active toxins and fragments. thereof are exemplified by diphtheria toxin A fragment, nonbinding active fragments of diphtheria toxin, exotoxin A (from *Pseudomonas aeruginosa*), ricin A chain, abrin A chain, modeccin A chain, .alpha.-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin, for example.

Particularly preferred cytotoxins include *Pseudomonas* exotoxins, *Diphtheria* toxins, ricin, and abrin. *Pseudomonas* exotoxin A (PE) is an extremely active monomeric protein (molecular weight 66 kD), secreted by *Pseudomonas aeruginosa*, which inhibits protein synthesis in eukaryotic cells through the inactivation of elongation factor 2 (EF-2) by catalyzing its ADP-ribosylation (catalyzing the transfer of the ADP ribosyl moiety of oxidized NAD onto EF-2).

The toxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2, which inactivates the protein and causes cell death. The function of domain Ib (amino acids 365-399) remains undefined, although a large part of it, amino acids 365-380, can be deleted without loss of cytotoxicity (see, e.g., Siegall et al. (1989) *J. Biol. Chem.* 264: 14256-14261).

Where the SHAL is attached to PE, one preferred PE molecule is one in which domain Ia (amino acids 1 through 252) is deleted and amino acids 365 to 380 have been deleted from domain Ib. However all of domain Ib and a portion of domain II (amino acids 350 to 394) can be deleted, particularly if the deleted sequences are replaced with a linking peptide such as GGGGS (SEQ ID NO:3).

In addition, the PE molecules can be further modified using site-directed mutagenesis or other techniques known in the art, to alter the molecule for a particular desired application. Means to alter the PE molecule in a manner that does not substantially affect the functional advantages provided by the PE molecules described here can also be used and such resulting molecules are intended to be covered herein.

For maximum cytotoxic properties of a preferred PE molecule, several modifications to the molecule are recommended. An appropriate carboxyl terminal sequence to the recombinant molecule is preferred to translocate the molecule into the cytosol of target cells. Amino acid sequences which have been found to be effective include, REDLK (SEQ ID NO:4) (as in native PE), REDL (SEQ ID NO:5), RDEL (SEQ ID NO:6), or KDEL (SEQ ID NO:7), repeats of those, or other sequences that function to maintain or recycle proteins into the endoplasmic reticulum, referred to here as "endoplasmic retention sequences". See, for example, Chaudhary et al. (1991) *Proc. Natl. Acad. Sci. USA* 87:308-312 and Seetharam et al, *J. Biol. Chem.* 266: 17376-17381. Preferred forms of PE comprise the PE molecule designated PE38QQR. (Debinski et al. *Bioconj. Chem.,* 5: 40 (1994)), and PE4E (see, e.g., Chaudhary et al. (1995) *J. Biol. Chem.,* 265: 16306).

Methods of cloning genes encoding PE and coupling such cytotoxins to targeting moieties are well known to those of skill in the art (see, e.g., Siegall et al. (1989) *FASEB J.,* 3: 2647-2652; and Chaudhary et al. (1987) *Proc. Natl. Acad. Sci. USA,* 84: 4538-4542, and references therein).

Like PE, diphtheria toxin (DT) kills cells by ADP-ribosylating elongation factor 2 thereby inhibiting protein synthesis. Diphtheria toxin, however, is divided into two chains, A and B, linked by a disulfide bridge. In contrast to PE, chain B of DT, which is on the carboxyl end, is responsible for receptor binding and chain A, which is present on the amino end, contains the enzymatic activity (Uchida et al. (1972) *Science,* 175: 901-903; Uchida et al. (1973) *J. Biol. Chem.,* 248: 3838-3844).

In a preferred embodiments, the SHAL-*Diphtheria* toxin chimeric molecules of this invention have the native receptor-binding domain removed by truncation of the *Diphtheria* toxin B chain. Particularly preferred is DT388, a DT in which the carboxyl terminal sequence beginning at residue 389 is removed. Chaudhary et al. (1991) *Bioch. Biophys. Res. Comm.,* 180: 545-551. Like the PE chimeric cytotoxins, the DT molecules can be chemically conjugated to the prostate cancer specific antibody, but, in certain preferred embodiments, the antibody will be fused to the Diphtheria toxin by recombinant means (see, e.g., Williams et al. (1990) *J. Biol. Chem.* 265: 11885-11889).

7) Viral Particles.

In certain embodiments, the effector comprises a viral particle. The SHAL can be conjugated to the viral particle e.g. via a protein expressed on the surface of the viral particle (e.g. a filamentous phage). The viral particle can additionally include a nucleic acid that is to be delivered to the target (prostate cancer) cell. The use of viral particles to deliver nucleic acids to cells is described in detail in WO 99/55720.

8) Other Therapeutic Moieties.

Other suitable effector molecules include pharmacological agents or encapsulation systems containing various pharmacological agents. Thus, the SHAL can be attached directly to a drug that is to be delivered directly to the tumor. Such drugs are well known to those of skill in the art and include, but are not limited to, doxorubicin, vinblastine, genistein, an antisense molecule, and the like.

Alternatively, the effector molecule can comprise an encapsulation system, such as a viral capsid, a liposome, or micelle that contains a therapeutic composition such as a drug, a nucleic acid (e.g. an antisense nucleic acid or another nucleic acid to be delivered to the cell), or another therapeutic moiety that is preferably shielded from direct exposure to the circulatory system. Means of preparing liposomes attached to antibodies are well known to those of skill in the art (see, for example, U.S. Pat. No. 4,957,735, Connor et al. (1985) *Pharm. Ther.,* 28: 341-365) and similar methods can be used for coupling SHALs.

B) Attachment of the SHAL to the Effector.

One of skill will appreciate that the SHALs of this invention and the effector molecule(s) can be joined together in any order. Thus, in various embodiments, the effector can be attached to any ligand comprising the SHAL and/or to the linker joining the various ligands comprising the SHAL.

The SHAL and the effector can be attached by any of a number of means well known to those of skill in the art. Typically the effector is conjugated, either directly or through a linker (spacer), to the SHAL.

In one embodiment, the SHAL is chemically conjugated to the effector molecule (e.g., a cytotoxin, a label, a ligand, or a drug or liposome, etc.). Means of chemically conjugating molecules are well known to those of skill.

The procedure for attaching an effector to a SHAL will vary according to the chemical structure of the effector and/or the SHAL. The ligands comprising the SHAL and/or the linker joining the ligands can contain a variety of functional groups; e.g., carboxylic acid (COOH), free amine (—$NH_2$), hydroxyl (—OH), thiol (—SH), and other groups, that are available for reaction with a suitable functional group on an effector molecule or on a linker attached to an effector molecule to effectively bind the effector to the SHAL.

Alternatively, the ligand(s) comprising the SHAL and/or the linker joining the ligands can be derivatized to expose or attach additional reactive functional groups. The derivatization can involve attachment of any of a number of linker molecules such as those described above for coupling the ligands to each other.

In some circumstances, it is desirable to free the effector from the SHAL when the chimeric molecule has reached its target site. Therefore, chimeric conjugates comprising linkages that are cleavable, e.g., in the vicinity of the target site can be used when the effector is to be released from the SHAL. Cleaving of the linkage to release the agent from the antibody may be prompted by enzymatic activity or conditions to which the conjugate is subjected, e.g., either inside the target cell or in the vicinity of the target site. When the target site is a tumor, a linker which is cleavable under conditions present at the tumor site (e.g. when exposed to tumor-associated enzymes or acidic pH) may be used.

In certain instances, the cleavable linker can be a peptide that can be subject to proteolysis. In certain embodiments, the cleavable linker comprises a peptide having a recognition site for a protease.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient=s complement system. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

2 Conjugation of Chelates.

In certain preferred embodiments, the effector comprises a chelate that is attached to an antibody or to an epitope tag. The cancer specific SHAL bears a corresponding epitope tag or antibody so that simple contacting of the SHAL to the chelate results in attachment of the SHAL to the effector. The combining step can be performed before the moiety is used (targeting strategy) or the target tissue can be bound to the SHAL before the chelate is delivered. Methods of producing chelates suitable for coupling to various targeting moieties are well known to those of skill in the art (see, e.g., U.S. Pat. Nos. 6,190,923, 6,187,285, 6,183,721, 6,177,562, 6,159,445, 6,153,775, 6,149,890, 6,143,276, 6,143,274, 6,139,819, 6,132,764, 6,123,923, 6,123,921, 6,120,768, 6,120,751, 6,117,412, 6,106,866, 6,096,290, 6,093,382, 6,090,800, 6,090,408, 6,088,613, 6,077,499, 6,075,010, 6,071,494, 6,071,490, 6,060,040, 6,056,939, 6,051,207, 6,048,979, 6,045,821, 6,045,775, 6,030,840, 6,028,066, 6,022,966, 6,022,523, 6,022,522, 6,017,522, 6,015,897, 6,010,682, 6,010,681, 6,004,533, 6,001,329, and the like).

III. SHALs that Inhibit Receptors, Enzymes and Other Biomolecules.

In certain embodiments, this invention provides SHALs that inhibit the activity of enzymes, receptors, or the activity of other biomolecules. Typically such SHALs comprise ligands that bind to different sites around or near the active site or binding site of the enzyme or receptor. In certain embodiments, the ligands are selected to bind to a first pocket and a second pocket in the enzyme, receptor, or other binding protein where the first and second pocket flank opposite sides of the active site or biding site of said enzyme, receptor, or other binding protein or the first pocket comprises or is located in active site and second pocket is located nearby/adjacent to the first pocket or either or both pockets are located in or sufficiently near the site used by the protein, enzyme, or receptor for binding to another molecule such that the binding of a ligand in either or both pockets disrupts or blocks the binding of the enzyme, receptor, or other biomolecule to its cognate ligand. When the SHAL is contacted with its target, it binds to the target effectively blocking the active site and/or binding site thereby inhibiting the activity of the enzyme, receptor or other biomolecule.

IV) Pharmaceutical Compositions.

The SHALs, and/or chelates, and/or chimeric molecules of this invention (particularly those specific for cancer or other pathologic cells) are useful for parenteral, topical, oral, or local administration (e.g. injected into a tumor site), aerosol administration, or transdermal administration, for prophylactic, but principally for therapeutic treatment. The pharmaceutical compositions can be administered in a variety of unit dosage forms depending upon the method of administration. For example, unit dosage forms suitable for oral administration include powder, tablets, pills, capsules and lozenges. It is recognized pharmaceutical compositions of this invention, when administered orally, can be protected from digestion. This is typically accomplished either by complexing the active component (e.g. the SHAL, the chimeric molecule, etc.) with a composition to render it resistant to acidic and enzymatic hydrolysis or by packaging the active ingredient(s) in an appropriately resistant carrier such as a liposome. Means of protecting components from digestion are well known in the art.

The pharmaceutical compositions of this invention are particularly useful for parenteral administration, such as intravenous administration or administration into a body cavity or lumen of an organ. The compositions for administration will commonly comprise a solution of the SHAL and/or chimeric molecule dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of chimeric molecule in these formulations can vary widely, and will be selected primarily based on fluid volumes, viscosities, body weight and the like in accordance with the particular mode of administration selected and the patient's needs.

Thus, a typical pharmaceutical composition for intravenous administration would be about 0.1 to 10 mg per patient per day. Dosages from 0.1 up to about 100 mg per patient per day may be used, particularly when the drug is administered to a secluded site and not into the blood stream, such as into a body cavity or into a lumen of an organ. Actual methods for preparing parenterally administrable compositions will be known or apparent to those skilled in the art and are described in more detail in such publications as *Remington's Pharmaceutical Science,* 15th ed., Mack Publishing Company, Easton, Pa. (1980).

The compositions containing the present SHALs and/or chimeric molecules or a cocktail thereof (i.e., with other therapeutics) can be administered for therapeutic treatments. In therapeutic applications, compositions are administered to a patient suffering from a disease, e.g., a cancer, in an amount sufficient to cure or at least partially arrest the disease and its complications. An amount adequate to accomplish this is defined as a "therapeutically effective dose." Amounts effective for this use will depend upon the severity of the disease and the general state of the patient's health.

Single or multiple administrations of the compositions may be administered depending on the dosage and frequency as required and tolerated by the patient. In any event, the composition should provide a sufficient quantity of the SHALs of this invention to effectively treat the patient.

It will be appreciated by one of skill in the art that there are some regions that are not heavily vascularized or that are protected by cells joined by tight junctions and/or active transport mechanisms which reduce or prevent the entry of macromolecules present in the blood stream One of skill in the art will appreciate that in these instances, the therapeutic compositions of this invention can be administered directly to the tumor site. Thus, for example, brain tumors can be treated by administering the therapeutic composition directly to the tumor site (e.g., through a surgically implanted catheter).

Alternatively, the therapeutic composition can be placed at the target site in a slow release formulation. Such formulations can include, for example, a biocompatible sponge or other inert or resorbable matrix material impregnated with the therapeutic composition, slow dissolving time release capsules or microcapsules, and the like.

Typically the catheter or time release formulation will be placed at the tumor site as part of a surgical procedure. Thus, for example, where major tumor mass is surgically removed, the perfusing catheter or time release formulation can be emplaced at the tumor site as an adjunct therapy. Of course, surgical removal of the tumor mass may be undesired, not required, or impossible, in which case, the delivery of the therapeutic compositions of this invention may comprise the primary therapeutic modality.

V. Kits.

Where a radioactive, or other, effector is used as a diagnostic and/or therapeutic agent, it is frequently impossible to put the ready-for-use composition at the disposal of the user, because of the often poor shelf life of the radiolabeled compound and/or the short half-life of the radionuclide used. In such cases the user can carry out the labeling reaction with the radionuclide in the clinical hospital, physician's office, or laboratory. For this purpose, or other purposes, the various reaction ingredients can then be offered to the user in the form of a so-called "kit". The kit is preferably designed so that the manipulations necessary to perform the desired reaction should be as simple as possible to enable the user to prepare from the kit the desired composition by using the facilities that are at his disposal. Therefore the invention also relates to a kit for preparing a composition according to this invention.

Such a kit according to the present invention preferably comprises a SHAL as described herein. The SHAL can be provided, if desired, with inert pharmaceutically acceptable carrier and/or formulating agents and/or adjuvants is/are added. In addition, the kit optionally includes a solution of a salt or chelate of a suitable radionuclide (or other active agent), and (iii) instructions for use with a prescription for administering and/or reacting the ingredients present in the kit.

The kit to be supplied to the user may also comprise the ingredient(s) defined above, together with instructions for use, whereas the solution of a salt or chelate of the radionuclide which can have a limited shelf life, can be put to the disposal of the user separately.

The kit can optionally, additionally comprise a reducing agent and/or, if desired, a chelator, and/or instructions for use of the composition and/or a prescription for reacting the ingredients of the kit to form the desired product(s). If desired, the ingredients of the kit may be combined, provided they are compatible.

In certain embodiments, the complex-forming reaction with the SHAL can simply be produced by combining the components in a neutral medium and causing them to react. For that purpose the effector may be presented to the SHAL in the form of a chelate.

When kit constituent(s) are used as component(s) for pharmaceutical administration (e.g. as an injection liquid) they are preferably sterile. When the constituent(s) are provided in a dry state, the user should preferably use a sterile physiological saline solution as a solvent. If desired, the constituent(s) can be stabilized in the conventional manner with suitable stabilizers, for example, ascorbic acid, gentisic acid or salts of these acids, or they may comprise other auxiliary agents, for example, fillers, such as glucose, lactose, mannitol, and the like.

While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Creation of HLA-DR10 Specific SHALs

Preclinical and clinical studies have revealed that the epitopic region (unique region recognized by antibodies) on the beta subunit of HLA-DR 10, and related HLA-DR major histocompatibility cell surface proteins, are particularly attractive targets for systemic radioisotopic therapy for B-cell lymphomas and leukemias and provide other opportunities for cancer treatment and prevention. Although HLA-DR 10 has characteristics in common with other B-cell surface proteins, like CD20, that make it a suitable target, it has disparate characteristics that we believe provide great attractiveness.

In common with CD20 antigen, the HLA-DR 10 protein is located on the surface of B lymphocytes, persists through B-cell differentiation, but disappears during transformation of the lymphocyte to the plasma cell stage (Epstein et al. (1987) *Cancer Res.,* 47: 830-840). The discrete Lym-1 antigen epitope appears on committed B-cell precursors, but is not expressed earlier during B-cell development. In addition, it is not generally found on T cells or other normal cells. Expression of class 2 MHC molecules on B-cells is developmentally controlled. Early and pre-B-cells are class 2 mRNA negative and cannot be induced to express class 2 antigens. HLA-DR antigen is acquired during the late pre-B-cell stage. Because the basal level of class 2 expression on B-cells is about 100 times lower than that found on malignant B-cell lines (Rose et al. (1996) *Cancer Immunol Immunother.,* 43: 26-30.; Rose et al. (1999) *Mol Immunol.,* 36: 789-797), this provides an explanation for the observation that only 5 mg of Lym-1 antibody is needed to target extravascular malignant lymphoma (DeNardo et al. (1998) *J Clin Oncol.,* 16: 3246-3256), whereas 50 mg of CD22 and hundreds of mg of CD20 antibodies are required due to the density of CD22 and CD20 antigens on normal lymphocytes (Press (1999) *Semin Oncol.,* 26: 58-65; Knox et al. (1996) *Clin Cancer Res.,* 2: 457-470). Treatment doses of iodine-131, copper-67, or yttrium-90 attached to small amounts of Lym-1 cures most mice with Raji xenografts (DeNardo et al. (1991) *Antibody Immunoconj Radiophar.,* 4: 777-785; DeNardo et al. (1997) *Clin Cancer Res.,* 3:71-79), the human Burkitt's malignant lymphoma cell line used as the immunogen to generate Lym-1 (Epstein et al. (1987) *Cancer Res.,* 47: 830-840). Similarly, these radiopharmaceuticals, in Phase I/II trials in patients with B-cell non-Hodgkin's lymphoma and a subset of patients with chronic lymphocytic leukemia, have induced a high and durable response rate, with frequent complete remissions and some long-term survivals when used as single agent therapy. HLA-DR provides cell identification, and antigenic peptides are displayed on HLA-DR. This may explain unusually long survivals in a subset of our patients with aggressive lymphoma in whom an idiotypic antibody cascade, including human polyclonal antibodies cytotoxic for Raji cells and Raji tumors, has been documented (DeNardo et al. (1998) *Cancer Biother Radiopharm.,* 13: 1-12; Lamborn et al. (1997) *Clin Cancer Res.,* 3: 1253-1260).

However, as well as these antibodies work, there is still a need to improve upon them. The antibody is a macromolecule that penetrates vascular barriers and the tumor poorly and interacts with a variety or receptors, which limits their selectivity as radioisotope carriers and adds to the adverse event profile. The immunogenicity of antibody-based reagents can be minimized, but not eliminated, using "humanized" antibodies (Brown et al. (2001) *Clin Lymphoma.,* 2: 188-90; Kostelny et al. (2001) *Int J Cancer,* 93: 556-65; Leonard et al. (2002) *Semin Oncol.,* 29: 81-6; Lundin et al. (2002) *Blood,* 100: 768-73; Ligibel and Winer (2002) *Semin Oncol.,* 29: 38-43). Immunogenicity may be avoided by creating non-protein based reagents. Whole antibodies also exhibit appreciable reactivity (e.g., Fc interactions) with non-target cells that reduces selectivity and increases adverse events. Even small improvements in the targeting agent's selectivity can be used to minimize collateral damage and enhance the drug's therapeutic index.

Lym-1 is a murine IgG-2a monoclonal antibody (MAb) that selectively binds a protein highly expressed on the surface of malignant human B-cells (Epstein et al. (1987) *Cancer Res.,* 47: 830-840). We have shown that a discrete epitope on HLA-DR 10 was the original antigen in Raji cells that generated the Lym-1 MAb, and this epitope is not shared by all HLA-DR subtypes (Rose et al. (1996) *Cancer Immunol Immunother.,* 43: 26-30; Rose et al. (1999) *Mol Immunol.,* 36: 789-797). Our data suggest that the critical Lym-1 binding residues are contained in the 19 differences in amino acid sequence between the reactive HLA-DR 10 beta subunit and the unreactive, largely identical HLA-DR 3 and HLA-DR 52 beta subunits. This serves as the basis for the selectivity of the Lym-1 epitope or binding site among HLA-DR containing white blood cells, yet provides the basis for the existence of this protein in virtually all patients with malignant B-cells. Of the 19 residues comprising the critical Lym-1 binding region, only the amino acids Q70 or R70, followed by R71 were found in all Lym-1 reactive specimens and were absent in Lym-1 unreactive specimens. In many of the unreactive HLA-DR molecules, these two residues were often replaced by D70 and/or E71. The hypothesis that the subtypes containing the putative critical Lym-1 binding residues (Q/R70-R71) would be most reactive has been confirmed in a series of studies including extensive cytotoxicity assays conducted in lymphoblastoid cell lines of B and T cell type, incorporating 31 HLA-DR genotypes (Rose et al. (1999) *Mol Immunol.,* 36: 789-797). All the strongly reactive cells expressed at least one Q/R70-R71-containing HLA-DR allele while none of the least reactive cell lines expressed that sequence at position 70-71 of the beta chain. Cytotoxicity assays also showed that the former were dramatically more affected than the latter (Id.). Although Lym-1 reacted with peripheral blood lymphocytes from healthy donors, the avidities were much lower, consistent with a lower HLA-DR protein density on normal lymphocytes and the hypothesis that univalent rather than bivalent binding may occur, further explaining the selectivity of Lym-1 for malignant cells in patients with lymphoma (Id.). Thus, it seems that both the critical Lym-1 glutamine/arginine residues and a threshold antigen density contribute to the selectivity of Lym-1 binding to malignant B-cells over normal lymphocytes. In any event, the data confirm that Lym-1 binds preferentially to lymphoblastoid cells over normal PBLs, thereby providing an attractive difference from other malignant B-cell targeting proteins (Id.).

Our experience with CMRIT has led us to appreciate the complexities of implementation and to realize that many patients with advanced NHL are ineligible for BMT because of their disease and insufficient marrow harvest. For these reasons and because of unique opportunities to dose intensify using novel approaches to develop targeting molecules that can dramatically improve the therapeutic index, we have developed high affinity ligands (SHALs) that mimic $^{131}$I-iodide in thyroid cancer. $^{131}$I-iodide in thyroid cancer, the prototype for radioisotopic molecular targeted systemic radiotherapy, has led to cure of otherwise incurable thyroid cancer because the $^{131}$I is rapidly trapped and retained by the cancer or excreted in the urine, providing a therapeutic index approaching infinity and the opportunity to administer almost unlimited radioisotope without significant toxicity.

We believe that small molecule SHALs can better fulfill the potential of "RIT", and represent a natural extension of our ongoing translational activities involving HLA-DR as a target for radioisotopic carrier molecules to deliver systemic radiotherapy. As described below, we have synthesized a number of bidentate SHALs and determined that at least one of these SHALs binds to isolated HLA-DR10.

A) Development of a Computer Model of the Molecular Structure of the HLA-DR 10 Beta Subunit Containing the Region Shown to be Critical for Lym-1 Antibody Binding to Malignant B Cells and Compare the Structure with Other HLA-DR Molecules.

Crystal structures for four different closely related HLA-DR molecules (HLA-DR 1-4) have been determined previously and deposited in the PDB structure database by others (Jardetzky et al. (1994) *Nature,* 368:711-718; Bolin et al. (2000) *J. Med. Chem.,* 43:2135-2148; Smith et al. (1998) *J. Exp. Med.,* 188:1511-1520; Ghosh et al. (1995) *Nature,* 378: 457-462). Protein sequences for these four proteins, HLA-DR1, HLA-DR2, HLA-DR3 and HLA-DR4, were aligned with the HLA-DR10 sequence and compared to identify both the locations of the variable amino acids and those regions of the HLA-DR10 molecule containing the amino acid residues that had been identified as the critical epitope of the Lym-1 antibody (Rose et al. (1996) *Cancer Immunol Immunother.,* 43: 26-30; Rose et al. (1999) *Mol Immunol.,* 36: 789-797). This alignment revealed that all five proteins exhibit such a high degree of sequence similarity (FIG. 8) that we were able to create a sufficiently accurate 3-D model of the HLA-DR10 beta subunit by homology modeling and use the coordinates of the model to screen for ligand binding using the program DOCK.

Two different approaches were used to create models of the HLA-DR10 beta subunit for use in ligand docking. The first approach used the coordinates of the entire structure of HLA-DR3 as the template for creating the homology model, and the nineteen amino acids that differed between HLA-DR3 and HLA-DR10 were mutated (changed) in the HLA-DR3 sequence. The coordinates of the amino-terminal four amino acids, which are present in HLA-DR10, HLA-DR1 and HLA-DR2 but absent in HLA-DR3, were obtained from the HLA-DR1 structure and used to complete the model. In the second approach, a hybrid model was generated using the atomic coordinates obtained from different segments of the HLA-DR 1, HLA-DR2 and HLA-DR4 crystal structures. The particular segments of the three HLA crystal structures used in the model were selected based on similarities in their secondary structural elements. Sequence-structure alignments were generated using the Smith-Waterman (Smith and Waterman (1981) *J. Mol. Biol.,* 147:195-197), FASTA (Pearson (1991) *Genomics,* 11: 635-650), BLAST and PSI-BLAST (Altschul et al.(1997) *Nucleic Acids Res.,* 25: 3389-3402) algorithms, and the backbone of the model was created automatically using the AS2TS system (see http://sb9.llnl.gov/adamz/LGA/AL2TS/as2ts.html website). The coordinates for the amino terminal four residues of the structure were taken from the 1seB crystal structure of HLA-DR1, residues 5-122 were obtained from the 1aqd structure of HLA-DR1, residues 123-170 were taken from the 1d5m HLA DR4 structure, and the remaining residues (aa171-193) were obtained from the 1bx2 structure of HLA-DR2. The construction of the terminal regions and loops, amino acid insertions and deletions, and template-model structure comparisons were performed using the LGA program developed at LLNL. The majority of the side chain atom's coordinates were incorporated from the four structural templates (listed above) due to their high level of homology. The side chains in selected regions of the protein model were built using the SCWRL program (Id.). Energy minimization was performed on both structures to eliminate inappropriate side chain contacts and the resulting structures were "optimized" using molecular dynamics.

Figure 9:
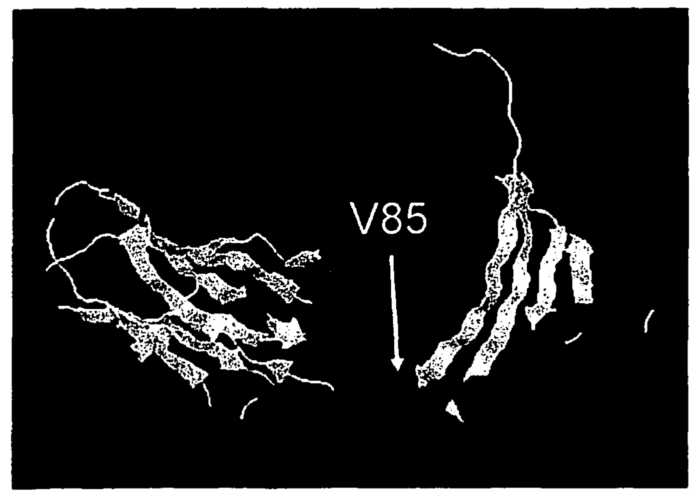
FIG. 9 Homology model of beta subunit of HLA-DR10 showing the two structural domains (See Appendix for color).

Analyses of the resulting models revealed the two approaches yielded structures that were remarkably similar. Extended molecular dynamics runs appeared to provide little additional improvements. The results of the modeling revealed that the structure of the HLA-DR10 molecule is comprised of two domains linked by a hinge with one of the Lym-1 reactive residues, V85, positioned directly adjacent to the hinge (FIG. 9).

Figure 10:
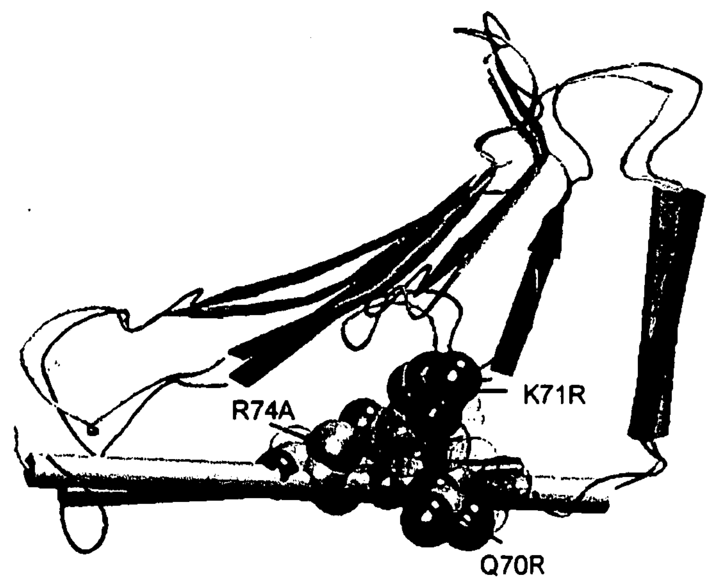
FIG. 10 shows superposition of HLA-DR3 crystal structure (light blue, transparent atoms) and homology model of HLA-DR10 (dark blue, solid atoms) showing the structural similarity in the region of the beta subunit that comprises the Lym-1 epitope. The amino acid residues critical for Lym-1 binding are shown as space filling atoms.

The majority of the core of the relaxed structure of HLA-DR10, when compared with the HLA-DR3 crystal structure, was found to be essentially identical (FIG. 10). The other three amino acids that were observed to play a role in Lym-1 binding, R70, R71 and A74 (A or E at this position appears important for Lym-1 binding), are all located on the exposed surface of a long alpha helix (FIGS. 9 and 10) located immediately adjacent to the hinge B) Identification of Unique Sites on the Surface of HLA-DR10 Within the Lym-1 Epitope that can be Targeted for Ligand Binding.

Figure 11:
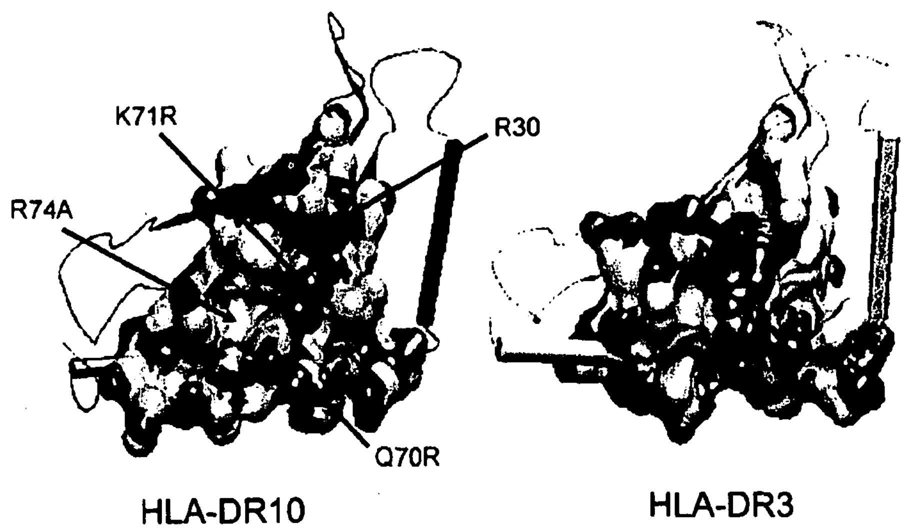
FIG. 11 shows surface plots of HLA-DR10 and HLA-DR3 beta subunits showing differences in the structure of the "pockets" in the region of the protein that comprises the Lym-1 epitope. Charge distribution is shown as dark blue (positive or basic), red (negative or acidic) and light blue (neutral or hydrophobic). The sulfur atom in cysteine is shown in yellow.

Solvent accessible surfaces of the HLA-DR10 protein and the crystal structure of HLA-DR3 were calculated using the atomic coordinates obtained for HLA-DR3 from the Protein Data Bank and our HLA-DR10 model. The site surrounding the three key amino acids in the Lym-1 epitope (within 6A) were examined and compared. As shown in FIG. 11, these three amino acid changes in the HLA-DR10 sequence (Q70R, K71R, and R74A) change both the charge distribution and topography of the protein's exposed surface in this region.

A program developed to identify "pockets" on the surface of the protein (SPHGEN) was used to identify potential cavities that could be targeted for ligand binding. Details of the programs used are described in Example 2. Two adjacent pockets (cavities) in the modeled HLA-DR10 surface were selected as appropriate sites for ligand binding (FIG. 12), based on their proximity to each other, the three Lym-1 reactive residues, and the uniqueness of the amino acids lining the pocket. An examination of the crystal structures of the other four HLA-DR molecules also showed that pockets exist at or in the near vicinity of these sites in each HLA-DR molecule, but as expected (based on the amino acid sequence differences in the peptide chains in this region of the HLA-DR structure) the pockets present on each HLA-DR differ in size, shape, and distance separating them. Since the amino acid "landscape" surrounding these two sites differs significantly in HLA-DR3 and HLA-DR10, docking runs performed at both sites would be expected to identify ligands that bind selectively to the pockets on HLA-DR10 but not to HLA-DR3. These sites, identified as Site 1 and Site 2 and shown filled with red and blue spheres in FIG. 12, flank both sides of the most important amino acid in the Lym-1 epitope, R70. A third unique site, which can be targeted as a backup if suitable ligands cannot be identified that bind to Site 1 or Site 2, has also been located and characterized.

C) Computationally Screening a "Virtual" Ligand Library to Identify Small Molecules that May Bind to Specific Pockets on HLA-DR10 Encompassing the Lym-1 Epitope.

Figure 12:
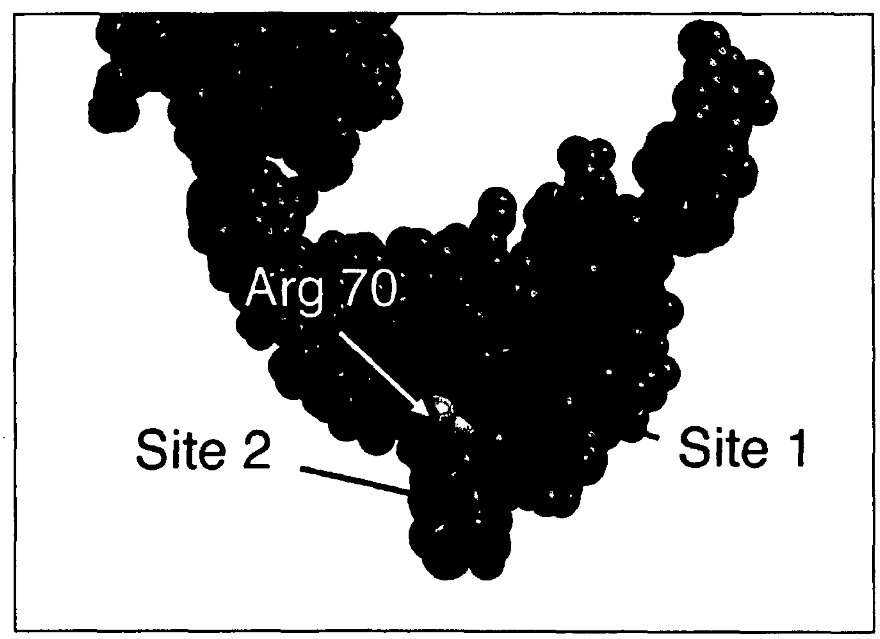
FIG. 12 illustrates the location of two "pockets", designated Site 1 (red) and Site 2 (blue), that surround the amino acids critical for Lym-1 binding (yellow) on the β-subunit of HLA-DR10. These two sites were targeted for ligand binding and used in the computational docking studies.

The program DOCK (UCSF) was used to perform a "virtual" screen of the Available Chemical Directory database of small molecules to identify the top ranked 1,000 molecules predicted to bind in the two unique pockets identified as Site 1 and Site 2 (FIG. 12). Details of the computational docking procedures are described in Example 2.

The top ranked 2,500 molecules were then visually inspected to select down to thirty-five molecules for experiment binding assays (Table 2). This final selection process was based on chemical properties including hydrophobic interactions, hydrogen bonding, and molecular size, and well as practical criteria including commercial availability and cost, ease of synthetic linkage, the overall structural diversity of the set of molecules.

TABLE 2

Ligands predicted to bind to Site 1 on the beta subunit of HLA-DR10 by computational docking

| No. | Compound |
|---|---|
| 1. | 7-Amino-4-chloromethylcoumarin, glycyl-l-proline amide, hydrochloride |
| 2. | 5-([4,6-Dichlorotriazin-2-yl]amino)-fluorescein hydrochloride |
| 3. | 2-[2-[3-Chloro-5-(trifluoromethyl)-2-pyridinyl]carbohydrazonoyl]benzene carboxylic acid |
| 4. | 4-[[2-(4-Cyano-3-phenyl-5-isoxazolyl)vinyl]amino]benzenecarboxylic acid |
| 5. | 4-[2-(2,4-Dichlorophenyl)hydrazino]-4-oxo-2-phenyl-2-butenoic acid |
| 6. | 3-(2-[[3-Chloro-5-(trifluoromethyl)-2-pyridinyl]oxy]anilino)-3-oxopropanoic acid |
| 7. | 3-[(4-Chlorobenzyl)thio]imidazo[1,5-a]pyridine-1-carboxylic acid |
| 8. | 2-[([1,1'-Biphenyl]-4-ylamino)carbonyl]benzoic acid |
| 9. | Bis[4-(3-aminophenoxy)phenyl]sulfone |
| 10. | 4,4'-Bis(4-aminophenoxy)biphenyl |
| 11. | 5(6)-Carboxytetramethylrhodamine n-succinimidyl ester |
| 12. | 1,4-Phenylenebis[[4-(4-aminophenoxy)phenyl]methanone] |
| 13. | H-Tyr(Br-Z)-OEt |
| 14. | '7-Amino-4-chloromethylcoumarin, l-alanyl-l-proline amide, hydrochloride |
| 15. | '5-(N'-[2-aminoethyl]thioureidofluorescein) |
| 16. | Achatin I, Ammonium salt |
| 17. | Fmoc-Asp(OBzl)-OH |
| 18. | Fmoc-Bip-OH |
| 19. | Menai H535 |
| 20. | 2'-Methoxy-5'-methyl-3,4,5,6-tetrachloro-phthalanilic acid |
| 21. | 4-Dimethylaminoazobenzene-4'-sulfonyl-l-valine |
| 22. | Bigchap |
| 23. | Arg-gly-asp-thr (SEQ ID NO: 8) |
| 24. | n-Allyl-2-[(1-benzyl-2-oxo-1,2-dihydro-3-pyridinyl)carbonyl]-1-hydrazinecarbothioamide |
| 25. | n'-Methoxy-n-[7-(4-phenoxyphenyl)[1,2,4]triazolo[1,5-a]pyrimidin-2-yl]iminoformamide |
| 26. | n-[[6-(4-Chlorophenoxy)-3-pyridyl]carbonyl]-n'-[3-(trifluoromethyl)phenyl]urea |
| 27. | n-[[6-(4-Chlorophenoxy)-3-pyridyl]carbonyl]-n'-(4-chlorophenyl)urea |
| 28. | n,n'-Diphenylbenzidine |
| 29. | Rcl s16,963-3 |
| 30. | N,N'-bis-(4-amino-2-chloro-phenyl)-terephthal-amide4-[[5-(trifluoromethyl)pyridin-2-yl]oxy]phenyl N-phenylcarbamate |
| 31. | Methidiumpropyl ethylenediame tetraacetic acid |
| 32. | N-(4-[[3-Chloro-5-(trifluoromethyl)-2-pyridinyl]methyl]phenyl)-4-iodobenzenecarboxamide |
| 33. | 2-(4-Chlorophenyl)-2-[6-[(4-chlorophenyl)sulfanyl]-3-pyridazinyl]acetamide |
| 34. | 6-Chloro-n4-(4-phenoxyphenyl)-2,4-pyrimidinediamine |
| 35. | 4-Amino-2-anilino-5-benzoyl-3-thiophene-carbonitrile |

This procedure was repeated for identification of thirty-five potential binders for Site 2. Table 3 lists those ligands predicted by molecular docking to bind to Site. 2.

TABLE 3

Ligands predicted to bind to Site 2 on the beta subunit of HLA-DR10 by computational docking

| No. | Compound |
|---|---|
| 1. | Leu-enkephalin |
| 2. | 4-[4-(4-Chlorobenzyl)piperazino]-3-nitrobenzenecarboxylic acid |
| 3. | Beta-casomorphin (1-2) |
| 4. | L-Aspartic acid, alpha-(4,5-dimethoxy-2-nitrobenzyl) ester, hydrochloride |

TABLE 3-continued

| Ligands predicted to bind to Site 2 on the beta subunit of HLA-DR10 by computational docking | |
|---|---|
| 5. | Cefadroxil |
| 6. | 3,3',5-Triiodo-dl-thyronine |
| 7. | H-Glu(anilide)-OH |
| 8. | H-Trp-phe-OH |
| 9. | Glycylglycyl-D,L-phenylalanine |
| 10. | Thymopoietin II(33-36) |
| 11. | Thiophosphoric acid S-(3-(3-amino-propylamino)-propyl) ester, di-hydrate |
| 12. | Dynorphin A (13-17), Porcine |
| 13. | l-Alanyl-l-alanyl-l-tryptophan |
| 14. | Asp-arg-val-tyr (SEQ ID NO: 9) |
| 15. | A-VI-5 |
| 16. | Glu-thr-pro $NH_2$ (SEQ ID NO: 10) |
| 17. | (D-ala2)-Beta-casomorphin (1-5) (bovine) |
| 18. | Tyr-D-ala-gly-phe-D-met acetate salt (SEQ ID NO: 11) |
| 19. | Arg-gly-asp-thr (SEQ ID NO: 12) |
| 20. | N-Alpha,n-omega-di-cbz-l-arginine |
| 21. | Asp-lys acetate salt |
| 22. | (+)-Allo-octopine |
| 23. | Sodium 7-[2-amino-2-phenylacetyl)amino]-3-methyl-8-oxo-5-thia-1-azabic cyclo[4.2.0]oct-2-ene-2-carboxylate |
| 24. | Val-ile-his-asn (SEQ ID NO: 17) |
| 25. | 2-Amino-8-(diphenylphosphinyl)-octanoic acid |
| 26. | Glu-His-Pro $NH_2$ (SEQ ID NO: 13) |
| 27. | Bapaba |
| 28. | H-glu(lys)-OH |
| 29. | Bis-boc-l-arg |
| 30. | H-arg(mtr)-OH |
| 31. | 4-Aminomethyl-L-phenylalanine boc |
| 32. | H-met-met-OH |
| 33. | H-trp-ile-OH |
| 34. | N-alpha benzoyl-arginine-4-amino benzoic acid |
| 35. | (Thr46)-osteocalcin (45-49) (human) |

As a result of the computational docking, 30 compounds from both the Site 1 and Site 2 lists were experimentally screened by NMR. Eleven compounds were found to bind to HLA-DR10, giving a successful hit rate of 37%. These ligands are listed in Table 4.

TABLE 4

NMR screened ligands that were found to bind to HLA-DR10. Ligands are separated by computationally predicted docking sites

| Site 1: | Site 2: |
|---|---|
| 5(6) carboxytetramethylrhodamine-n-succinimidylester | N-alpha benzoyl-arginine-4-amino benzoic acid |
| Methidiumpropyl EDTA | 5-leu-enkephalin (YAGFM) (SEQ ID NO: 18) |
| Deoxycholic acid | N alpha N omega dicarbobenzoxyarginine |
| FMOC-aspartic acid(O-benzyl)-OH | Angiotensin II (DRVY) (SEQ ID NO: 9) |
| 4-dimethylaminoazobenzene-4'-sulfonyl-L-valine4-[[5-(trifluoromethyl)-pyridin-2-yl]oxy]phenyl N-phenylcarbamate | Bis-BOC-L-arginine |

From Table 4, 5 synthetic high affinity ligands (SHALs) have been synthesized, containing different sets of the Site 1 and Site 2 ligands. Three of these molecules (FIG. 13A), all containing the ligand pairs deoxycholate and 5-leu-enkephalin, have been shown to bind to isolated HLA-DR10. None of these three SHALs bind to albumin or streptavidin. The first of the three to be tested more extensively, JP459B (FIG. 13B), has been determined to bind to HLA-DR10 with a Kd=23 nM using Surface Plasmon Resonance. Using Raji membrane extracts, this SHAL competed with Lym-1 for binding to HLA-DR10. Binding studies performed with live cells showed JP459B bound to Raji human lymphoma cells, but not normal DU145, LnCAP or 22RV cells (FIG. 17E-H). Experiments using frozen human lymphoma tissue sections also demonstrated JP459B binding to large cell lymphoma, exuberantly, but less to small cell lymphoma cells (FIG. 17A-D). Similar results were obtained with Lym-1 antibody. More extensive testing with normal and tumor tissue arrays is in progress.

In subsequent screenings additional ligands have been shown to bind to HLA-DR10. These are shown in Table 5.

TABLE 5

Additional ligands that bind to HLA-DR10.

| ligand ID | species |
|---|---|
| 11 | 3,3',5-Triiodo-dl-thyronine (Predicted Site 2) (TI) |
| 7 | 2-(4-Chlorophenyl)-2-[6-[(4-chlorophenyl)suflfanyl]-3-pyridazinyl] acetamide (12F) |
| 9 | 4-Amino-2-anilino-5-benzoyl-3-thiophenecarbonitrile (5K) |
| 8 | 6-Chloro-n4-(4-phenoxyphenyl)-2,4-pyrimidinediamine (7L) |
| 6 | N-(4-[[3-Chloro-5(trifluoromethyl)-2-pyridinyl]methyl]phenyl)-4-iodobenzenecarboxamide (6J) |

In addition 1,4-phenylenebis[[4-(4-aminophenoxy)phenyl]methanone] precipitated onto the target protein.

Example 2

Computational Methods for Use in the Creation of SHALS

A) Overview of the Roles and Methods of Molecular Simulations

As described herein, molecular modeling can be used to initially identify ligands for use in the construction of SHALs and/or for the optimization of SHALs. At present there is no single molecular modeling methodology that can be used to model target molecules, screen for binding ligands, simulate binding of a polydentate SHAL and predict optimal SHAL structure. A number of well established modeling methods, however can be used to facilitate these tasks as described herein.

Starting at the highest level, the prediction of the tertiary structures target molecules (e.g. protein cancer markers) are typically predicted using highly empirical methods based on primary sequence homology to proteins with experimentally known structure. The accuracy of these so-called homology-based protein structure prediction methods depend on the availability of homologous protein structures and the expertise of the individual modeler. To identify small molecules (ligands) that specifically bind into protein pockets, computational "docking" can be employed as described herein. Docking uses a relatively simple empirical force field to describe the ligand-protein interaction and can therefore be used to rapidly screen 100,000's of possible ligands. To determine preferred macromolecular conformations and interactions, classical molecular dynamics can used, which models the molecules using empirical ball-and-spring force fields. Finally, for the precise prediction of small molecule structures and interactions, one can computationally solve the quantum mechanical equations describing the electrons and nuclei within the molecules. This so-called first principles approach can either be used to determine the structures and energies of static "snapshots" of the molecules or to simulate the atomic motions of the molecular systems. The former approach, is referred to as ab initio quantum chemistry while the latter approach is called first principles molecular dynamics (in contrast to classical molecular dynamics) and constitutes a nearly exact simulation of nature.

B) Homology-Based Protein Structure Predictions.

The basic concept of homology-based protein structure prediction relies on the observation that structural features of proteins are conserved during evolution to a much higher degree than their sequences, and therefore proteins related even by distant sequence similarity can be expected to have similar 3D structures (Chothia and Lesk (1986) *EMBO J.,* 5: 823-826). Thus, once a three-dimensional structure is determined for at least one representative of a protein family, models for other family members can be derived using the known structure as a template. Homology-based protein modeling consists of four major steps: finding known structures related to the protein sequence to be modeled, aligning the sequence with these structures, building a three-dimensional model, and assessing the model (Marti-Renom et al. (2000) *Annu Rev Biophys Biomol Struct.,* 29: 291-325).

Figure 15:
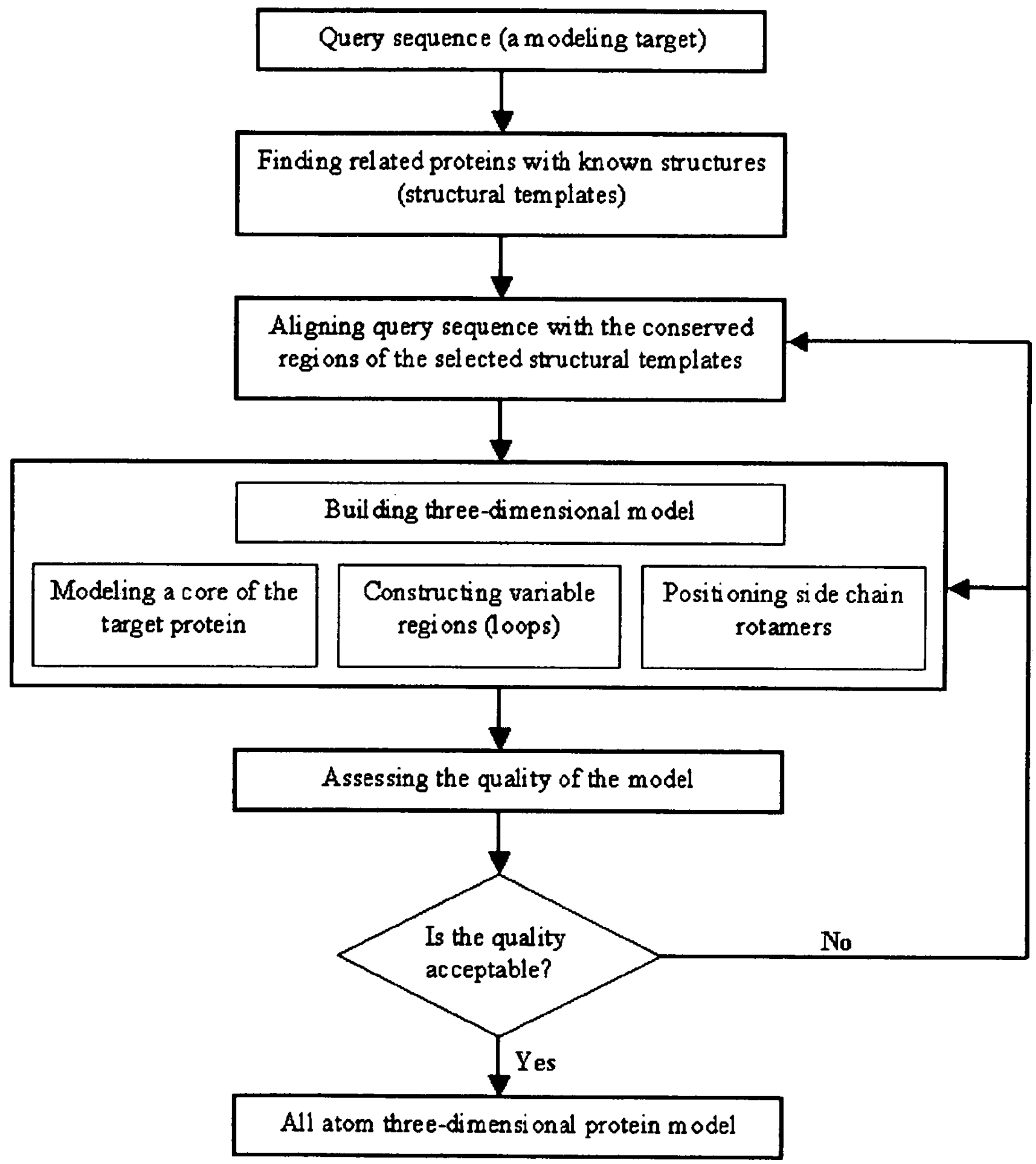
FIG. 15 illustrates a flowchart describing major steps in homology-based protein modeling.

Homology-based protein structure prediction (also referred to as comparative modeling) produces an all-atom model of a sequence based on its alignment with one or more related protein structures. Building of the three-dimensional model itself includes either sequential or simultaneous modeling of the core of the protein, loops and side chains. FIG. 15 illustrates a flowchart describing major steps in homology-based protein modeling.

The accuracy of a model, built using comparative modeling technique, usually is related to the percentage of sequence identity with the structure on which it is based. High-accuracy comparative models are based on more than 50% sequence identity to their templates. They tend to have about 1 Å root-mean-square (RMS) error for the main chain atoms. Such accuracy is comparable with medium resolution nuclear magnetic resonance (NMR) structure or low resolution X-ray structure. The errors in such cases are usually limited to mistakes in side chain rotamer assignment, small shifts or distortions in the core main chain regions, and occasionally larger errors in loops.

One general modeling approach will be similar to that successfully used earlier to model both high and low homology target proteins (Venclovas et al. (1999) *Proteins-Structure Function and Genetics,* 73-80). Since our modeling objects (e.g. cancer markers such as HLA-DR10) can have high sequence homology (>50% sequence identity) we can rely on pairwise sequence comparison of modeling target (query) with the proteins of known structures (from the Protein Data Bank (PDB)) to identify the closest structural templates. To do this, a sensitive Smith-Waterman pairwise sequence comparison algorithm (Smith and Waterman (1981) *J. Mol. Biol,* 147: 195-197) implemented in the SSEARCH program (Pearson (1991) *Genomics* 11: 635-650) can be used. At the high level of sequence homology structure alignment for the conserved structural regions can be used directly in model-building.

When a number of structural templates of comparable similarity are available one can use MODELLER, a comparative modeling program capable of automatically combining a number of template structures to better represent the structure of the query. Where critical regions are present in the target molecule, special care can be taken in assigning conformations to these regions. The candidate conformations for these regions can be produced by searching a database of homologous structures for the fragments of identical length that also satisfy the steric constraints for these regions. Both sequence similarity and structural context near the region can be taken into account in selecting the actual conformation. Side chains within the model can be positioned using a backbone-dependent rotamer library (Bower et al. (1997) *J. Mol. Biol.* 267: 1268-1282).

Assessment of the obtained models can be done using several techniques. One of these, Prosall (Sippl (1993) *Proteins,* 17: 355-362,; Aloy et al. (2000) *J Comput Aided Mol Des.* 14: 83-92), which is used to detect errors in protein structures, creates an energy profile along the sequence of the protein. The regions that are assigned high energy values by Prosall often serve as good indicators of errors in representing the structure of these particular regions. For the detailed checks of modeled structures, the structure verification module of the WHATIF program (Vriend (1990) *J. Mol. Graph* 8: 52-56) can be used along with visual inspection. If these assessments of model quality identify any problems in the modeled structure, appropriate steps (such as loop assignment or side chain positioning) will be repeated in an iterative manner until an acceptable quality three-dimensional model is obtained.

Using these methods a computer model of the molecular structure of the HLA-DR 10 beta subunit containing the region shown to be critical for Lym-1 antibody binding to malignant B cells was developed and the structure was compared with the structure with other HLA-DR molecules (see Example 1, supra.). This model was used to develop HLA-DR10 specific SHALs as described herein.

C) Computational Docking

Computational methods such as docking have been used to speed up the process of drug discovery and inhibitor design by screening large numbers of molecules and predicting whether or not they bind into the active sites of target proteins (Desjarlais et al. (1990) *Proc. Natl. Acad. Sci. U.S.A.,* 87: 6644-6648; Mao et al. (1998) *Bioorganic and Medicinal Chem. Letts.,* 8: 2213-2218; Olson and Goodsell (1998) *Environmental Res.,* 8: 273-285; Rutenber et al. (1993) *J. Biol. Chem.,* 268: 15343-15346). These efforts have met with moderate success in the design of new drugs effective against HIV proteins critical for infection and transmission of the disease In certain embodiments, this approach is generally useful as a first step in the identification of ligands (binding moieties) that usually bind to the target molecule(s) in the micromolar range. Detailed protocols for docking methods using SPHGEN and DOCK have been described in the literature. For example, these methods have been used to identify ligands that bind to specific sites on the targeting domain of tetanus neurotoxin (Cosman et al. (2002) *Chem Res Toxicol* 15: 1218-1228; Lightstone et al. (2000) *Chem. Res. Toxicol.,* 13: 356-362).

The program DOCK 4.0 was used to computationally screen the Available Chemical Directory (~300,000) of small molecules to identify the top ranked 2,500 molecules predicted to bind to the identified Site 1 and Site 2 (FIG. 12).

Computational docking can be thought of as a three-step process: 1) site identification of the protein surface; 2) docking of ligands into the identified binding site; and 3) scoring and the ranking of the ligands (Halperin et al.(2002) *Proteins: Structure, Function, and Genetics,* 47: 409-443). For site identification, the solvent accessible surface of the target protein is generally calculated. Using the program SPHGEN, a utility in DOCK (Moustakas and Kuntz (2002). DOCK 4.0 (San Francisco, UCSF)), concave pockets on the protein surface were identified by filling the pockets with different sized radii spheres. Essentially, this calculates the volume of the pocket. The surface of the protein may have anywhere from thirty to hundreds of pockets based on the size and shape of the protein. Once these pockets were identified, visual inspection of the pockets identified the binding site based on the size of the pocket and the available experimental evidence, such as known amino acids involved in binding or catalysis. The chosen binding pocket was then used in the subsequent docking procedure.

Figure 16:
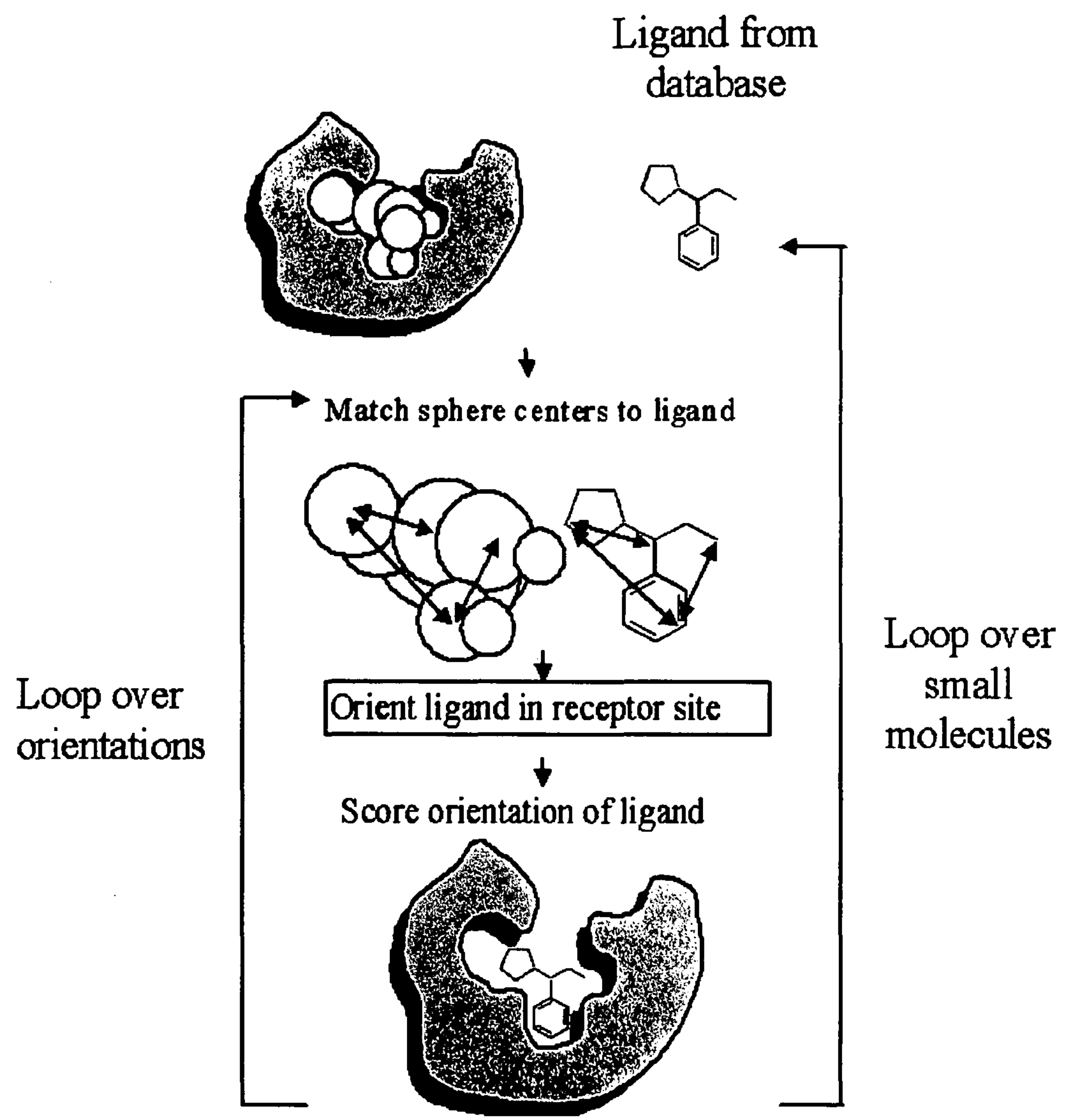
FIG. 16 illustrates a DOCK algorithm. (1) A "negative image" is generated by filling a pocket with spheres. (2) A candidate ligand is retrieved from a database. (3) Internal distances are matched between a subset of sphere centers and ligand atoms (usually three to eight centers are chosen). (4) The ligand is oriented into the active site. (5) The interaction for that orientation is evaluated by a scoring function; the process is repeated for new orientations—typically 10,000 orientations are generated per ligand. The top-scoring orientation is retained. The process is repeated for a new ligand in the database
Figure 17A:
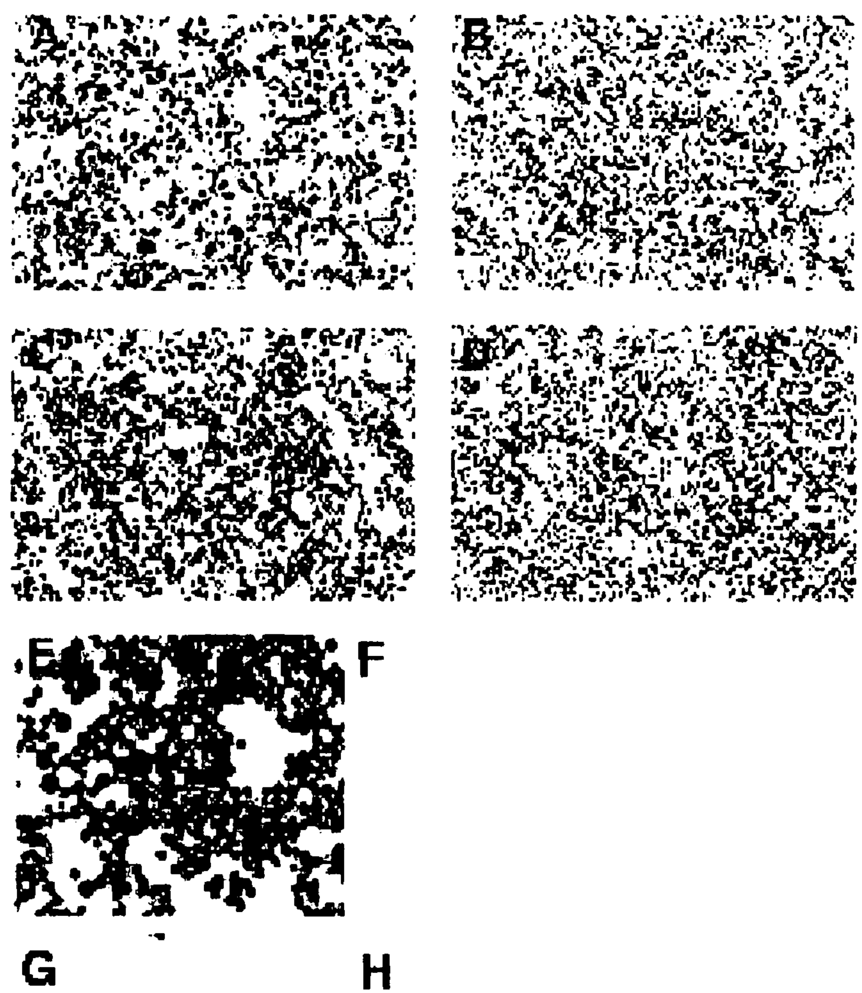
FIGS. 17A and 17B illustrate binding of SHAL JP459B to cells displaying MUC-1.
Figure 17B:
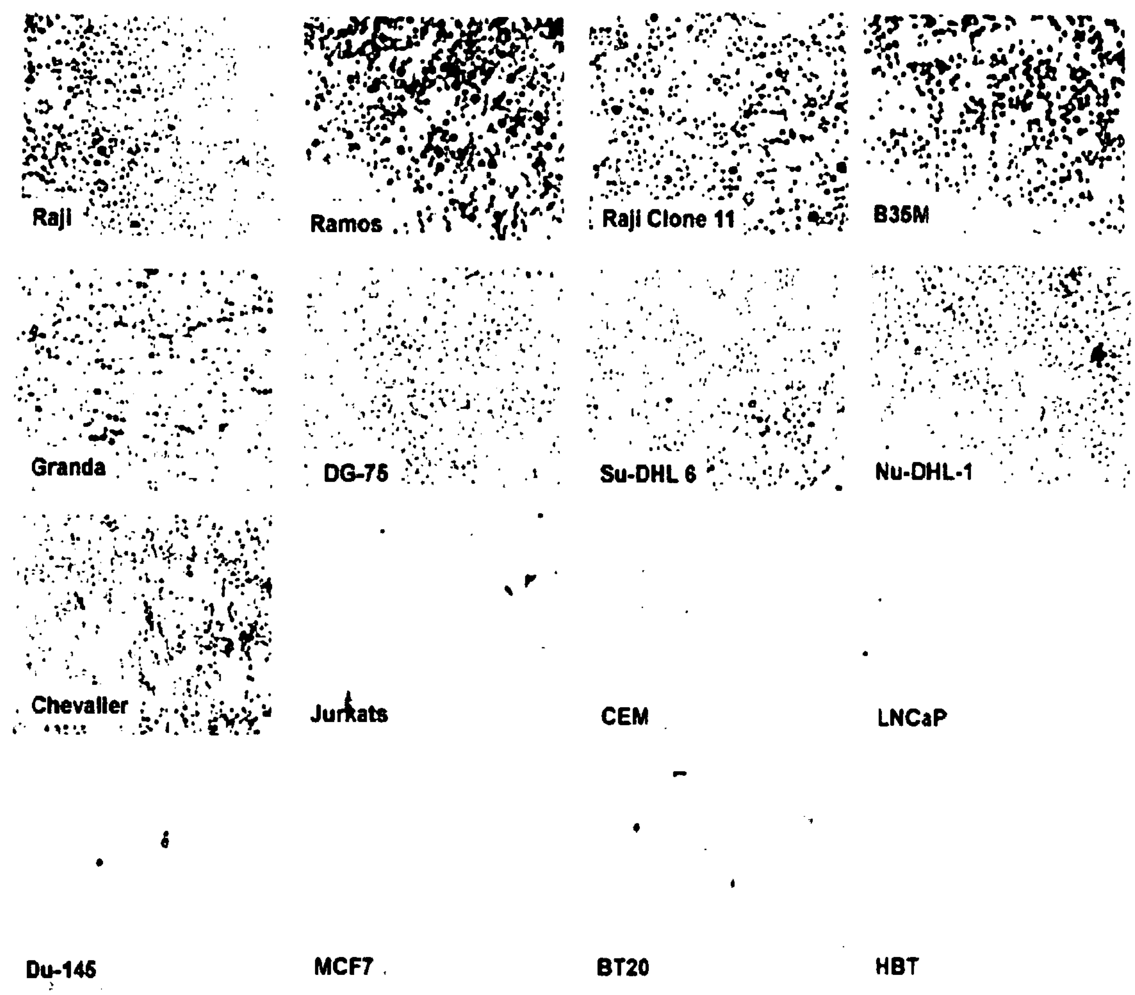
Figure 18:
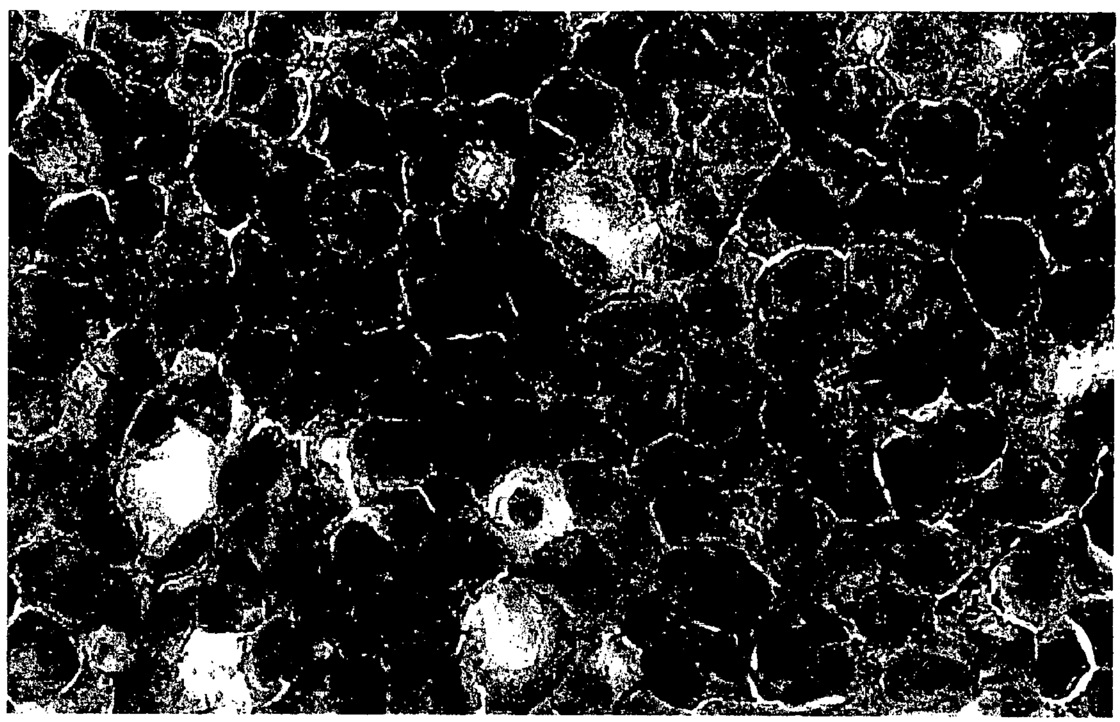
FIG. 18 shows a tissue section from NH lymphoma illustrating that JP459B staining of lymphoma cells is localized to the cell membrane.

Docking studies identify small molecules that might bind specifically to the chosen binding site on the protein. The DOCK 4.0 program screens a database of compounds on the computer and predicts which molecules will likely bind tightly to the binding site. This procedure is illustrated in FIG. 16. Applicants used the Available Chemicals Directory (ACD) from MDL as their database of compounds to screen.

The database was prepared by prefiltering to remove soaps and dyes. After the partial charges for the compounds were calculated by using Gasteiger-Marsili charges (Gasteiger and Marsili (1978) *Tetrahedron Letts.,* 34: 3181-3184; Gasteiger and Marsili (1980) *Tetrahedron* 36: 3219-3288; Gasteiger and Marsili (1981) *Organic Magnetic Resonance* 15:353-360) in Sybyl, the database was divided by total compound charge, and compounds with formal charge >±3 are filtered out. Also, compounds <10 and >80 heavy atoms (not hydrogens) were removed to focus on compounds within the size range for lead (preliminary) drug compounds. This prefiltering made the database more efficient and eliminated unnecessary calculations on compounds known to either never bind or bind indiscriminately. To simulate a flexible docking technique, 20 unique conformations were generated for each compound in the database. Each of these conformations was then rigidly docked into the binding site. Different orientations within the binding site were examined for each of the conformations of each of the ligands. All compounds were scored by energy minimization where the intermolecular van der Waals and electrostatic terms are derived from AMBER (Weiner (1984) *J. Am. Chem. Soc.,* 106: 765-784). Though the molecules are ranked based on the scores, the scoring function does not predict the binding affinities.

The top ranked 2,500 molecules were then visually inspected to select down to thirty-five molecules for experiment binding assays as described in Example 1. Ligands were selected and bidentate SHALs were constructed and tested as described in Example 1.

The binding of lead compounds to the target can be improved by several orders of magnitude by using multiple (2-3) compounds linked together. For the inhibitor to be effective, it needs to recognize specifically the target protein and bind with high affinity.

D) Quantum Chemical Calculations

A wide variety of chemical simulation methods have been developed, ranging from empirical ball-and-spring type molecular mechanics models to ab initio (first principles) quantum chemical methods that calculate approximate solutions to the exact quantum mechanical equations describing the electrons and nuclei. Typically, the choice of methods involves trade-offs between accuracy, size of the chemical system, and computational cost. These modeling methods can be broadly divided into molecular dynamics methods that simulate the time evolution of chemical processes and static methods that predict time-independent molecular properties such as the lowest energy configuration of a molecule or the energy of a chemical reaction. One can use all three molecular modeling methods described below: ab initio quantum chemistry, classical molecular dynamics and first principles molecular dynamics in the design and optimization of SHALs as described herein.

1. Ab initio Quantum Chemistry (QM)

Ab initio quantum chemistry involves computing approximate solutions to the exact non-relativistic Schroedinger equation describing a molecular system (Jensen (1999) Introduction to Computational Chemistry, New York, John Wiley and Sons). In principle these methods can predict the properties of any chemical system to arbitrary accuracy, but in practice the computational cost limits the accuracy of these methods and the size of the molecular systems to which they can be applied. Nevertheless, ab initio quantum chemical calculations are routinely applied to calculate accurate structures and reaction energies for molecular systems including up to hundreds of atoms.

There is a hierarchy of different ab initio quantum chemical methods involving increasingly accurate mathematical descriptions of the electronic wave function—the mathematical description of the distribution of electrons around the nuclei of a molecule (Id.). Application of quantum chemistry typically requires the choice of both the description of the electron-electron interactions (level of theory) and the spatial flexibility of the electrons (basis set). A fairly new class of methods called Density Functional Theory (DFT) has been developed that includes empirical parameterizations of the electron-electron interactions, and often provides accuracy comparable to the earlier high-level quantum chemical methods (such as Coupled Cluster methods), but with a much lower computational cost. The DFT methods are usually denoted by the empirical electron-electron “functional” employed. Two widely used DFT functionals are the Becke 3-parameter hybrid exchange functional (Becke (1993) *J.*

*Chem. Phys.* 98: 5648-5652) and the Lee-Yang-Parr gradient corrected electron correlation functional (Lee et al. (1988) *Chemical Physics* 123: 1-25). These have been widely demonstrated to yield accurate chemical structures and reaction energies for most molecules when used with sufficient basis sets (Jensen (1999) *Introduction to Computational Chemistry*, New York, John Wiley and Sons).

The quantum chemical simulations described herein are used to study chemical processes that occur in the immediate extracellular environment. The quantum chemical methods described above typically describe only an isolated (usually described as "gas-phase") molecule and therefore do not include the chemical environment, such as solvent molecules and counterions, which frequently is critical to the structure and energetics of biological molecules. Explicitly including the surrounding water molecules and counter ions is usually not computationally practical; however, several methods have been developed within the quantum chemistry approach for effectively including the effects of solvent interactions. Typically these methods model the solvent as a continuous medium that polarizes in response to the quantum chemically derived charges. Although there are many situations where explicit inclusion of the solvent is necessary, these so-called polarizable continuum models have proven reasonably accurate in predicting solvent-phase chemical properties including total solvation energies and acid constants (Schüürmann et al. (1998) *J. Physical Chemistry* A 102: 6706-6712; Tran and Colvin (2000) *J. Molecular Structure, Theochem* 532: 127-137).

The Langevin dipole method of Warshel is related to these polarizable continuum models, but includes a more realistic representation of the polar solvent. The Langevin dipole method models the solvent as a large set of polarizable dipoles on a fixed three-dimensional grid (Luzhkov and Warshel (1992) *J. Computational Chemistry* 13: 199-213). This approach has recently been parameterized for use with ab initio derived solute charges and shown to yield solvation energies for neutral and ionic molecules comparable or better than PCM methods described above (Florian and Warshel (1997a) *J Am Chem Soc.,* 119: 5473-5474).

2. First Principles Molecular Dynamics (FPMD)

By combining the forces determined directly from a QM method to drive the classical motion of all the atoms in a simulation, one can achieve the accuracy of quantum mechanics (QM) with the advantages of classical molecular dynamics. This approach became computationally feasible with the development of a new technique based on density functional theory (DFT) (Kohn Sham (1965) *Physical Review* 140: Al 133) that treats electronic degrees of freedom at the same time as the nuclear equations of motion (Car and Parrinello (1985) *Physical Review Letters* 55: 2471-2474; Galli and Parrinello (1991) Pp. 283-304 In: *Computer Simulation in Materials Science*, The Netherlands, Kluwer Academic Publishers). Since the method employs QM theory to describe the entire system, it is often referred to as first principles molecular dynamics (FPMD). In the typical implementation of FPMD, only the chemically active valence electrons are explicitly described with an expansion in a plane-wave basis, while the chemically inert core electrons are represented by pseudopotentials (Galli and Pasquarello (1993) Pp. 261-313 In: *Computer Simulation in Chemical Physics*, D. J. Tildesley, ed. Dordrecht, Kluwer; Yin and Cohen (1982) *Physical Review B* (*Condensed Matter*) 25: 7403-7412). Because the pseudopotentials are transferable by design, this method does not require reparameterization when new systems are studied. In addition, the use of a plane wave basis set naturally lends itself to the application of periodic boundary conditions, so the method is well suited for modeling systems in the condensed phase. This method, combined with several other computational improvements (Gygi (1993) *Physical Review B* 48: 11692-11700; Hutter et al. (1994) *Computational Materials Science* 2: 244-248; Payne et al. (1992) *Rev. Modern Physics* 64: 1045-1097), has been instrumental in solving the problem of integrating QM and MD.

The first applications of FPMD simulations were limited to small systems such as silicon (Car and Parrinello (1985) *Physical Review Letters* 55: 2471-2474; Stich et al. (1989) *Physical Review Letters* 63: 2240-2243). As these methods have been continuously improved upon, and advanced computational resources have become available (such as the DOE teraflop scale supercomputers) it is now possible to investigate small biochemical systems containing several hundreds of atoms for picosecond timescales (Carloni and Alber (1998) *Perspectives in Drug Discovery and Design* 9/11: 169-179; Pantano et al. (2000) *J. Molecular Structure* (*Theochem*) 530: 177-181; Rovia and Parrinello (2000) *International Journal of Quantum Chemistry* 80: 1172-1180). For example, we have recently simulated the conformational dynamics of a small chemical model of the DNA backbone in solution. As the number of systems that have been investigated with this new approach increases, it is becoming clear that the increased computational expense is repaid in the form of extremely accurate structural and dynamical properties. In particular, such methods potentially allow for very accurate dynamical simulations of chemical phenomena including chelator-metal ion interactions and enzyme-catalyzed reactions.

E) Classical Molecular Dynamics (MD)

Classical molecular dynamics can be used to in identifying the exact orientation of the ligands in the in the binding sites of the target molecule(s) (e.g. HLA-DR 10 binding sites (Site 1 and Site 2)). This information can be used in designing the multivalent ligands to carry radioisotopes selectively to the target molecule and/or to cells displaying the target molecule.

In particular, this structural data helps identify which functional groups on the ligand(s) can be used to synthetically attach the linker. For all ligands that are experimentally verified to bind to the target, classical molecular dynamics can be performed on the ligand in the target binding sites to determine conformation and orientation of the ligand and the specific interactions mediating the binding specificity (e.g. hydrogen bonds, electrostatic and Van der Waals interactions). In certain embodiments, the molecular dynamics simulations will include the target and the ligands solvated in a periodic water box. For each ligand, 500 ps to several nanosecond simulations can be performed using multiple starting orientations.

An important component of the polydentate SHALs of this invention is the molecular linker between the individual ligands (binding moieties) comprising the SHAL. Typically this linker adopts an aqueous-phase conformation (or set of conformations) that holds the two (or more) ligands at appropriate distances to efficiently bind into their binding site on the target surface. To assist in designing this linker classical molecular dynamics can be performed on the linker molecular alone and the linker bound to specific ligand compounds.

The program CHARMM can be used to perform classical molecular dynamics simulations on various linkers. For example, simulations performed with PEG linkers can utilize a different number of PEG units (4, 6, and 8) in the molecules. The starting structures for all four simulations can have the molecules in a fully extended conformation. These extended molecules can be solvated in water boxes and sodium ions are added to each water box to neutralize the systems. These solvated systems are heated to e.g., 300 K and allowed to equilibrate for 200 picoseconds. Typically simulations can be run at constant temperature (NVT ensemble) and electrostatic interactions treated by particle mesh Ewald (PME) summation.

Initially the two compounds to be linked can be visually examined together bound to the protein as determined by docking and molecular dynamics using computer graphics. For example, a polyethylene glycol (PEG) linker will be built using molecular drawing software (AMPAC) between the two compounds. This structure can then be simulated using classical molecular dynamics in a periodic water box, e.g. as described above for several nanoseconds. One can analyze the resulting data on the dynamical motions to measure the average ligand-ligand distance and relative ligand orientation. This data can be compared with the distance between the ligands and relative orientation on the target surface to determine the optimal length for the linker.

Molecular dynamics simulations can also be used to investigate a number of other properties on the overall SHALs to optimize their therapeutic effectiveness. In particular molecular dynamics simulations can be used to investigate a number of modifications including the chemical structure of the linker itself, and the two ligands at each end. The goal of these simulations will be to identify likely effects of such modifications on target binding efficiency and specificity prior to expensive synthetic modifications.

Molecular dynamics methods use an empirically derived classical force field to simulate the motion of each atom in a chemical system. This methodology is highly developed for the simulation of nucleic acids, (Beveridge and McConnell (2000) Curr. *Opinion in Structural Biology* 10: 182-196) and proteins (Brooks et al. (1983) *J. Computational Chemistry* 4: 187-217; Cheatham and Brooks (1998) *Theoretical Chemistry Accounts* 99: 279-288; Doniach and Eastman (1999) *Curr. Opinion in Structural Biology* 9: 157-163). Typical published molecular dynamics simulations involve 10-100,000 atoms (including both the biomolecules being simulated and a surrounding shell of water and counter ions) which are simulated for multi-nanoseconds of time, with the largest published simulation being a 1 microsecond simulation of a small protein (Duan and Kollman (1998) *Science* 282: 740-744). The multinanosecond time scale is thought sufficient to capture structural relaxation and solvent reorganization, and is long enough in some cases to simulate transitions between different macromolecular conformations (Cheatham and Kollman (1996) *J. Mol. Biol.,* 259: 434-444; Yang and Pettitt (1996) *J. Physical Chemistry A* 100: 2564-2566).

A molecular dynamics simulation of polyethylene glycol (PEG) has recently been published that is relevant to the design of PEG linkers for SHALs. Heymann and Grubmuller used classical molecular dynamics to describe the conformational and elastic properties of individual PEG chains (Heymann and Grubmuller (1999) *Chemical Physics Letters* 307: 425-432; Young and Lovell (1992) Introduction to Polymeres, New York, Chapman and Hall). They simulated a PEG 18-mer (~1 kDalton molecular weight) in the aqueous phase (solvated by 1539 water molecules) and in the gas-phase (to approximate solvation in a non-polar solvent such as hexadecane). They found that in the gas-phase the PEG rapidly collapsed to a compact structure with no local structure, as measured by the degree to which the PEG had a helical local structure. In water, the PEG behaves very differently. It does show a reduction in the radius of gyration compared to the fully extended structure, but retains a marked degree of helicity and therefore some degree of stiffness. These simulations indicate that the local stiffening of the PEG structure is caused by water molecules that form hydrogen bond bridges between successive oxygens in the PEG chain. They further simulated the stretching of the PEG chain with a range of forces from 0 to 500 picoNewtons (this mimics experimental studies with Atomic Force Microscopes). They find good agreement in their predicted force versus extension curves with values recently measured in a single PEG molecule (Oesterhelt et al. (1999) *New Journal of Physics* 1: 6.1-6.11).

These results demonstrate that classical molecular dynamics simulations of PEG can accurately reproduce complex properties such as the force/extension curves and strongly supports the accuracy of the proposed PEGylated scaffold simulations. Although the PEGylated scaffold currently in use (13.6 kDalton molecular weight) is considerably larger than the PEG 18-mer simulated by Heymann and Grubmiller, it is well within reach of routine molecular dynamics simulations.

Molecular dynamics simulations can readily be performed with the CHARMM software package (Brooks et al. (1983) *J. Computational Chemistry* 4: 187-217) using the version 22 parameter set (MacKerell et al. (1998) *J. Physical Chemistry B* 102: 3586-3616). Analysis can be performed using the analysis tools distributed with CHARMM and VMD, a graphical molecular dynamics analysis tool (Humphrey et al. (1996) *J. Molecular Graphics* 14: 33-38).

The steps in a typical setup and simulation runs are as follows:

A. Preliminary Setup.

1. Calculation of partial charges for atom types not included in CHARMM force field. Model compounds containing the unparameterized atom types will be optimized at the Hartree-Fock level of theory using a 6-31G(d) basis set. Upon convergence, partial charges of each atom will be computed using Merz-Kollman charge fitting scheme (Besler et al. (1990) *J. Computational Chemistry* 11: 431-439). These charges can replace the default atomic charges.

2. Molecules to be Simulated:

a. Construction of molecular structures

The molecules to be simulated can be built using QUANTA and the atomic charges will be obtained as in step one above. The net charge of the whole compound can then be computed.

b. Solvation of the Molecular Structures:

The molecules and molecular complexes constructed in step 2a can be neutralized using $Na^+$ ions that are positioned using the SOLVATE program. The whole system can then be solvated in a box of water molecules and this simulation box can be subsequently adjusted to yield the appropriate density.

B. Running the Simulation:

1. Equilibration of the Molecule/Water/Counterion System:

a. Minimization: To remove residual strain remaining in the molecular structures from the construction phase, the solvated molecules from step 2b above can be minimized for 10,000 steps, of which the first 1,000 iterations are performed using steepest descent and the rest using adopted basis Newton-Raphson methods.

b. Equilibration: After minimization, The temperature can be ramped up from 0K to 300K over 10 ps and held fixed at 300K thereafter. The system can be equilibrated for 200 ps at constant temperature. The long range forces are handled by particle mesh Ewald method Essmann et al. (1995) *J. Chemical Physics* 103: 8577-8593. The water molecules are TIP3P (Jorgensen et al. (1983) *J. Chemical Physics* 79: 926-935). An integration time step of 2 femtoseconds can be used, and the SHAKE algorithm can be employed to restraint all the motions of the hydrogen atoms (Reichert and Welch (2001) *Coordination Chemistry Reviews* 212: 111-131).

c. Production runs: For the production simulations, constant temperature molecular dynamics (using the NVT ensemble) can be used. The particle mesh Ewald method (Essmann et al. (1995) *J. Chemical Physics* 103: 8577-8593) can be used for the long range forces. During the dynamics runs, the complete set of atomic coordinates can be saved every 0.1 ps for subsequent analysis. For the preliminary simulations, the molecular dynamics simulations ran on our Compac Alpha computers at a speed corresponding to approximately 625 cpu hours (~4 weeks) per nanosecond, therefore, multi-nanosecond simulations of these systems will be routinely feasible on our large network of workstations.

Example 3

Synthesis and Testing of a Bi-Dentate Shal

Figure 14:
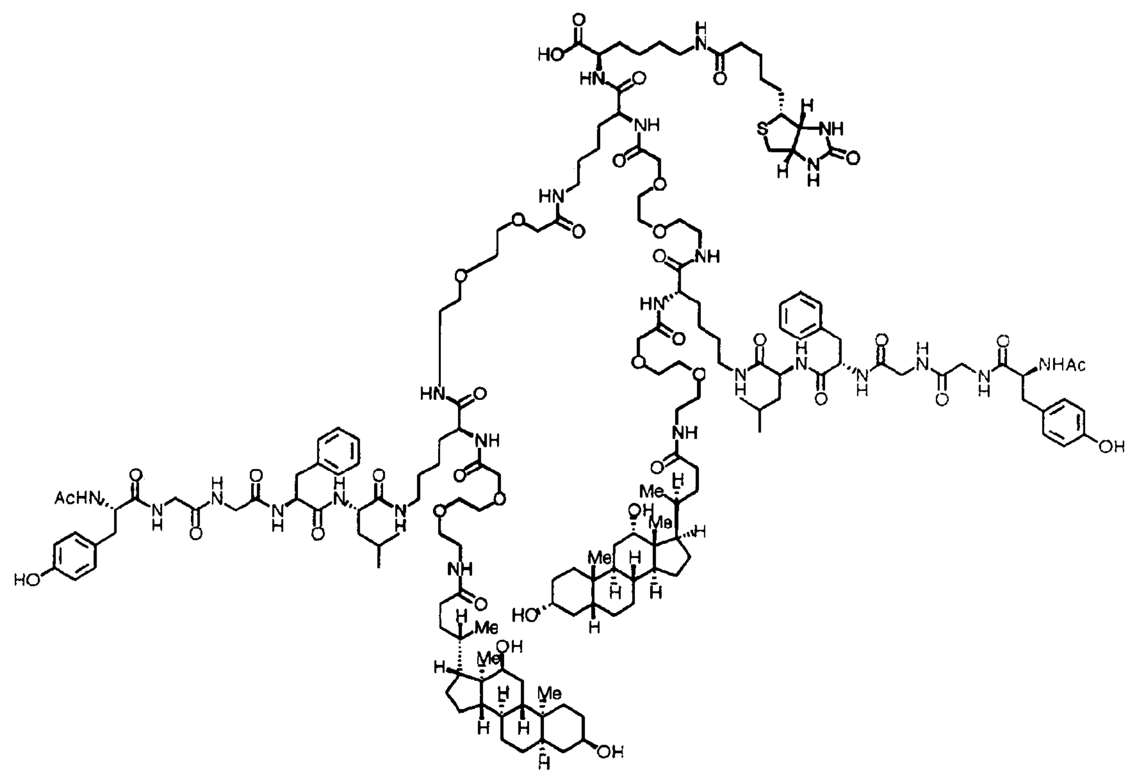
FIG. 14 illustrates the structure of a bivalent version of JP459B. Red is deoxycholate; Green is 5-leu-enkephalin; Blue is the lysine linker; and Black is the PEG linker and biotin.

The bivalent SHAL $(LeacPLD)_2LPDo$ was synthesized, purified by HPLC and characterized by mass spectrometry. This SHAL has two JP459B bidentate ligands interconnected via a linker and a DOTA attached on the third arm (see, e.g., FIG. 14).

SHALs were designed around an orthogonally protected lysine residue to facilitate synthesis on solid phase resin. A commercially available Fmoc-protected amino acid-like mini-peg (2 $CH_2O$'s) was used as a linker to incrementally increase the distance between the enkephalin and the deoxycholate moieties. Fmoc-biotinyl-lysine was used to introduce biotin into the SHALs for biacore experiments. All SHALs follow the same configuration: $CO_2H$:Biotin-lysine:lysine:(a lysine $NH_2$: 0, 1, 2 mini-peg linker, deoxycholate)(g lysine $NH_2$: LFGGY-NHAc (SEQ ID NO:19)). The bis-bidentate SHAL follows the convention: $CO_2H$:Biotin-lysine:lysine: [(a lysine $NH_2$: 0, 1, 2 mini-peg linker, deoxycholate)(g lysine $NH_2$: LFGGY-NHAc (SEQ ID NO:19))]2—and therefore is unsymmetrical about the second lysine residue.

All chemicals used were purchased from Aldrich or Nova Biochem. SHALs were synthesized using standard Fmoc solid phase synthesis on chlorotritylchloride resin. Ligands were cleaved from the resin and the protecting groups removed using the appropriate reagents. Trifluoroacetic acid esters formed on the primary alcohols of deoxycholate during cleavage from the resin were removed by stirring in ammonium bicarbonate. SHALs were purified using reverse phase high performance liquid chromatography (HPLC). Analytical HPLC was carried out at 1 mL/min on an Agilent 1100 machine (Waters Symmetry C18, 5 mm, 4.2×150 nun column) and preparative HPLC was carried out at 10 mL/min on a Waters preparative machine (Waters Symmetryprep C18, 7 mm, 19×300 mm column). SHALs were characterized using nuclear magnetic resonance (NMR) spectroscopy and electrospray mass spectrometry. 1H and 13C NMR spectra were recorded on a Bruker DRX 500 MHz spectrometer. Mass spectra were acquired on a Micromass Quattro Micro API mass spectrometer operating in positive ion mode.

Mass spectrometry of the SHAL $(LeacPLD)_2LPDo$ showed that it does not contain any free DOTA. Free DOTA would not be expected to be present based on the process used to synthesize the SHAL. $(LeacPLD)_2LPDo$ was synthesized by attaching each linker component or ligand onto a growing chain covalently attached to the surface of a resin. After each chemical reaction the resin was extensively washed to remove the unreacted products. DOTA was attached to the linker at the beginning of the synthesis. After the excess DOTA was washed away, multiple additional chemical reactions that were carried out on the resin to add the various linkers and ligands, and after each reaction the unreacted products were again washed away. By the time the synthesis of the SHAL was completed, the amount of free DOTA present in the sample was undetectable by examination of the HPLC and mass spectrum. The DOTA link is extremely stable, so it does not come off the SHAL once it's been attached.

During radiochemistry, components that may be present in the early runoff peak that can have associated radioisotopic label include the buffer salt (ammonium bicarbonate), possibly a trace amount of trifluoroacetate removed from the SHAL hydroxyls during the final synthesis step, and excess EDTA and free and EDTA-complexed isotope that didn't bind to the DOTA. Dialysis may simply not be the preferred method for efficiently eliminating all this material. Reverse dialysis is one preferred method for purification. Alternatively, chelate (EDTA) scrubbing after radiochemistry can be performed using an EDTA bead column to remove radiometal that has not been DOTA chelated or is loosely attached in a non-specific manner.

To get the metal into the DOTA efficiently, adjusting the reaction mix to an adequate alkaline pH is also important. Since the SHAL as a molecule is quite different from an antibody-DOTA molecule, the method used to raise the pH on the SHAL-DOTA complex preferably also raises the pH sufficiently on the SHAL. One can easily get other metals in DOTA if they are present at any stage. These can be detected by checking the mass spectrum of the compound. We have looked at the spectrum from purified SHALs and see little or no other metal there.

Biotinylated deoxycholate-iodothyronine SHALs are synthesized in an analogous manner.

Figure 20:
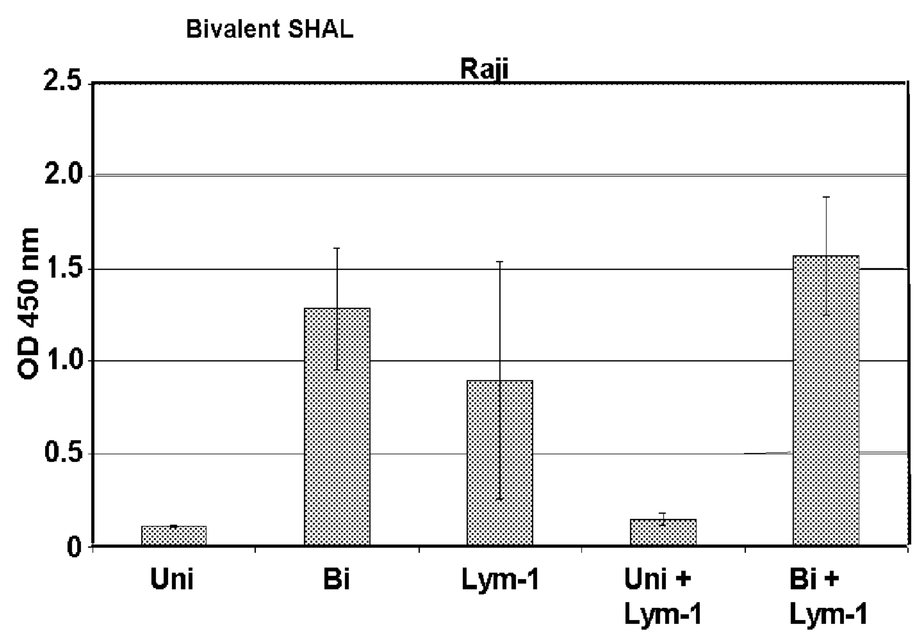
FIG. 20 illustrates the binding of univalent bidentate SHAL and bivalent bidentate SHAL 070804LeacPLDB to Raji cells in presence and absence of Lym-1 antibody.

ELISA assays showed that SHAL, LeacPLBD (the univalent bidentate SHAL), bind to and discriminate between cells containing HLA-DR10 and those that do not contain HLA-DR10 (see FIG. 20).

Figure 19:
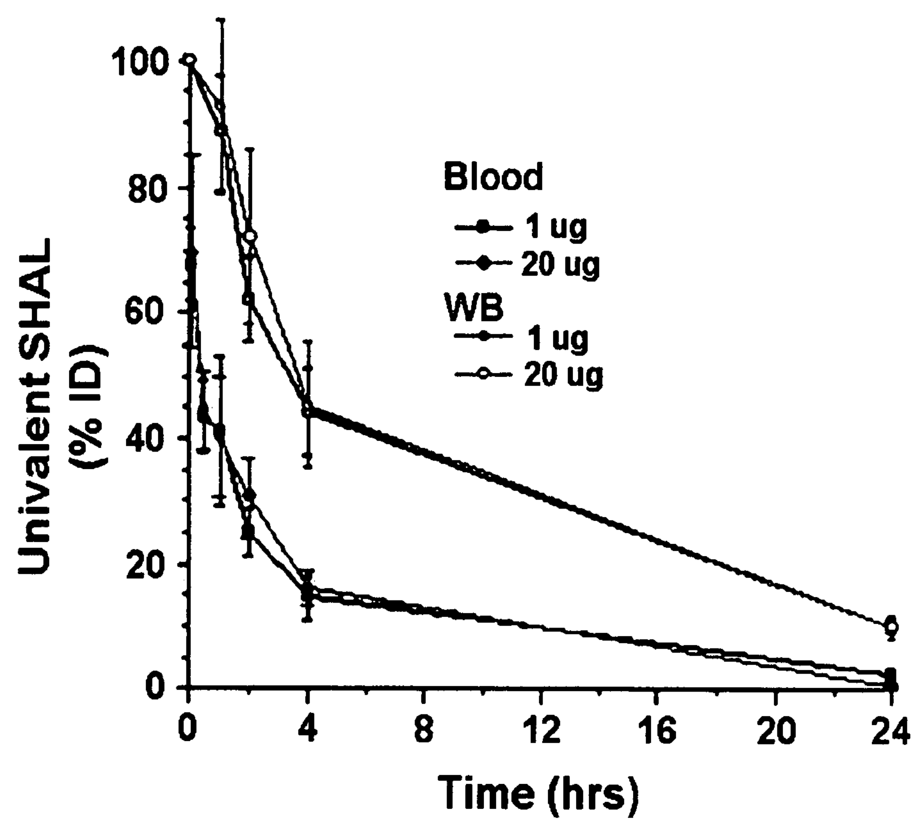
FIG. 19 illustrates $^{111}$In-DOTA [SHAL 070804(LeacPLD)$_2$ LPDo] biodistribution in Raji tumored mice.

Several pharmacokinetic, biodistribution and imaging studies were performed with consistent results. In certain embodiments, $^{111}$In-DOTA [SHAL 070804$(LeacPLD)_2$ LPDo] biodistribution was determined in Raji tumored mice (see, e.g., FIG. 19A).

Example 4

Development of Synthetic High Affinity Ligands that Bind to a Structural Epitope on the Tumor Cell Receptor HLA-DR10

A number of cell surface protein receptors have been identified that distinguish malignant cancer cells from their normal counterparts. While several of these receptors have been shown to be more abundant on cancer cells (e.g., CD20, CD22), others have been confirmed to differ structurally (e.g. HLA-DR10, Muc-1) from the same or closely related receptors present on normal cells. This has led to the development of a variety of antibody-based, receptor-specific reagents conjugated to radioisotopes for use in radio-immunotherapy. Lym-1, an antibody developed to bind to a unique structural epitope on the abundant cell surface receptor HLA-DR10 found only on human lymphoma and normal B-cell lymphocytes, has been used with some success in the treatment of non Hodgkin's lymphoma. In an effort to develop smaller and more effective therapeutics for treating non Hodgkin's lymphoma, we have synthesized the first in a series of small (<3 kD) selective high affinity ligands (SHALs) that bind to this same HLA-DR10 structural epitope. A homology model for HLA-DR10 was created using four known crystal structures of related HLA-DR molecules. Two unique "pockets" located on the surface of the protein adjacent to key amino acids required for Lym-1 binding were identified, and computational docking techniques were used to prescreen a large library of small molecules to predict which compounds should bind to each site. A small number of these compounds were tested experimentally using NMR spectroscopy to confirm their binding to the isolated HLA-DR10 protein, and pairs of compounds binding to the two different "pockets" were linked together using solid phase synthetic chemistry to create a series of bidentate reagents with different length linkers. The SHAL exhibiting the highest affinity for isolated HLA-DR10 (~23 nM) has been shown to bind selectively to nine different cultured cell lines containing HLA-DR10 and to frozen and fixed tissue sections obtained from patients with small cell and large cell human lymphomas. A bivalent form of this SHAL was also synthesized and shown to further enhance cell binding.

Example 5

Development of Synthetic High Affinity Ligands that Bind to a Structural Epitope on the Tumor Cell Receptor HLA-DR10

A number of cell surface protein receptors have been identified that distinguish malignant cancer cells from their normal counterparts. While several of these receptors have been shown to be more abundant on cancer cells (e.g. CD20, CD22), others have been confirmed to differ structurally (e.g. HLA-DR10, Muc-1) from the same or closely related receptors present on normal cells. This has led to the development of a variety of antibody-based, receptor-specific reagents conjugated to radioisotopes for use in radio-immunotherapy. Lym-1, an antibody developed to bind to a unique structural epitope on the abundant cell surface receptor HLA-DR10 found only on human lymphoma and normal B-cell lymphocytes, has been used with some success in the treatment of non Hodgkin's lymphoma. In an effort to develop smaller and more effective therapeutics for treating non Hodgkin's lymphoma, we have synthesized the first in a series of small (<3 kD) selective high affinity ligands (SHALs) that bind to this same HLA-DR10 structural epitope. A homology model for HLA-DR10 was created using four known crystal structures of related HLA-DR molecules. Two unique "pockets" located on the surface of the protein adjacent to key amino acids required for Lym-1 binding were identified, and computational docking techniques were used to prescreen a large library of small molecules to predict which compounds should bind to each site. A small number of these compounds were tested experimentally using NMR spectroscopy to confirm their binding to the isolated HLA-DR10 protein, and pairs of compounds binding to the two different "pockets" were linked together using solid phase synthetic chemistry to create a series of bidentate reagents with different length linkers. The SHAL exhibiting the highest affinity for isolated HLA-DR10 (~23 nM) has been shown to bind selectively to nine different cultured cell lines containing HLA-DR10 and to frozen and fixed tissue sections obtained from patients with small cell and large cell human lymphomas. A bivalent form of this SHAL was also synthesized and shown to further enhance cell binding.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A polydentate selective high affinity ligand (SHAL) comprising a first ligand and a second ligand, wherein said first ligand and said second ligand bind to a first pocket and a second pocket, respectively, on the β-subunit of an HLA-DR10 surface antigen, said first and second pockets being two adjacent pockets flanking the R70 amino acid residue of the HLA-DR10 surface antigen, and wherein said first ligand is linked to said second ligand by a linker comprising polyethylene glycol or a linker comprising lysine and polyethylene glycol, and wherein said first ligand and second ligand is a peptide or a small organic molecule.

2. The SHAL of claim 1, wherein said first ligand and said second ligand are selected from Table 4.

3. The SHAL of claim 1, wherein said first ligand and said second ligand each is a small organic molecule.

4. The SHAL of claim 1, wherein said first ligand is selected from Table 2, and said second ligand is selected from Table 3.

5. The SHAL of claim 1, further comprising an effector attached to the SHAL, wherein the effector is selected from the group consisting of an epitope tag, an antibody, a second SHAL, a label, a cytotoxin, a liposome, a radionuclide, a drug, a prodrug, a viral particle, a cytokine, and a metal isotope.

6. The SHAL of claim 5, wherein said epitope tag is selected from the group consisting of an avidin, and a biotin.

7. The SHAL of claim 5, wherein said cytotoxin is selected from the group consisting of a Diphtheria toxin, a Pseudomonas exotoxin, a ricin, an abrin, and a thymidine kinase.

8. The SHAL of claim 5, wherein said metal isotope is selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

9. A pharmaceutical formulation said formulation comprising:

a pharmaceutically acceptable excipient and a SHAL of claim 1.

10. The pharmaceutical formulation of claim 9, wherein said formulation is a unit dosage formulation.

11. A pharmaceutical formulation said formulation comprising:

a pharmaceutically acceptable excipient and a SHAL of claim 5.

12. The pharmaceutical formulation of claim 11, wherein said formulation is a unit dosage formulation.

13. A method of inhibiting the growth or proliferation of a cancer cell that displays a Lym-1 epitope, said method comprising contacting said cell with a SHAL of claim 1.

14. The method of claim 13, wherein said cell is a metastatic cell.

15. The method of claim 13, wherein said cell is a solid tumor cell.

16. A method of inhibiting the growth or proliferation of a cancer cell, said method comprising contacting said cell with a SHAL of claim 1, wherein said SHAL is attached to a cytotoxin or a radionuclide.

17. The method of claim 16, wherein said cell is a metastatic cell.

18. The method of claim 16, wherein said cell is a solid tumor cell.

19. A method of detecting a cancer cell that displays a Lym-1 epitope, said method comprising:

contacting said cancer cell with a SHAL of claim 1, wherein said SHAL is attached to a detectable label; and detecting the presence or absence of said detectable label.

20. The method of claim 19, wherein said detectable label is a selected from the group consisting of a gamma-emitter, a positron-emitter, an x-ray emitter, an alpha emitter, and a fluorescence-emitter.

21. A method of detecting a cell that displays a Lym-1 epitope, said method comprising:

contacting a cell with a SHAL of claim 1, wherein said SHAL is attached to an epitope tag;

contacting said SHAL with a chelate comprising a detectable moiety whereby said chelate binds to said epitope tag thereby associating said detectable moiety with said cell; and detecting said detectable moiety.

22. The method of claim 21, wherein said detectable moiety is a radionuclide.

23. The method of claim 21, wherein said detectable moiety is selected from the group consisting of a gamma-emitter, a positron-emitter, an alpha emitter, an x-ray emitter, and a fluorescence-emitter.

24. The method of claim 21, wherein said cell is a cancer cell.

25. The method of claim 21, wherein said detecting comprises external imaging.

26. The method of claim 21, wherein said detecting comprises internal imaging.

27. The method of claim 21, wherein said detectable moiety comprises a metal isotope selected from the group consisting of $^{99}$Tc, $^{203}$Pb, $^{67}$Ga, $^{68}$Ga, $^{72}$As, $^{111}$In, $^{113m}$In, $^{97}$Ru, $^{62}$Cu, $^{64l}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag.

28. The method of claim 21, wherein said chelate comprises DOTA.

29. The method of claim 21, wherein said epitope tag is an avidin or a biotin.

30. A kit comprising a SHAL of claim 1 and an effector selected from the group consisting of an epitope tag, an antibody, a second SHAL, a label, a cytotoxin, a liposome, a radionuclide, a drug, a prodrug, a viral particle, a cytokine, and a metal isotope.

31. The kit of claim 30, wherein said SHAL is in a pharmacologically acceptable excipient.

32. A polydentate selective high affinity ligand (SHAL) comprising a first ligand and a second ligand, wherein said first ligand is linked to said second ligand by a linker comprising polyethylene glycol or a linker comprising lysine and polyethylene glycol, and wherein said first and second ligands are identified by a method comprising:

retrieving, by a computer, the three-dimensional structure of a first pocket and a second pocket on the β-subunit of an HLA-DR10 surface antigen, said first and second pockets being two adjacent pockets flanking the R70 amino acid residue of the HLA-DR10 surface antigen, retrieving the three-dimensional structures of a plurality of candidate molecules, determining, for each of said candidate molecules, whether the three-dimensional structure of the candidate molecule matches, spatially, to either of said pockets, and identifying a first ligand and a second, from the candidate molecules, that match said first pocket and second pocket, respectively.

33. The SHAL of claim 32, further comprising an effector attached to the SHAL, wherein the effector is selected from the group consisting of an epitope tag, an antibody, a second SHAL, a label, a cytotoxin, a liposome, a radionuclide, a drug, a prodrug, a viral particle, a cytokine, and a metal isotope.

* * * * *